United States Patent
Gerlach et al.

(10) Patent No.: US 6,699,877 B2
(45) Date of Patent: Mar. 2, 2004

(54) SUBSTITUTED 1,2,3,4-TETRAHYDROQUINOLINE-2-CARBOXYLIC ACID DERIVATIVES

(75) Inventors: Matthias Gerlach, Brachttal (DE); Michael Przewosny, Aachen (DE); Werner Englberger, Stolberg (DE); Elke Reissmueller, Bielefeld (DE); Petra Bloms-Funke, Wuerselen (DE); Corinna Maul, Aachen (DE); Utz-Peter Jagusch, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/213,436

(22) Filed: Aug. 7, 2002

(65) Prior Publication Data

US 2003/0087926 A1 May 8, 2003

Related U.S. Application Data

(63) Continuation of application No. PCT/EP01/00588, filed on Jan. 19, 2001.

(30) Foreign Application Priority Data

Feb. 7, 2000 (DE) .......................................... 100 05 302

(51) Int. Cl.⁷ .............................................. A01N 43/42
(52) U.S. Cl. ......................... 514/291; 514/311; 546/89; 546/165
(58) Field of Search ................................. 514/311, 291; 546/165, 89

(56) References Cited

PUBLICATIONS

Shu Kobayashi, J. Comb. Chem, vol 2, pp 438–440, 2000.*
Wojciech Danysz, et al., "Glycine and N–Methyl–D–Aspartate Receptors: Physiological Significance and Possible Therapeutic Applications" Pharmacological Reviews, vol. 50, No. 4, 1998, pp. 597–864.

* cited by examiner

*Primary Examiner*—D. Margaret Seaman
(74) *Attorney, Agent, or Firm*—Crowell & Moring LLP

(57) ABSTRACT

A substituted 1,2,3,4-tetrahydroquinoline-2-carboxylic acid derivative of formula I

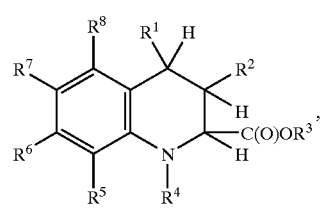

and salts thereof with pharmaceutically acceptable acids. Also disclosed are methods for making the derivative, and pharmaceutical compositions comprising the derivative. Methods for treating pain, migraine, and various other diseases using the pharmaceutical composition are also disclosed.

62 Claims, No Drawings

SUBSTITUTED 1,2,3,4-TETRAHYDROQUINOLINE-2-CARBOXYLIC ACID DERIVATIVES

CROSS REFERENCE TO RELATED APPLICATIONS

The present application is a continuation of international patent application no. PCT/EP01/00588, filed Jan. 19, 2001, designating the United States of America, the entire disclosure of which is incorporated herein by reference. Priority is claimed based on Federal Republic of Germany patent application no. 100 05 302.5, filed Feb. 7, 2000, the entire disclosure of which is also incorporated herein by reference.

BACKGROUND OF THE INVENTION

The present invention relates to substituted 1,2,3,4-tetrahydroquinoline-2-carboxylic acid derivatives, to a process for their preparation, their use for the preparation of pharmaceutical compositions and pharmaceutical compositions containing these compounds.

The treatment of chronic and non-chronic painful conditions is extremely important in medicine. There is a worldwide need for effective treatment of pain for patient-oriented and target-oriented treatment of chronic and non-chronic painful conditions, this concept being interpreted as the successful and satisfactory treatment of pain for the patient. This is manifested by the large number of scientific studies which have appeared recently in the field of applied analgesics and basic research in nociception.

Conventional opioids such as morphine are very effective in the therapy of strong to very strong pain. However, their use is limited by the known side effects, for example respiratory depression, vomiting, sedation, constipation and tolerance development. Furthermore, they are less effective for neuropathic or incidental pain suffered inter alia by tumor patients.

Opioids deploy their analgesic effect by binding to membrane receptors belonging to the family known as G-protein-coupled receptors (GPRC). The biochemical and pharmacological characterization of subtypes of these receptors has now raised hopes that subtype-specific opioids have a different profile of effects and side effects from, for example morphine. Further pharmacological investigations have in the meantime made the discovery of a plurality of subtypes of these opioid receptors ($\mu_1$, $\mu_2$, $\kappa_1$, $\kappa_2$, $\kappa_3$, $\delta_1$ and $\delta_2$) possible. There are further receptors and ion channels which participate substantially in the pain development and pain transmission system. The NMDA (N-methyl-D-aspartate) ion channel is particularly important: a substantial proportion of synaptic communication takes place through it. The exchange of calcium ions between the neuronal cell and its environment is controlled by this channel.

Information about the physiological significance of ion channel-selective substances has been obtained through the development of patch clamp technology. The effect of NMDA antagonists on the influx of calcium ions into the interior of the cell can thus be clearly demonstrated. It has also been found that these substances have an independent antinociceptive potential (for example, ketamine). It is important here that the mechanism of action is quite different, for example, from opiates, as NMDA antagonists intervene directly in the crucial calcium balance of the cells during the transmission of pain. It has therefore been possible, for the first time, to treat the neuropathic forms of pain successfully.

Various NMDA antagonists, which were tetrahydroquinoline derivatives in this case, have already been described in J. Med. Chem. (1992) 35, 1954–1968, J. Med. Chem. (1992) 35, 1942–1953 and Med. Chem. Res. (1991) 1; 64–73 and patent applications EP 386 839, WO 97/12879 A1, WO 98/07704 A1 and WO 98/42673 A1. A large number of possible indications, including the treatment of pain, have been mentioned, in particular, in the patent applications. However, the effectiveness and usefulness of these substances are still uncertain, so there is a need for further substances here.

DESCRIPTION OF THE INVENTION

One object of the invention was to provide analgesically acting substances, in particular NMDA antagonists, suitable for treating pain, in particular also chronic and neuropathic pain. In addition, these substances should have the fewest possible side effects such as nausea, vomiting, dependency, respiratory depression or constipation.

The invention accordingly relates to substituted 1,2,3,4-tetrahydroquinoline-2-carboxylic acid derivatives of general formula I, in the form of their racemates, enantiomers, diastereomers, in particular mixtures of their enantiomers or diastereomers or of an individual enantiomer or diastereomer; their bases and/or salts of physiologically acceptable acids,

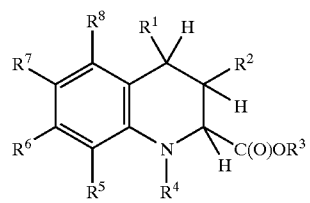

I wherein
either
$R^1$ and $R^2$ together, respectively singly or multiply substituted or unsubstituted, form
—(CH$_2$)$_n$— with n=3–10,
—CH=CH—CH$_2$—,
—CH=CH—CH$_2$—CH$_2$—,
—CH$_2$—CH=CH—CH$_2$—,
—CH$_2$—CH=CH—CH$_2$—CH$_2$—,
—CH$_2$—CH$_2$—CH=CH—CH$_2$—CH$_2$—,
—O—CH$_2$—CH$_2$—,
—O—CH$_2$—CH$_2$—CH$_2$—,
—CH$_2$—O—CH$_2$—,
—CH$_2$—CH$_2$—O—CH$_2$—,

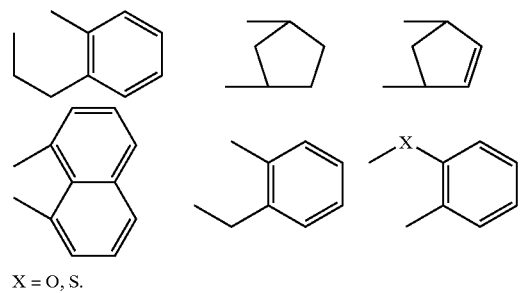

X = O, S.

$R^3$ is selected from
H; respectively branched or unbranched, singly or multiply substituted or unsubstituted $C_1$–$C_{18}$ alkyl, $C_2$–$C_{18}$ alkenyl or $C_2$–$C_{18}$ alkinyl; saturated or unsaturated, singly or multiply substituted or unsubstituted $C_3$–$C_8$ cycloalkyl, or a corresponding heterocycle, in which at least one carbon atom in the ring is replaced by N, S or O, respectively singly or multiply substituted or unsubstitued alkyl aryl or alkyl heteroaryl; respectively singly or multiply substituted or unsubstituted aryl or heteroaryl;

$R^4$ is selected from
$R^{4a}$ or $ZR^{4a}$ wherein Z is respectively branched or unbranched, singly or multiply substituted or unsubstituted $C_1$–$C_6$ alkyl, $C_2$–$C_6$ alkenyl or $C_2$–$C_6$ alkinyl, and $R^{4a}$ is selected from
H; respectively branched or unbranched, singly or multiply substituted or unsubstituted $C_1$–$C_{12}$ alkyl, $C_2$–$C_{12}$ alkenyl or $C_2$–$C_{12}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstituted aryl or heteroaryl;
$C(O)R^9$, $C(O)OR^9$, $C(S)R^9$, $C(S)OR^9$ or $SO_2)R^9$ with $R^9$ selected from
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstitued alkyl aryl or alkyl heteroaryl; respectively singly or multiply substituted or unsubstituted aryl or heteroaryl, in particular phenethyl, 1-adamantyl, 2-adamantyl, 1-naphthyl or 2-naphthyl 2-,3- or 4-pyridyl; thiazolyl;
$SR^{10}$ with $R^{10}$ selected from
respectively singly or multiply substituted or unsubstituted aryl or heteroaryl,
$C(O)NR^{11}R^{12}$, $C(O)NR^{11}NR^{12}R^{13}$, $C(NR^{11})NR^{12}R^{13}$, $C(S)NR^{11}R^{12}$ or $C(S)NR^{11}NR^{12}R^{13}$, wherein $R^{11}$, $R^{12}$ and $R^{13}$, independently of one another, are selected from
H; respectively branched or unbranched, singly or multiply substituted or un-substituted $C_1$–$C_{18}$ alkyl, $C_2$–$C_{18}$ alkenyl or $C_2$–$C_{18}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N, respectively singly or multiply substituted or unsubstitued alkyl aryl or alkyl heteroaryl; respectively singly or multiply substituted or unsubstituted aryl or heteroaryl;

$R^5$, $R^6$, $R^7$ and $R^8$, independently of one another, are selected from
H, F, Cl, Br, I, CN, $NO_2$; respectively branched or unbranched, singly or multiply substituted or unsubstituted $C_1$–$C_{10}$ alkyl, $C_2$–$C_{10}$ alkenyl or $C_2$–$C_{10}$ alkinyl;
$OR^{14}$, $OC(O)R^{14}$, $OC(S)R^{14}$, $C(O)R^{14}$, $C(O)OR^{14}$, $C(S)R^{14}$, $C(S)OR^{14}$, $SR^{14}$, $S(O)R^{14}$ or $S(O_2)R^{14}$, wherein $R^{14}$ is selected from
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstitued alkyl aryl or alkyl heteroaryl; respectively singly or multiply substituted or unsubstituted aryl or heteroaryl;
$NR^{15}R^{16}$, $NR^{15}C(O)R^{16}$, $C(NR^{15})NR^{16}R^{17}$, $NR^{15}C(S)R^{16}$, $C(S)NR^{15}R^{16}$ or $C(S)NR^{15}NR^{16}R^{17}$ or $S(O_2)NR^{15}R^{16}$, wherein $R^{15}$, $R^{16}$ and $R^{17}$, independently of one another, are selected from
H, O; respectively branched or unbranched, singly or multiply substituted or unsubstituted $C_1$–$C_{18}$ alkyl, $C_2$–$C_{18}$ alkenyl or $C_2$–$C_{18}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N, respectively singly or multiply substituted or unsubstitued alkyl aryl or alkyl heteroaryl; respectively singly or multiply substituted or unsubstituted aryl or heteroaryl;
or
$R^{15}$ and $R^{16}$ or $R^{16}$ and $R^{17}$ together form a saturated or unsaturated, singly or multiply substituted or unsubstituted $C_3$–$C_8$ cycloalkyl, or a corresponding heterocycle in which at least one carbon atom in the ring is replaced by S, O or N; or
$R^5$ and $R^6$, $R^6$ and $R^7$, or $R^7$ and $R^8$ jointly form
=$CR^{18}$—CH=CH—CH= or =CH—$CR^{18}$=CH—CH=,
wherein $R^{18}$ is
H, F, Cl, Br, I, OH or respectively branched or unbranched, singly or multiply substituted or unsubstituted $C_1$–$C_{10}$ alkyl, $C_2$–$C_{10}$ alkenyl or $C_2$–$C_{10}$ alkinyl;
providing that
if $R^1$ and $R^2$ together form —CH=CH—$CH_2$—

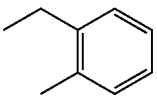

and $R^3$ corresponds to (-)$_p$-menthan-3-ol, in particular menthol or borneol, $R^7$=Cl and $R^5$, $R^6$ and $R^8$=H do not simultaneously apply,
if $R^1$ and $R^2$ together form —CH=CH—$CH_2$— and $R^3$ corresponds to $CH_3$, $R^7$=H, Cl or $OCH_3$ and $R^5$, $R^6$ and $R^8$=H do not simultaneously apply,
if $R^{1b}$ and $R^{2a}$ together form —CH=CH—$CH_2$— and $R^3$ corresponds to H, $R^7$=$OCH_3$ or $C(O)NH_2$ and $R^5$, $R^6$ and $R^8$=H, $R^5$ and $R^7$=$CH_3$ and $R^6$ and $R^8$=H or $R^5$=$OCH_3$ and $R^6$, $R^7$ and $R^8$=H do not simultaneously apply,
and
if $R^{1b}$ and $R^{2a}$ together form

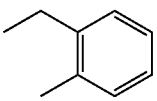

or —O—$CH_2$—$CH_2$— and $R^3$ corresponds to $C_2H_5$, $R^7$=H, Cl, $CH_3$, $OCH_3$ or $NO_2$ and $R^5$, $R^6$ and $R^8$=H or $R^5$=$NO_2$ and $R^6$, $R^7$ and $R^8$=H do not simultaneously apply;

or

R$^1$ is selected from
- branched or unbranched, singly or multiply substituted or unsubstituted C$_1$–C$_{10}$ alkyl; saturated or unsaturated, singly or multiply substituted or unsubstituted C$_3$–C$_8$ cycloalkyl, or a corresponding heterocycle, in which at least one carbon atom in the ring is replaced by S, O or N; singly or multiply substituted or unsubstituted alkyl aryl; singly or multiply substituted or unsubstituted aryl;
- OR$^{19}$, SR$^{19}$, SO$_2$R$^{19}$ with R$^{19}$ being selected from
  - respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N; respectively singly or multiply substituted or unsubstituted alkyl aryl, aryl, alkyl heteroaryl or heteroaryl;

R$^2$ is selected from
- H; branched or unbranched, singly or multiply substituted or unsubstituted C$_1$–C$_{10}$ alkyl; singly or multiply substituted or unsubstituted phenyl; wherein, if R$^2$ is phenyl, R$^1$ has to be aryl, O-aryl or S-aryl, R$^3$ is selected from
- H; respectively branched or unbranched, singly or multiply substituted or unsubstituted C$_1$–C$_{18}$ alkyl, C$_2$–C$_{18}$ alkenyl or C$_2$–C$_{18}$ alkinyl; saturated or unsaturated, singly or multiply substituted or unsubstituted C$_3$–C$_8$ cycloalkyl, or a corresponding heterocycle, in which at least one carbon atom in the ring is replaced by N, S or O, respectively singly or multiply substituted or unsubstitued alkyl aryl or alkyl heteroaryl; respectively singly or multiply substituted or unsubstituted aryl or heteroaryl;

R$^4$ is selected from
- R$^{4a}$ or ZR$^{4a}$ wherein Z is respectively branched or unbranched, singly or multiply substituted or unsubstituted C$_1$–C$_6$ alkyl; C$_2$–C$_6$ alkenyl or C$_2$–C$_6$ alkinyl, wherein R$^{4a}$ is
  - H; respectively branched or unbranched, singly or multiply substituted or unsubstituted C$_1$–C$_{12}$ alkyl, C$_2$–C$_{12}$ alkenyl or C$_2$–C$_{12}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N; respectively singly or multiply substituted or unsubstituted aryl or heteroaryl;
  - C(O)R$^9$, C(O)OR$^9$, C(S)R$^9$, C(S)OR$^9$ or S(O$_2$)R$^9$ with R$^9$ being selected from
    - H; respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N; respectively singly or multiply substitued alkyl aryl or alkyl heteroaryl; respectively singly or multiply substituted or unsubstituted aryl or heteroaryl, in particular phenethyl, 1-adamantyl, 2-adamantyl, 1-naphthyl or 2-naphthyl 2-,3- or 4-pyridyl; thiazolyl;
    - SR$^{10}$ with R$^{10}$ being
      - respectively singly or multiply substituted or unsubstituted aryl or heteroaryl,
    - C(O)NR$^{11}$R$^{12}$, C(O)NR$^{11}$NR$^{12}$R$^{13}$, C(NR$^{11}$)NR$^{12}$R$^{13}$, C(S)NR$^{11}$R$^{12}$ or C(S)NR$^{11}$NR$^{12}$R$^{13}$, wherein R$^{11}$, R$^{12}$ and R$^{13}$, independently of one another, are selected from
      - H; respectively branched or unbranched, singly or multiply substituted or unsubstituted C$_1$–C$_{18}$ alkyl, C$_2$–C$_{18}$ alkenyl or C$_2$–C$_{18}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N, respectively singly or multiply substituted or unsubstitued alkyl aryl or alkyl heteroaryl; respectively singly or multiply substituted or unsubstituted aryl or heteroaryl;

R$^5$, R$^6$, R$^7$ and R$^8$, independently of one another, are
- H, F, Cl, Br, I, CN, NO$_2$; respectively branched or unbranched, singly or multiply substituted or unsubstituted C$_1$–C$_{10}$ alkyl, C$_2$–C$_{10}$ alkenyl or C$_2$–C$_{10}$ alkinyl;
- OR$^{14}$, OC(O)R$^{14}$, OC(S)R$^{14}$, C(O)R$^{14}$, C(O)OR$^{14}$, C(S)R$^{14}$, C(S)OR$^{14}$, SR$^{14}$, S(O)R$^{14}$ or S(O$_2$)R$^{14}$, wherein R$^{14}$ is
  - H; respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N; respectively singly or multiply substituted or unsubstitued alkyl aryl or alkyl heteroaryl; or respectively singly or multiply substituted or unsubstituted aryl or heteroaryl;
- NR$^{15}$R$^{16}$, NR$^{15}$C(O)R$^{16}$, C(NR$^{15}$)NR$^{16}$R$^{17}$, NR$^{15}$C(S)R$^{16}$, C(S)NR$^{15}$R$^{16}$ or C(S)NR$^{15}$NR$^{16}$R$^{17}$ or S(O$_2$)NR$^{15}$R$^{16}$, wherein R$^{15}$, R$^{16}$ and R$^{17}$, independently of one another, are
  - H, O; respectively branched or unbranched, singly or multiply substituted or unsubstituted C$_1$–C$_{18}$ alkyl, C$_2$–C$_{18}$ alkenyl or C$_2$–C$_{18}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N, respectively singly or multiply substituted or unsubstitued alkyl aryl or alkyl heteroaryl; respectively singly or multiply substituted or unsubstituted aryl or heteroaryl;
  - or
  - R$^{15}$ and R$^{16}$ or R$^{16}$ and R$^{17}$ together form a saturated or unsaturated, singly or multiply substituted or unsubstituted C$_3$–C$_8$ cycloalkyl, or a corresponding heterocycle in which at least one carbon atom in the ring is replaced by S, O or N; or R$^5$ and R$^6$, R$^6$ and R$^7$ or R$^7$ and R$^8$ jointly form
=CR$^{18}$—CH=CH—CH= or =CH—CR$^{18}$=CH—CH=, with R$^{18}$ selected from
- H, F, Cl, Br, I, OH or respectively branched or unbranched, singly or multiply substituted or unsubstituted C$_1$–C$_{10}$ alkyl, C$_2$–C$_{10}$ alkenyl or C$_2$–C$_{10}$ alkinyl;

providing that
if $R^4$, $R^6$, $R^7$ and $R^8$=H,
$R^1$=CH$_3$, $R^3$=H or CH$_3$ and $R^2$ and $R^5$=H do not simultaneously apply;
$R^1$ is unsubstituted phenyl, $R^3$=C$_2$H$_5$ and $R^2$ and $R^5$=H do not simultaneously apply;
if $R^4$, $R^6$, $R^7$ and $R^8$=H,
$R^1$=S-phenyl, $R^2$=H, $R^7$=Cl and $R^3$=CH$_3$ do not simultaneously apply; or
$R^1$=—S-2-pyridinyl, $R^2$=CH$_3$, $R^7$=OCH$_3$ and $R^3$=—CH$_3$—CH=CH$_2$ do not simultaneously apply; or
if $R^2$, $R^4$, $R^5$ and $R^7$=H and $R^6$ and $R^8$=Cl,
$R^1$=dioxalan and $R^3$=—CH$_2$—CH$_2$—OH do not simultaneously apply.

The 1,2,3,4-tetrahydroquinoline-2-carboxylic acid derivatives according to the invention are NMDA antagonists which act selectively on the glycine binding site and also exhibit pronounced analgesic response.

In the context of this invention, the term substituted as used in connection with alkyl, alkenyl, alkinyl and cycloalkyl or the "corresponding heterocycle" refers to the substitution of a hydrogen radical by F, Cl, Br, I, NH$_2$, SH or OH, multiply substituted radicals being radicals which are multiply substituted at different or at identical atoms, or both, for example triply at the same carbon atom as in the case of CF$_3$ or at different sites as in the case of —CH(OH)—CH=CH—CHCl$_2$.

—C(O)— represents

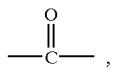

and this also applies to —C(S)— or —S(O)— and —S(O$_2$)—.

The term "C$_1$–C$_8$ alkyl" and "C$_1$–C$_{10}$ alkyl" in the context of this invention refers to hydrocarbons containing 1 to 8 and 1 to 10 carbon atoms. Examples include methyl, ethyl, propyl, isopropyl, n-butane, sec-butyl, tert-butyl, n-pentane, neopentyl, n-hexane, n-heptane, n-octane, n-nonane and n-decane.

The term "C$_1$–C$_{18}$ alkyl" in the context of this invention refers to hydrocarbons containing 1 to 18 carbon atoms. Examples include unsubstituted or singly or multiply substituted methyl, ethyl, propyl, isopropyl, n-butane, sec-butyl, tert-butyl, n-pentane, neopentyl, n-butane, sec-butyl, tert-butyl, n-hexane, n-heptane, n-octane, n-nonane, n-decane, n-undecane, n-dodecane, n-dodecane, n-tridecane, n-tetradecane, n-pentadecane, n-hexadecane, n-heptadecane and n-octadecane.

The term "C$_2$–C$_{10}$ alkenyl" and "C$_2$–C$_{10}$ alkinyl" or "C$_2$–C$_{18}$ alkenyl" and "C$_2$–C$_{18}$ alkinyl" in the context of this invention refers to hydrocarbons containing 2 to 8 and 2 to 18 carbon atoms. Examples include unsubstituted or singly or multiply substituted methenyl, propenyl, butenyl, pentenyl, hexenyl, heptenyl, octenyl and unsubstituted or singly or multiply substituted methinyl, propinyl, butinyl, pentinyl, hexinyl, heptinyl, and octinyl.

The term "C$_3$–C$_7$ cycloalkyl" in the context of this invention refers to cyclic hydrocarbons containing 3 to 7 carbon atoms. Examples include saturated or unsaturated, unsubstituted or singly or multiply substituted cyclopropyl, cyclobutyl, cyclopentyl, cyclohexyl, cycloheptyl, cyclopentenyl, cyclohexenyl and cycloheptenyl. The term "corresponding heterocycle" in the context of the invention refers to a C$_3$–C$_7$ cycloalkyl in which at least one carbon atom in the ring is replaced by S, O or N. Examples include pyrrolidine, pyrane, thiolane, piperidine and tetrahydrofuran.

The term "aryl" in the context of this invention refers to phenyls, naphthyls or anthracenyls. The aryl radicals may also be condensed with further rings.

The term "heteroaryl" in the context of this invention refers to aromatic compounds which are optionally provided with a partially condensed ring system and contain at least one heteroatom from the group comprising nitrogen, oxygen and/or sulphur. Examples from this group include thiophen, furan, pyrrol, pyridine, pyrimidine, quinoline, isoquinoline, phtlalazine or quinazoline.

The term "alkylaryl" and "alkylheteroaryl" in the context of this invention refers to aryls and heteroaryls substituted at least with C$_1$–C$_6$ alkylene, the terms aryl, heteroaryl and alkyl having the same meaning as above, in which the bond is produced via the alkyl radical.

With respect to "aryl", "alkylaryl", "heteroaryl" or "alkylheteroaryl" in the context of this invention, the term singly or multiply substituted refers to the substitution of the ring system with F, Cl, Br, I, NH$_2$, SH, OH, CF$_3$; =O or =S; singly or multiply substituted or unsubstituted C$_1$–C$_6$ alkyl, C$_1$–C$_6$ alkoxy, C$_2$–C$_8$ alkenyl, C$_2$–C$_8$ alkinyl; phenyl or benzyl or dioxolyl; at one or more atoms.

The term concerning the salt formed with a physiologically acceptable acid in the context of this invention refers to salts of the respective active ingredient with inorganic or organic acids which are physiologically acceptable, in particular when used in humans and/or mammals. Hydrochloride is particularly preferred.

The application particularly preferably relates to substituted 1,2,3,4-tetrahydroquinoline-2-carboxylic acid derivatives according to the invention of Formula I in which $R^4$ is selected from H; respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl;

C(O)R$^9$ with R$^9$ being
H; respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl, respectively singly or multiply substituted or unsubstituted aryl or heteroaryl, in particular phenethyl, 1-adamantyl, 2-adamantyl, 1-naphthyl or 2-naphthyl 2-,3- or 4-pyridyl; or thiazolyl.

Particularly preferred are substituted 1,2,3,4-tetrahydroquinoline-2-carboxylic acid derivatives according to the invention of Formula I, in which $R^4$ is selected from H; unsubstituted or singly or multiply substituted C$_1$–C$_{10}$ alkyl; unsubstituted or singly or multiply substituted phenyl; preferably H, CH$_3$ or C$_2$H$_5$, in particular H.

The application preferably relates to substituted 1,2,3,4-tetrahydroquinoline-2-carboxylic acid derivatives according to the invention of Formula I, in which $R^3$ is selected from H; respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl, or a corresponding heterocycle, in which at least one carbon atom in the ring is replaced by N or O; singly or multiply substituted or unsubstitued alkyl aryl; respectively singly or multiply substituted or unsubstituted aryl or heteroaryl.

Particularly preferred are substituted 1,2,3,4-tetrahydroquinoline-2-carboxylic acid derivatives according to the invention of Formula I, in which $R^3$ is selected from H; branched or unbranched, singly or multiply substituted or unsubstituted $C_1$–$C_4$ alkyl; singly or multiply substituted or unsubstituted phenyl, benzyl or phenethyl, preferably H, $CH_3$ or $C_2H_5$, in particular H.

Particularly preferred are substituted 1,2,3,4-tetrahydroquinoline-2-carboxylic acid derivatives according to the invention of Formula I, in which $R^1$ and $R^2$ together form —O—$CH_2$—$CH_2$—, (—$CH_2$—)$_n$ with n=3–6, preferably 3 or 6, —CH=CH—$CH_2$—,

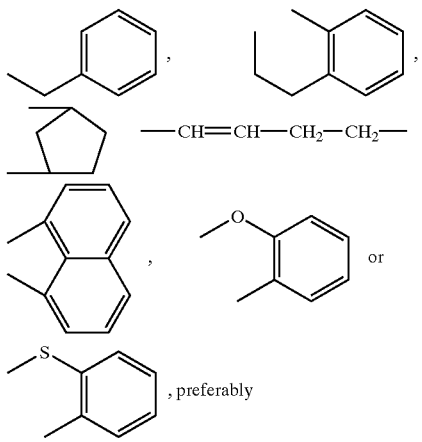

—CH=CH—$CH_2$— or —CH=CH—$CH_2$—$CH_2$—, in particular —CH=CH—$CH_2$—.

The application also preferably relates to substituted 1,2,3,4-tetrahydroquinoline-2-carboxylic acid derivatives according to the invention of Formula I, in which $R^1$ is selected from unsubstituted or singly or multiply substituted phenyl, naphthyl or anthracenyl; $OR^{19}$ or $SR^{19}$ with $R^{19}$ being branched or unbranched, singly or multiply substituted or unsubstituted $C_1$–$C_6$ alkyl; saturated or unsaturated, singly or multiply substituted or unsubstituted $C_3$–$C_8$ cycloalkyl; singly or multiply substituted or unsubstituted aryl;

preferably anthracenyl, naphthyl or, in particular, phenyl, unsubstituted or singly or multiply substituted with a substituent selected from:

F, Cl, Br, I, methoxy, ethoxy, propoxy, methyl, ethyl, propyl (n-propyl, i-propyl), butyl (n-butyl, i-butyl, t-butyl), carboxy, nitro, benzyloxy, phenyl, hydroxy, phenoxy, tri-fluormethyl, dioxolyl or $SCH_3$ or $OR^{19}$ or $SR^{19}$ with $R^{19}$ being branched or unbranched, singly or multiply substituted or unsubstituted $C_1$–$C_4$ alkyl; saturated or unsaturated, singly or multiply substituted or unsubstituted $C_3$–$C_8$ cycloalkyl; or singly or multiply substituted or unsubstituted aryl;

in particular unsubstituted phenyl, naththyl and anthracenyl; O-hydroxyethyl, ethoxynaphthyl, 4-hydroxy-3-methoxyphenyl, 4-propoxyphenyl, 2,3,4-trimethulphenyl, 2,4,5-trimethoxyphenyl, $SCH_3$, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2,6-dichlorophenyl, 4-carboxyphenyl, 3-nitrophenyl, 2,4,6-trimethylphenyl, 2,5-dimethylphenyl, 3,4-dimethoxyphenyl, 4-benzyloxy-3-methoxyphenyl, 3-methylphenyl, 4-methoxyphenyl, 4-biphenyl, 4-methylphenyl, 4-ethoxyphenyl, 2-methylphenyl, 2,4-dimethylphenyl, 2,6-dimethylphenyl, 4-hydroxy-3-methoxyphenyl, 4-methylhydroxyphenyl, 4-hydroxyphenyl, 4-phenoxyphenyl, 4-nitrophenyl, 4-chloromethylphenyl, 4-tert-butylphenyl, 3,5-bis(trifluoromethyl)phenyl, 4-acetoxyphenyl, 4-cyanophenyl, 2-methoxyphenyl, 2,6-difluorophenyl, 2-trifluoromethylphenyl, 3-trifuloromethylphenyl, 4-trifluoromethylphenyl, 3-methoxyphenyl, 2-, 3- or 4-benzyloxyphenyl, or S-phenyl or 6-chlorobenzo[1,3]dioxol-5-yl.

The application also preferably relates to substituted 1,2,3,4-tetrahydroquinoline-2-carboxylic acid derivatives according to Formula 1, in which $R^2$ is selected from H; branched or unbranched, singly or multiply substituted or unsubstituted $C_1$–$C_4$ alkyl; singly or multiply substituted or unsubstituted phenyl, preferably H, unsubstituted phenyl; 4-methoxyphenyl or $CH_3$, in particular H.

The application preferably relates to substituted 1,2,3,4-tetrahydroquinoline-2-carboxylic acid derivatives according to the invention of Formula I, in which $R^5$, $R^6$, $R^7$ and $R^8$, independently of one another, are selected from H, F, Cl, Br, I, CN, $NO_2$; respectively branched or unbranched, singly or multiply substituted or unsubstituted $C_1$–$C_{10}$ alkyl, $C_2$–$C_{10}$ alkenyl or $C_2$–$C_{10}$ alkinyl; $OR^{14}$, $C(O)R^{14}$, $C(O)OR^{14}$ or $SR^{14}$, wherein $R^{14}$ is selected from H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstitued alkyl aryl or alkyl heteroaryl; respectively singly or multiply substituted or unsubstituted aryl or heteroaryl;

$NR^{15}R^{16}$, $NR^{15}C(O)R^{16}$, wherein $R^{15}$ and $R^{16}$, independently of one another, are selected from H, O; respectively branched or unbranched, singly or multiply substituted or unsubstituted $C_1$–$C_{10}$ alkyl, $C_2$–$C_{10}$ alkenyl or $C_2$–$C_{10}$ alkinyl.

Particularly preferred are substituted 1,2,3,4-tetrahydroquinoline-2-carboxylic acid derivatives according to the invention of Formula I, in which $R^5$, $R^6$, $R^7$ and $R^8$, independently of one another, are selected from H, F, Cl, Br, I, CN, $NO_2$; respectively branched or unbranched, singly or multiply substituted or unsubstituted $C_1$–$C_6$ alkyl, $C_2$–$C_6$ alkenyl or $C_2$–$C_6$ alkinyl; $OR^{14}$, $C(O)R^{14}$, $C(O)OR^{14}$ or $SR^{14}$, wherein $R^{14}$ is selected from H; branched or unbranched, singly or multiply substituted or unsubstituted $C_1$–$C_4$ alkyl; singly or multiply substituted or unsubstituted aryl, preferably $R^5$, $R^6$, $R^7$ and $R^8$, independently of one another, are selected from H, F, Cl, Br, I, CN; branched or unbranched, singly or multiply substituted or unsubstituted $C_1$–$C_4$ alkyl; $OR^{14}$ or $SR^{14}$, with $R^{14}$ selected from branched or unbranched, singly or multiply substituted or unsubstituted $C_1$–$C_4$ alkyl; singly or multiply substituted or unsubstituted aryl, in particular $R^5$, $R^6$, $R^7$ and $R^8$, independently of one another, are selected from the group consisting of H, F, Cl, Br, I, CN; $CH_3$, $CF_3$, t-butyl, i-butyl, —$OCH_3$, —$OCF_3$, —$SCH_3$, and —O-phenyl.

Quite particularly preferred are substituted 1,2,3,4-tetrahydroquinoline-2-carboxylic acid derivatives according to the invention of Formula I, in which $R^5$, $R^6$ and $R^8$ represent H and R represents Cl or
$R^5$ and $R^7$ represent H and $R^6$ and $R^8$ represent Cl.

The application preferably relates, in particular, to the following substituted 1,2,3,4-tetrahydroquinoline-2-carboxylic acid derivatives according to the invention:

7,9-dichloro-3a,4,5,9b-tetrahydro-3H-cyclopenta[c]quinoline-4-carboxylic acid ethyl ester,
7,9-dichloro-3a,4,5,9b-tetrahydro-3H-cyclopenta[c]quinoline-4-carboxylic acid,
8-chloro-3a,4,5,9b-tetrahydro-3H-cyclopenta[c]quinoline-4-carboxylic acid ethyl ester,
8-chloro-3a-4,5,9b-tetrahydro-3H-cyclo-penta[c]quinoline-4-carboxylic acid,
6-chloro-4-phenyl-1,2,3,4-tetrahydroquinoline-2-carboxylic acid ethyl ester,
2-phenoxy-5,6a,11,11a-tetrahydro-6H-indene[1,2-c]quinoline-6-carboxylic acid ethyl ester,
6-chloro-4-(3-fluorophenyl)-1,2,3,4-tetrahydroquinoline-2-carboxylic acid ethyl ester,
5,7-dichloro-4-(3-fluorophenyl)-1,2,3,4-tetrahydroquinoline-2-carboxylic acid ethyl ester,
6-chloro-7-trifluoromethyl-4-(2,4,6-trimethylphenyl)-1,2,3,4-tetrahydroquinoline-2-carboxylic acid,
4-(2-hydroxy-ethoxy)-6-trifluoromethoxy-1,2,3,4-tetrahydroquinoline-2-carboxylic acid,
5,7-dichloro-4-naphthalene-2-yl-1,2,3,4-tetrahydroquinoline-2-carboxylic acid ethyl ester,
1,3-dichloro-5,6,6a,7,8,12b-hexahydrobenzo[k]phenanthridine-6-carboxylic acid ethyl ester,
6-iodo-4-(4-methoxyphenyl)-3-methyl-1,2,3,4-tetrahydroquinoline-2-carboxylic acid,
5,7-dichloro-4-phenyl-1,2,3,4-tetrahydroquinoline-2-carboxylic acid ethyl ester,
5,7-dichloro-4-phenyl-1,2,3,4-tetrahydroquinoline-2-carboxylic acid,
5,7-dichloro-4-o-tolyl-1,2,3,4-tetrahydroquinoline-2-carboxylic acid ethyl ester,
5,7-dichloro-4-m-tolyl-1,2,3,4-tetrahydroquinoline-2-carboxylic acid ester,
5,7-dichloro-4-m-tolyl-1,2,3,4-tetrahydroquinoline-2-carboxylic acid,
5,7-dichloro-4-p-tolyl-1,2,3,4-tetrahydroquinoline-2-carboxylic acid ethyl ester,
5,7-dichloro-4-p-tolyl-1,2,3,4-tetrahydroquinoline-2-carboxylic acid,
5,7-dichloro-4-(2,4-dimethylphenyl)-1,2,3,4-tetrahydroquinoline-2-carboxylic acid ethyl ester,
5,7-dichloro-4-(2,4-dimethylphenyl)-1,2,3,4-tetrahydroquinoline-2-carboxylic acid,
5,7-dichloro-4-(2,5-dimethylphenyl)-1,2,3,4-tetrahydroquinoline-2-carboxylic acid ethyl ester,
5,7-dichloro-4-(3,5-dimethylphenyl)-1,2,3,4-tetrahydroquinoline-2-carboxylic acid ethyl ester,
4-(4-tert-butylphenyl)-5,7-dichloro-1,2,3,4-tetrahydroquinoline-2-carboxylic acid ethyl ester,
5,7-dichloro-4-(2-fluorophenyl)-1,2,3,4-tetrahydroquinoline-2-carboxylic acid ethyl ester,
5,7-dichloro-4-(2-fluorophenyl)-1,2,3,4-tetrahydroquinoline-2-carboxylic acid,
5,7-dichloro-4-(3-fluorophenyl)-1,2,3,4-tetrahydroquinoline-2-carboxylic acid ethyl ester,
5,7-dichloro-4-(3-fluorophenyl)-1,2,3,4-tetrahydroquinoline-2-carboxylic acid,
5,7-dichloro-4-(4-fluorophenyl)-1,2,3,4-tetrahydroquinoline-2-carboxylic acid ethyl ester,
5,7-dichloro-4-(4-fluorophenyl)-1,2,3,4-tetrahydroquinoline-2-carboxylic acid,
5,7-dichloro-4-(2-chlorophenyl)-1,2,3,4-tetrahydroquinoline-2-carboxylic acid,
5,7-dichloro-4-(2-chlorophenyl)-1,2,3,4-tetrahydroquinoline-2-carboxylic acid ethyl ester,
5,7-dichloro-4-(3-chlorophenyl)-1,2,3,4-tetrahydroquinoline-2-carboxylic acid ethyl ester,
5,7-dichloro-4-(4-chlorophenyl)-1,2,3,4-tetrahydroquinoline-2-carboxylic acid,
5,7-dichloro-4-(2-bromophenyl)-1,2,3,4-tetrahydroquinoline-2-carboxylic acid ethyl ester,
5,7-dichloro-4-(3-bromophenyl)-1,2,3,4-tetrahydroquinoline-2-carboxylic acid ethyl ester,
5,7-dichloro-4-(3-bromophenyl)-1,2,3,4-tetrahydroquinoline-2-carboxylic acid,
5,7-dichloro-4-(4-bromophenyl)-1,2,3,4-tetrahydroquinoline-2-carboxylic acid ethyl ester,
5,7-dichloro-4-(4-bromophenyl)-1,2,3,4-tetrahydroquinoline-2-carboxylic acid,
5,7-dichloro-4-(3-trifluoromethylphenyl)-1,2,3,4-tetrahydroquinoline-2-carboxylic acid ethyl ester,
5,7-dichloro-3-methyl-4-phenyl-1,2,3,4-tetrahydroquinoline-2-carboxylic acid ethyl ester,
5,7-dichloro-4-(4-methoxyphenyl)-3-phenyl-1,2,3,4-tetrahydroquinoline-2-carboxylic acid ethyl ester,
5,7-dichloro-3,4-bis(4-methoxyphenyl)-3-methyl-1,2,3,4-tetrahydroquinoline-2-carboxylic acid ethyl ester,
5,7-dichloro-4-(4-methoxyphenyl)-3-methyl-1,2,3,4-tetrahydroquinoline-2-carboxylic acid ethyl ester,
5,7-dichloro-4-(3,4-methoxyphenyl)-3-methyl-1,2,3,4-tetrahydroquinoline-2-carboxylic acid ethyl ester,
5,7-dichloro-3-methyl-4-(2,4,5-trimethoxyphenyl)-1,2,3,4-tetrahydroquinoline-2-carboxylic acid ethyl ester,
6-chloro-4-o-tolyl-1,2,3,4-tetrahydroquinoline-2-carboxylic acid ethyl ester,
6-chloro-4-(2,4,6-trimethylphenyl)-1,2,3,4-tetrahydroquinoline-2-carboxylic acid ethyl ester,
6-chloro-4-(3-fluorophenyl)-1,2,3,4-tetrahydroquinoline-2-carboxylic acid ethyl ester,
6-chloro-4-(4-fluorophenyl)-1,2,3,4-tetrahydroquinoline-2-carboxylic acid ethyl ester,
6-chloro-4-(2-chlorophenyl)-1,2,3,4-tetrahydroquinoline-2-carboxylic acid ethyl ester,
6-chloro-4-(4-chlorophenyl)-1,2,3,4-tetrahydroquinoline-2-carboxylic acid ethyl ester,
6-chloro-4-(2-bromophenyl)-1,2,3,4-tetrahydroquinoline-2-carboxylic acid ethyl ester,
6-chloro-4-(3-bromophenyl)-1,2,3,4-tetrahydroquinoline-2-carboxylic acid ethyl ester,
6-chloro-4-(4-bromophenyl)-1,2,3,4-tetrahydroquinoline-2-carboxylic acid ethyl ester,
6-chloro-4-(4-trifluoromethylphenyl)-1,2,3,4-tetrahydroquinoline-2-carboxylic acid ethyl ester,
6-chloro-4-(2-methoxyphenyl)-1,2,3,4-tetrahydroquinoline-2-carboxylic acid ethyl ester,
7,9-dichloro-2,3,3a,4,5,9b-hexahydro-1H-cyclopenta[c]quinoline-4-carboxylic acid ethyl ester,
1,3-dichloro-7,10-methano-5,6,6a,7,8,9,10,10a-octahydrophenanthridine-6-carboxylic acid ethyl ester,
5,6a,7,11b-tetrahydro-6H-indeno-[2,1-c]quinoline-6-carboxylic acid ethyl ester,
10,12-dichloro-6b,7,8,12b-tetrahydro-8-azabenzo[j]fluoroanthrene-7-carboxylic acid ethyl ester,
1,3-dichloro-5,6,6a,11a-tetrahydro-11-oxa-5-aza-benzo[a]fluoroene-6-carboxylic acid ethyl ester,
1,3-dichloro-5,6,6a,11a-tetrahydro-11-thia-5-aza-benzo[a]fluoroene-6-carboxylic acid ethyl ester, 7,8-dichloro-4-(2-chlorophenyl)-1,2,3,4-tetrahydroquinoline-2-carboxylic acid,
6-cyano-4-(2,3,4-trimethoxyphenyl)-1,2,3,4-tetrahydroquinoline-2-carboxylic acid,
6,8,9-trichloro-2,3,3a,4,5,9b-hexahydro-furo[3,2-c]quinoline-4-carboxylic acid,
8-methoxy-4-(4-methoxyphenyl)-3-methyl-1,2,3,4-tetrahydroquinoline-2-carboxylic acid,
5,6,8-trichloro-4-(4-hydroxyphenyl)-3-methyl-1,2,3,4-tetrahydroquinoline-2-carboxylic acid,
4-(3,4-dimethoxyphenyl)-8-iodo-1,2,3,4-tetrahydroquinoline-2-carboxylic acid,
6-iodo-4-(4-methylsulphanylphenyl)-1,2,3,4-tetrahydroquinoline-2-carboxylic acid,
4-(4-ethoxy-3-methoxyphenyl)-6-phenoxy-1,2,3,4-tetrahydroquinoline-2-carboxylic acid,
4-(2-ethoxy-naphthalene-1-yl)-6-iodo-1,2,3,4-tetrahydroquinoline-2-carboxylic acid,
8-chloro-4-(4-propoxyphenyl)-1,2,3,4-tetrahydroquinoline-2-carboxylic acid,
4-(2,4-dimethoxy-3-methylphenyl)-6-phenoxy-1,2,3,4-tetrahydroquinoline-2-carboxylic acid,
2-trifluoromethoxy-5,6,6a,7,8,9,10,11,12,12a-decahydro-5-aza-cycloocta-[a]naphthalene-6-carboxylic acid ethyl ester,
6-sec-butyl-4-(6-chlorobenzo[1,3]dioxol-5-yl)-1,2,3,4-tetrahydroquinoline-2-carboxylic acid ethyl ester,
4-anthracene-9-yl-6-chloro-8-methyl-1,2,3,4-tetrahydroquinoline-2-carboxylic acid,
6-sec-butyl-4-naphthalene-1-yl-1,2,3,4-tetrahydroquinoline-2-carboxylic acid,
4-(4-hydroxyphenyl)-3-methyl-8-phenoxy-1,2,3,4-tetrahydroquinoline-2-carboxylic acid,
8-chloro-6-fluoro-4-naphthalene-2-yl-1,2,3,4-tetrahydroquinoline-2-carboxylic acid,
4-(4-methoxyphenyl)-3-methyl-6-phenoxy-1,2,3,4-tetrahydroquinoline-2-carboxylic acid,
6-chloro-8-fluoro-4-m-tolyl-1,2,3,4-tetrahydroquinoline-2-carboxylic acid,
8-chloro-6-fluoro-4-m-tolyl-1,2,3,4-tetrahydroquinoline-2-carboxylic acid,
4-(4-bromophenyl)-6-chloro-8-fluoro-1,2,3,4-tetrahydroquinoline-2-carboxylic acid,
7,8-dichloro-4-(2,4-dimethylphenyl)-1,2,3,4-tetrahydroquinoline-2-carboxylic acid,
6-chloro-4-(4-chlorophenyl)-7-trifluoromethyl-1,2,3,4-tetrahydroquinoline-2-carboxylic acid,
2-cyano-5,6a,7,11b-tetrahydro-6H-indeno[2,1-c]quinoline-6-carboxylic acid ethyl ester,
4-(2-chlorophenyl)-6-cyano-1,2,3,4-tetrahydroquinoline-2-carboxylic acid,
6-bromo-8-chloro-3-methyl-4-phenyl-1,2,3,4-tetrahydroquinoline-2-carboxylic acid ethyl ester,
6-bromo-8-chloro-4-(2,4-dimethylphenyl)-1,2,3,4-tetrahydroquinoline-2-carboxylic acid,
6-bromo-4-(2-bromophenyl)-8-chloro-1,2,3,4-tetrahydroquinoline-2-carboxylic acid,
4-(4-hydroxy-3-methoxyphenyl)-3-methyl-6-methylsulphanyl-1,2,3,4-tetrahydroquinoline-2-carboxylic acid,
6-cyano-3,4-bis-(4-methoxyphenyl)-1,2,3,4-tetrahydroquinoline-2-carboxylic acid,
8-chloro-6-fluoro-3,4-bis-(4-methoxyphenyl)-1,2,3,4-tetrahydroquinoline-2-carboxylic acid ethyl ester,
4-(4-benzyloxy-3-methoxyphenyl)-6-tert-butyl-1,2,3,4-tetrahydroquinoline-2-carboxylic acid ethyl ester,
5,7-dichloro-4-(4-chlorophenyl)-1,2,3,4-tetrahydroquinoline-2-carboxylic acid,
5,7-dichloro-4-(3-chlorophenyl)-1,2,3,4-tetrahydroquinoline-2-carboxylic acid,
5,7-dichloro-4-(4-chlorophenyl)-1,2,3,4-tetrahydroquinoline-2-carboxylic acid,
1,3-dichloro-5,6,6a,7,8,12b-hexahydrobenzo[k]phenanthridine-6-carboxylic acid,
1,3-dichloro-5,6a,7,11b-tetrahydro-6H-indeno[2,1-c]quinoline-6-carboxylic acid, and
5,7-dichloro-4-(3,5-dimethyl-phenyl)-1,2,3,4-tetrahydroquinoline-2-carboxylic acid.

Substituted 1,2,3,4-tetrahydroquinoline-2-carboxylic acid derivatives according to the invention in the form of their hydrochloride salts are particularly preferred.

The invention also relates to a process for preparing substituted 1,2,3,4-tetrahydroquinoline-2-carboxylic acid derivatives according to the invention.

Various processes for preparing tetrahydroquinolines are described in the literature:
a solid phase formulation (WO 98/34111),
multi-stage process control (WO 98/42673; Bioorganic and Medicinal Chemistry Letters Vol. 2, p. 371,1992; Journal of Heterocyclic Chemistry Vol. 25, p. 1831, 1988; Journal of the Chemical Society, Perkin Transactions 1 (1989), page 2245) or
a Lewis acid-catalysed "One-pack" process (Journal of the Chemical Society, Chemical Communications, 1999, p. 651; Journal of the American Chemical Society, Vol. 118, p. 8977, 1996).

However, all these processes obviously have a few drawbacks.

The present invention uses a "one-pack" process as the basic process. The inventive process uses trifluoroacetic acid, in which a respective aromatic amine, aldehyde and electron-rich olefin component react with one another.

Substituted 1,2,3,4-tetrahydroquinoline-2-carboxylic acid derivatives of Formula I, wherein $R^4$=H, whereas the other radicals have one of the aforementioned meanings are initially prepared by the basic process. Anilines according to Formula II, in which $R^5$, $R^6$, $R^7$ and $R^8$ have one of the meanings already given

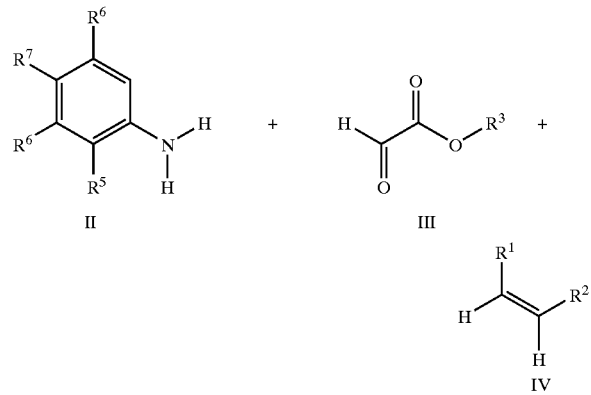

are reacted with a glyoxalic acid ester according to Formula III and olefins according to Formula IV, in which $R^1$ and $R^2$ have one of the meanings already given, with trifluoroacetic acid at between 0 and 100° C. It is preferred if the reaction period lasts 0.25 to 12 hours, preferably a maximum of 2 h. The reaction preferably takes place at a temperature between 20 and 40° C., preferably at ambient temperature and/or the reaction is a one-pack reaction.

A decisive advantage of the process according to the invention is that the process leads very selectively to the desired compounds in high yields through a domino reaction (imine formation and subsequent aza-Diels-Alder reaction).

Without the need to carry out a linking or cleavage stage, as with the solid phase formulation, and also without purification of the intermediate stages, as with the described solution chemistry, the process according to the invention is distinguished by its ease of implementation and also by its method of purification. Products of high purity can for the most part be obtained by repeated washing with non-polar solvents, for example n-hexane. Otherwise, they may be purified by column chromatography. In particular, pure diastereomer compounds of Formula I may be obtained by washing with non-polar solvents, for example n-hexane, or by crystallization of their salts, for example the hydrochlorides.

Most reagents used here, in particular of Formulae I, III and IV, are commercially available or may be prepared by synthesis methods well-known to a person ordinarily skilled in the art.

After the basic process, the products formed during the basic process may be reacted in subsequent reactions by procedures well-known to a person ordinarily skilled in the art to form secondary products of Formula I, the hydrogen initially being substituted at $R^4$.

Thus, if the product is to be substituted 1,2,3,4-tetrahydroquinoline-2-carboxylic acid derivatives of Formula I wherein $R^4$=alkyl, formyl, acyl, sulphenyl and sulphonyl, the reaction product after completion of the basic reaction may be reacted with corresponding chloro- or fluoroformiates, acid chlorides, sulphenyl chlorides and sulphonyl chlorides in the presence of a base, preferably triethyl amine, pyridine or NaOH in water, dioxan and water mixtures or THF and water mixtures at a temperature between 0 and 20° C. (J. Org. Chem. 1989, 54, 5574–5580).

Similarly, if the product is to be substituted 1,2,3,4-tetrahydroquinoline-2-carboxylic acid derivatives of Formula I wherein $R^4$=CSNR$^{17}$, the reaction product after completion of the basic reaction may be reacted with a thionation reagent, preferably Lawesson's reagent (2,4-bis (4-methoxyphenyl)-2,4-dithioxo-1,2,3,4-dithiaphosphetane), in organic solvents, preferably THF or toluene at a temperature of 30 to 50° C.

Or, if the product is to be substituted 1,2,3,4-tetrahydroquinoline-2-carboxylic acid derivatives of Formula I wherein $R^4$=C(O)N$^{13}$R$^{14}$ or C(S)N$^{13}$N$^{14}$, the reactionproduct after completion of the basic reaction may be reacted with potassium cyanate or potassium isothiocyanate in water at temperatures of up to 100° C. or with organic isocyanates or isothiocyanates in alcohols, preferably methanol, ethanol or isopropanol at temperatures up to boiling point.

Furthermore, if the product is to be substituted 1,2,3,4-tetrahydroquinoline-2-carboxylic acid derivatives of Formula I wherein $R^4$=C(NR$^{13}$)NR$^{14}$R$^{15}$, the reaction product after completion of the basic reaction may be reacted under alkaline conditions with O-methylisoureas or S-methylisothio ureas at temperatures of 20 to 50° C., preferably ethanolic or methanolic NaOH or KOH.

Furthermore, if the product is to be substituted 1,2,3,4-tetrahydroquinoline-2-carboxylic acid derivatives of Formula I wherein $R^4$=C(O)NR$^{13}$R$^{14}$, the reaction product after completion of the basic reaction may be reacted in water/ glacial acetic acid at 30 to 60° C. with propanone-2-semicarbazone.

Similarly, if the product is to be substituted 1,2,3,4-tetrahydroquinoline-2-carboxylic acid derivatives of Formula I wherein $R^4$=C(S)NR$^{13}$R$^{14}$, the reaction product after completion of the basic reaction may be reacted in water/ NaOH at 30 to 60° C. with $CS_2$ and hydrazines.

As the last possibility to be mentioned here, if the product is to be substituted 1,2,3,4-tetrahydroquinoline-2-carboxylic acid derivatives of Formula I wherein $R^4$=alkyl, benzyl or phenethyl, the reaction product on completion of the basic reaction may be reacted with a corresponding alkylation halide, benzyl halide or phenethyl halide and a suitable base, preferably sodium hydride or potassium tert-butylate, in a solvent, for example ethanol, at between 0 and 100° C. (J. Org. Chem. 1947, 12, 760; Zh. Obshch. Khim 1942, 12, 418).

It may also be desirable to use starting products of Formula III in which $R^3 \neq H$ and $R^3$ are preferably alkyl, in particular $CH_3$ and $C_2H_5$ for the basic process for preparing substituted 1,2,3,4-tetrahydroquinoline-2-carboxylic acid derivatives of Formula I wherein $R^3$=H. After the basic process and also the subsequent reactions possibly following it, the reaction product is saponified with a corresponding base, preferably with 6N NaOH in ethanol at temperatures between 0 and 100° C. (Organikum, 1990, p. 418).

Under many of the aforementioned reaction conditions, OH, SH and $NH_2$ groups may possibly enter undesirable secondary reactions. It is therefore preferable to provide them with protective groups or to replace $NH_2$ with $NO_2$ and to eliminate the protective group prior to purification of the end product or to reduce the $NO_2$ group. The invention therefore also relates to a variation of the above-described process in which, in the starting compounds, at least one OH group has been replaced by a OSi(Ph)$_2$tert-butyl group, at least one SH group has been replaced by a S-p-methoxybenzyl group and/or at least one $NH_2$ group has been replaced by a $NO_2$ group and, prior to purification of the end product, at least one, preferably all, OSi(Ph)$_2$tert-butyl group(s) is eliminated with tetrabutyl ammonium fluoride in tetrahydrofuran and/or at least one, preferably all, p-methoxybenzyl group(s) is eliminated with a metal amine, preferably sodium amine and/or at least one, preferably all, $NO_2$ group(s) reduced to $NH_2$.

Furthermore, carboxylic acid or thiocarboxylic acid groups are sometimes unstable under the aforementioned reaction conditions, so it is preferable to use their methyl esters in the reactions and then to saponify the reaction product with KOH solution or NaOH solution in methanol at 40 to 60° C. The invention therefore also relates to a variation of the above-described process in which prior to purification of the end product, a product of the process with at least one C(O)OCH$_3$ and/or C(S)OCH$_3$ group is saponified with KOH solution or NaOH solution in methanol at 40 to 60° C.

The substituted 1,2,3,4-tetrahydroquinoline-2-carboxylic acid derivatives according to the invention are toxicologically safe, so they are suitable as pharmaceutical active ingredient in pharmaceutical compositions.

The invention therefore also relates to a pharmaceutical composition containing, as active ingredient, at least one substituted 1,2,3,4-tetrahydroquinoline-2-carboxylic acid derivative according to the invention of Formula I, also in the form of their racemates, enantiomers, diastereomers, in particular mixtures of their enantiomers or diastereomers or of an individual enantiomer or diastereomer; their bases and/or salts of physiologically acceptable acids, in particular of the hydrochloride salt.

Preferred pharmaceutical compositions are those which contain, as active ingredient, at least one substituted 1,2,3,4-tetrahydroquinoline-2-carboxylic acid derivative according to Formula I, wherein $R^5$, $R^6$ and $R^8$ represent H and $R^7$ represents Cl, or $R^5$ and $R^7$ represent H and $R^6$ and $R^8$ represent Cl.

Particularly preferred pharmaceutical compositions are those which contain at least one of the following substituted 1,2,3,4-tetrahydroquinoline-2-carboxylic acid derivatives according to the invention:

7,9-dichloro-3a,4,5,9b-tetrahydro-3H-cyclopenta[c]quinoline-4-carboxylic acid ethyl ester,
7,9-dichloro-3a,4,5,9b-tetrahydro-3H-cyclopenta[c]quinoline-4-carboxylic acid,
8-chloro-3a,4,5,9b-tetrahydro-3H-cyclopenta[c]quinoline-4-carboxylic acid ethyl ester,
8-chloro-3a,4,5,9b-tetrahydro-3H-cyclo-penta[c]quinoline-4-carboxylic acid,
6-chloro-4-phenyl-1,2,3,4-tetrahydroquinoline-2-carboxylic acid ethyl ester,
2-phenoxy-5,6a,11,11a-tetrahydro-6H-indene[1,2-c]quinoline-6-carboxylic acid ethyl ester,
6-chloro-4-(3-fluorophenyl)-1,2,3,4-tetrahydroquinoline-2-carboxylic acid ethyl ester,
5,7-dichloro-4-(3-fluorophenyl)-1,2,3,4-tetrahydroquinoline-2-carboxylic acid ethyl ester,
6-chloro-7-trifluoromethyl-4-(2,4,6-trimethylphenyl)-1,2,3,4-tetrahydroquinoline-2-carboxylic acid,
4-(2-hydroxy-ethoxy)-6-trifluoromethoxy-1,2,3,4-tetrahydroquinoline-2-carboxylic acid,
5,7-dichloro-4-naphthalene-2-yl-1,2,3,4-tetrahydroquinoline-2-carboxylic acid ethyl ester,
1,3-dichloro-5,6,6a,7,8,12b-hexahydrobenzo[k]phenanthridine-6-carboxylic acid ethyl ester,
6-iodo-4-(4-methoxyphenyl)-3-methyl-1,2,3,4-tetrahydroquinoline-2-carboxylic acid,
5,7-dichloro-4-phenyl-1,2,3,4-tetrahydroquinoline-2-carboxylic acid ethyl ester,
5,7-dichloro-4-phenyl-1,2,3,4-tetrahydroquinoline-2-carboxylic acid,
5,7-dichloro-4-o-tolyl-1,2,3,4-tetrahydroquinoline-2-carboxylic acid ethyl ester,
5,7-dichloro-4-m-tolyl-1,2,3,4-tetrahydroquinoline-2-carboxylic acid ester,
5,7-dichloro-4-m-tolyl-1,2,3,4-tetrahydroquinoline-2-carboxylic acid,
5,7-dichloro-4-p-tolyl-1,2,3,4-tetrahydroquinoline-2-carboxylic acid ethyl ester,
5,7-dichloro-4-p-tolyl-1,2,3,4-tetrahydroquinoline-2-carboxylic acid,
5,7-dichloro-4-(2,4-dimethylphenyl)-1,2,3,4-tetrahydroquinoline-2-carboxylic acid ethyl ester,
5,7-dichloro-4-(2,4-dimethylphenyl)-1,2,3,4-tetrahydroquinoline-2-carboxylic acid,
5,7-dichloro-4-(2,5-dimethylphenyl)-1,2,3,4-tetrahydroquinoline-2-carboxylic acid ethyl ester,
5,7-dichloro-4-(3,5-dimethylphenyl)-1,2,3,4-tetrahydroquinoline-2-carboxylic acid ethyl ester,
4-(4-tert-butylphenyl)-5,7-dichloro-1,2,3,4-tetrahydroquinoline-2-carboxylic acid ethyl ester,
5,7-dichloro-4-(2-fluorophenyl)-1,2,3,4-tetrahydroquinoline-2-carboxylic acid ethyl ester,
5,7-dichloro-4-(2-fluorophenyl)-1,2,3,4-tetrahydroquinoline-2-carboxylic acid,
5,7-dichloro-4-(3-fluorophenyl)-1,2,3,4-tetrahydroquinoline-2-carboxylic acid ethyl ester,
5,7-dichloro-4-(3-fluorophenyl)-1,2,3,4-tetrahydroquinoline-2-carboxylic acid,
5,7-dichloro-4-(4-fluorophenyl)-1,2,3,4-tetrahydroquinoline-2-carboxylic acid ethyl ester,
5,7-dichloro-4-(4-fluorophenyl)-1,2,3,4-tetrahydroquinoline-2-carboxylic acid,
5,7-dichloro-4-(2-chlorophenyl)-1,2,3,4-tetrahydroquinoline-2-carboxylic acid,
5,7-dichloro-4-(2-chlorophenyl)-1,2,3,4-tetrahydroquinoline-2-carboxylic acid ethyl ester,
5,7-dichloro-4-(3-chlorophenyl)-1,2,3,4-tetrahydroquinoline-2-carboxylic acid ethyl ester,
5,7-dichloro-4-(4-chlorophenyl)-1,2,3,4-tetrahydroquinoline-2-carboxylic acid,
5,7-dichloro-4-(2-bromophenyl)-1,2,3,4-tetrahydroquinoline-2-carboxylic acid ethyl ester,
5,7-dichloro-4-(3-bromophenyl)-1,2,3,4-tetrahydroquinoline-2-carboxylic acid ethyl ester,
5,7-dichloro-4-(3-bromophenyl)-1,2,3,4-tetrahydroquinoline-2-carboxylic acid,
5,7-dichloro-4-(4-bromophenyl)-1,2,3,4-tetrahydroquinoline-2-carboxylic acid ethyl ester,
5,7-dichloro-4-(4-bromophenyl)-1,2,3,4-tetrahydroquinoline-2-carboxylic acid,
5,7-dichloro-4-(3-trifluoromethylphenyl)-1,2,3,4-tetrahydroquinoline-2-carboxylic acid ethyl ester,
5,7-dichloro-3-methyl-4-phenyl-1,2,3,4-tetrahydroquinoline-2-carboxylic acid ethyl ester,
5,7-dichloro-4-(4-methoxyphenyl)-3-phenyl-1,2,3,4-tetrahydroquinoline-2-carboxylic acid ethyl ester,
5,7-dichloro-3,4-bis(4-methoxyphenyl)-3-methyl-1,2,3,4-tetrahydroquinoline-2-carboxylic acid ethyl ester,
5,7-dichloro-4-(4-methoxyphenyl)-3-methyl-1,2,3,4-tetrahydroquinoline-2-carboxylic acid ethyl ester,
5,7-dichloro-4-(3,4-methoxyphenyl)-3-methyl-1,2,3,4-tetrahydroquinoline-2-carboxylic acid ethyl ester,
5,7-dichloro-3-methyl-4-(2,4,5-trimethoxyphenyl)-1,2,3,4-tetrahydroquinoline-2-carboxylic acid ethyl ester,
6-chloro-4-o-tolyl-1,2,3,4-tetrahydroquinoline-2-carboxylic acid ethyl ester,
6-chloro-4-(2,4,6-trimethylphenyl)-1,2,3,4-tetrahydroquinoline-2-carboxylic acid ethyl ester,
6-chloro-4-(3-fluorophenyl)-1,2,3,4-tetrahydroquinoline-2-carboxylic acid ethyl ester,
6-chloro-4-(4-fluorophenyl)-1,2,3,4-tetrahydroquinoline-2-carboxylic acid ethyl ester,
6-chloro-4-(2-chlorophenyl)-1,2,3,4-tetrahydroquinoline-2-carboxylic acid ethyl ester,
6-chloro-4-(4-chlorophenyl)-1,2,3,4-tetrahydroquinoline-2-carboxylic acid ethyl ester,
6-chloro-4-(2-bromophenyl)-1,2,3,4-tetrahydroquinoline-2-carboxylic acid ethyl ester,
6-chloro-4-(3-bromophenyl)-1,2,3,4-tetrahydroquinoline-2-carboxylic acid ethyl ester,
6-chloro-4-(4-bromophenyl)-1,2,3,4-tetrahydroquinoline-2-carboxylic acid ethyl ester,
6-chloro-4-(4-trifluoromethylphenyl)-1,2,3,4-tetrahydroquinoline-2-carboxylic acid ethyl ester,
6-chloro-4-(2-methoxyphenyl)-1,2,3,4-tetrahydroquinoline-2-carboxylic acid ethyl ester,
7,9-dichloro-2,3,3a,4,5,9b-hexahydro-1H-cyclopenta[c]quinoline-4-carboxylic acid ethyl ester,
1,3-dichloro-7,10-methano-5,6,6a,7,8,9,10,10a-octahydrophenanthridine-6-carboxylic acid ethyl ester,
5,6a,7,11b-tetrahydro-6H-indeno-[2,1-c]quinoline-6-carboxylic acid ethyl ester,
10,12-dichloro-6b,7,8,12b-tetrahydro-8-azabenzo[j]fluoroanthrene-7-carboxylic acid ethyl ester,
1,3-dichloro-5,6,6a,11a-tetrahydro-11-oxa-5-aza-benzo[a]fluoroene-6-carboxylic acid ethyl ester, 1,3-dichloro-5,6,6a,11a-tetrahydro-11-thia-5-aza-benzo[a]fluoroene-6-carboxylic acid ethyl ester,
7,8-dichloro-4-(2-chlorophenyl)-1,2,3,4-tetrahydroquinoline-2-carboxylic acid,
6-cyano-4-(2,3,4-trimethoxyphenyl)-1,2,3,4-tetrahydroquinoline-2-carboxylic acid,
6,8,9-trichloro-2,3,3a,4,5,9b-hexahydro-furo[3,2-c]quinoline-4-carboxylic acid,
8-methoxy-4-(4-methoxyphenyl)-3-methyl-1,2,3,4-tetrahydroquinoline-2-carboxylic acid,
5,6,8-trichloro-4-(4-hydroxyphenyl)-3-methyl-1,2,3,4-tetrahydroquinoline-2-carboxylic acid,
4-(3,4-dimethoxyphenyl)-8-iodo-1,2,3,4-tetrahydroquinoline-2-carboxylic acid,
6-iodo-4-(4-methylsulphanylphenyl)-1,2,3,4-tetrahydroquinoline-2-carboxylic acid,
4-(4-ethoxy-3-methoxyphenyl)-6-phenoxy-1,2,3,4-tetrahydroquinoline-2-carboxylic acid,
4-(2-ethoxy-naphthalene-1-yl)-6-iodo-1,2,3,4-tetrahydroquinoline-2-carboxylic acid,
8-chloro-4-(4-propoxyphenyl)-1,2,3,4-tetrahydroquinoline-2-carboxylic acid,
4-(2,4-dimethoxy-3-methylphenyl)-6-phenoxy-1,2,3,4-tetrahydroquinoline-2-carboxylic acid,
2-trifluoromethoxy-5,6,6a,7,8,9,10,11,12,12a-decahydro-5-aza-cycloocta-[a]naphthalene-6-carboxylic acid ethyl ester,
6-sec-butyl-4-(6-chlorobenzo[1,3]dioxol-5-yl)-1,2,3,4-tetrahydroquinoline-2-carboxylic acid ethyl ester,
4-anthracene-9-yl-6-chloro-8-methyl-1,2,3,4-tetrahydroquinoline-2-carboxylic acid,
6-sec-butyl-4-naphthalene-1-yl-1,2,3,4-tetrahydroquinoline-2-carboxylic acid,
4-(4-hydroxyphenyl)-3-methyl-8-phenoxy-1,2,3,4-tetrahydroquinoline-2-carboxylic acid,
8-chloro-6-fluoro-4-naphthalene-2-yl-1,2,3,4-tetrahydroquinoline-2-carboxylic acid,
4-(4-methoxyphenyl)-3-methyl-6-phenoxy-1,2,3,4-tetrahydroquinoline-2-carboxylic acid,
6-chloro-8-fluoro-4-m-tolyl-1,2,3,4-tetrahydroquinoline-2-carboxylic acid,
8-chloro-6-fluoro-4-m-tolyl-1,2,3,4-tetrahydroquinoline-2-carboxylic acid,
4-(4-bromophenyl)-6-chloro-8-fluoro-1,2,3,4-tetrahydroquinoline-2-carboxylic acid,
7,8-dichloro-4-(2,4-dimethylphenyl)-1,2,3,4-tetrahydroquinoline-2-carboxylic acid,
6-chloro-4-(4-chlorophenyl)-7-trifluoromethyl-1,2,3,4-tetrahydroquinoline-2-carboxylic acid,
2-cyano-5,6a,7,11b-tetrahydro-6H-indeno[2,1-c]quinoline-6-carboxylic acid ethyl ester,
4-(2-chlorophenyl)-6-cyano-1,2,3,4-tetrahydroquinoline-2-carboxylic acid,
6-bromo-8-chloro-3-methyl-4-phenyl-1,2,3,4-tetrahydroquinoline-2-carboxylic acid ethyl ester,
6-bromo-8-chloro-4-(2,4-dimethylphenyl)-1,2,3,4-tetrahydroquinoline-2-carboxylic acid,
6-bromo-4-(2-bromophenyl)-8-chloro-1,2,3,4-tetrahydroquinoline-2-carboxylic acid,
4-(4-hydroxy-3-methoxyphenyl)-3-methyl-6-methylsulphanyl-1,2,3,4-tetrahydroquinoline-2-carboxylic acid,
6-cyano-3,4-bis-(4-methoxyphenyl)-1,2,3,4-tetrahydroquinoline-2-carboxylic acid,
8-chloro-6-fluoro-3,4-bis-(4-methoxyphenyl)-1,2,3,4-tetrahydroquinoline-2-carboxylic acid ethyl ester,
4-(4-benzyloxy-3-methoxyphenyl)-6-tert-butyl-1,2,3,4-tetrahydroquinoline-2-carboxylic acid ethyl ester,
5,7-dichloro-4-(4-chlorophenyl)-1,2,3,4-tetrahydroquinoline-2-carboxylic acid,
5,7-dichloro-4-(3-chlorophenyl)-1,2,3,4-tetrahydroquinoline-2-carboxylic acid,
5,7-dichloro-4-(4-chlorophenyl)-1,2,3,4-tetrahydroquinoline-2-carboxylic acid,
1,3-dichloro-5,6,6a,7,8,12b-hexahydrobenzo[k]phenanthridine-6-carboxylic acid,
1,3-dichloro-5,6a,7,11b-tetrahydro-6H-indeno[2,1-c]quinoline-6-carboxylic acid, and
5,7-dichloro-4-(3,5-dimethyl-phenyl)-1,2,3,4-tetrahydroquinoline-2-carboxylic acid in the form of their racemates, enantiomers, diastereomers, in particular mixtures of their enantiomers or diastereomers or of an individual enantiomer or diastereomer; their bases and/or salts of physiologically acceptable acids, in particular of the hydrochloride salt.

The pharmaceutical compositions according to the invention may be administered in liquid form in the form of injection solutions, droplets or juices, in semi-solid forms in the form of granules, tablets, pellets, patches, capsules, plasters or aerosols and, in addition to at least one substituted tetrahydroquinoline derivative according to the invention, optionally contain, depending on the formulation, excipients, fillers, solvents, diluents, colorants and/or binders. The choice of auxiliary materials and the amounts to be used depend on whether the pharmaceutical composition is to be administered orally, perorally, parenterally, intravenously, intraperitoneally, intradermally, intramuscularly, intranasally, buccally, rectally or topically, for example to infections on the skin, the mucous membranes or the eyes. Preparations in the form of tablets, dragees, capsules, granules, droplets, juices and syrups are suitable for oral administration, solutions, suspensions, readily reconstitutable dry preparations as well as sprays for parenteral, topical and inhalative administration. Substituted tetrahydroquinoline derivatives according to the invention deposited in dissolved form or in a plaster, optionally with addition of agents which promote skin penetration, are preparations which are suitable for percutaneous administration. Orally or percutaneously administered preparations are able to release the substituted tetrahydroquinoline derivatives according to the invention after a delay. The amount of active ingredient to be administered to the patient varies according to the patient's weight, the method of administration, the indication and the severity of the disease. It is normal to administer 2 to 500 mg/kg (active ingredient/body weight) of at least one substituted tetrahydroquinoline derivative according to the invention of Formula I.

Preferably, the substituted 1,2,3,4-tetrahydroquinoline-2-carboxylic acid derivatives according to the invention are used for the treatment of pain, in particular chronic and neuropathic pain, but also migraine, so the invention also relates to the use of at least one substituted 1,2,3,4-tetrahydroquinoline-2-carboxylic acid derivative according to the invention of Formula I in the form of their racemates, enantiomers, or diastereomers, in particular mixtures of their enantiomers or diastereomers or of an individual enantiomer or diastereomer; their bases and/or salts of physiologically acceptable acids, in particular of the hydrochloride salt, for preparing a pharmaceutical composition for the treatment of pain, in particular neuropathic and/or chronic pain and/or for the treatment of migraine.

The affinity at the NMDA receptor has lead to further fields of application as NMDA antagonists are known to have inter alia a neuroprotective activity and can therefore also readily be used for syndromes such as Parkinson's disease and Huntington's chorea, etc., accompanied by neurodegeneration and damage. Further indications for the NMDA antagonists according to the invention include epilepsy, glaucoma, osteoporosis, ototoxicity, withdrawal phenomena following alcohol and/or drug abuse, stroke and associated cerebral ischaemia, cerebral infarcts, cerebral oedema, hypoxia, anoxia and also to be used for anxiolysis and in anaesthesia. Therefore, the invention also relates to the use of at least one substituted 1,2,3,4-tetrahydroquinoline-2-carboxylic acid derivative according to the invention of Formula I also in the form of their racemates; enantiomers, diastereomers, in particular mixtures of their enantiomers or diastereomers or of an individual enantiomer or diastereomer; their bases and/or salts of physiologically acceptable acids, in particular of the hydrochloride salt, for preparing a pharmaceutical composition for the treatment/prophylaxis of/during epilepsy, Parkinson's disease, Huntington's chorea, glaucoma, ototoxicity, withdrawal symptoms following alcohol and/or drug abuse, stroke, cerebral ischaemia, cerebral infarcts, cerebral oedema, hypoxia, anoxia and/or anxiolysis and/or anaesthesia.

It has surprisingly been found that the substituted 1,2,3,4-tetrahydroquinoline-2-carboxylic acid derivatives according to the invention are also very suitable for further indications, in particular for the treatment of urinary incontinence, itching, tinnitus aurium and/or diarrhoea. Therefore, the instant invention also relates to the use of at least one substituted 1,2,3,4-tetrahydroquinoline-2-carboxylic acid derivative of Formula I, also in the form of their racemates; enantiomers, diastereomers, in particular mixtures of their enantiomers or diastereomers or of an individual enantiomer or diastereomer; their bases and/or salts of physiologically acceptable acids, in particular of the hydrochloride salt, for preparing a pharmaceutical composition for the treatment of urinary incontinence, itching, tinnitus aurium and/or diarrhoea.

However, the compounds according to the invention are also effective in other indications. Therefore, the invention also relates to the use of at least one substituted 1,2,3,4-tetrahydroquinoline-2-carboxylic acid derivative of Formula I, also in the form of their racemates; enantiomers, diastereomers, in particular mixtures of their enantiomers or diastereomers or of an individual enantiomer or diastereomer; their bases and/or salts of physiologically acceptable acids, in particular of the hydrochloride salt, for preparing a pharmaceutical composition for the treatment/prophylaxis of/during schizophrenia, Alzheimer's disease, psychoses caused by a raised amino acid level, AIDS dementia, encephalomyelitis, Gilles de La Tourette's syndrome, perinatal asphyxia, inflammatory and allergic reactions, depression, drug and/or alcohol abuse, gastritis, diabetes, cardiovascular diseases, respiratory tract diseases, coughs and/or mental illnesses.

The invention also relates to a method for treating a non-human mammal or a human requiring treatment of medically relevant symptoms by administration of a therapeutically effective dose of a substituted 1,2,3,4-tetrahydroquinoline-2-carboxylic acid derivative according to the invention of Formula 1, also in the form of its racemates; enantiomers, diastereomers, in particular mixtures of its enantiomers or diastereomers or of an individual enantiomer or diastereomer; its bases and/or salts of physiologically acceptable acids, in particular of the hydrochloride salt, or of a pharmaceutical composition according to the invention. The invention relates, in particular, to corresponding processes for the treatment of pain, in particular neuropathic and/or chronic pain and/or for the treatment of migraine, for the treatment of urinary incontinence, itching, tinnitus aurium and/or diarrhoea, for the treatment/prophylaxis of/during epilepsy, Parkinson's disease, Huntington's chorea, glaucoma, osteoporosis, ototoxicity, withdrawal symptoms following alcohol and/or drug abuse, stroke, cerebral ischaemia, cerebral infarcts, cerebral oedema, hypoxia, anoxia and/or anxiolysis and/or anaesthesia or for the treatment/prophylaxis of/during schizophrenia, Alzheimer's disease, psychoses caused by a raised amino acid level, AIDS dementia, encephalomyelitis, Gilles de La Tourette's syndrome, perinatal asphyxia, inflammatory and allergic reactions, depression, drug and/or alcohol abuse, gastritis, diabetes, cardiovascular diseases, respiratory tract diseases, coughs and/or mental illnesses.

The invention will be described hereafter by examples and figures, without being restricted thereto.

FIGURES

FIG. 1 depicts the effect of compound 2 according to the invention on the dosage/response curve of glycine on RNA-injected oocytes. Relative amplitude: current amplitude, standardized to the response after administration of NMDA/glycine (100/10 $\mu$mol/l).

EXAMPLES

The following examples show compounds according to the invention, the preparation thereof and investigations of response to them.

The following details generally apply:

The chemicals and solvents used have been obtained commercially from traditional suppliers (Acros, Avocado, Aldrich, Fluka, Lancaster, Maybridge, Merck, Sigma, TCI etc., or synthesized using methods well-known to those ordinarily skilled in the art).

Thin-layer chromatography was carried out using HPTLC chromatoplates, silica 60 F 254, made by E. Merck, Darmstadt, Germany.

The yields of compounds produced have not been optimized.

The materials were analyzed by ESI mass spectroscopy.

The compounds are numbered, the detail in brackets basically corresponding to the number of the associated compound.

Example 0

Basic Process a) One equivalent of aniline derivative and trifluoroacetic acid respectively were dissolved in 6 ml/mmol acetonitrile at ambient temperature while stirring, and 1.1 equivalent of ethylglyoxalate (50% in toluene) and 1.1 equivalent of glyoxalic acid monohydrate were then added. 3 equivalents of the olefin component were added after 10 minutes, and the progress of the reaction followed by thin-layer chromatography (1:1 diethyl ether/hexane eluant system). The reaction was terminated after 2 hours (TLC control). The reaction mixture was reacted with an excess of saturated aqueous sodium hydrogen carbonate solution, and the organic phase extracted three times with diethyl ether. The organic phase was washed neutral with water, dried over magnesium sulphate, filtered off, washed with diethyl ether and isolated after concentration by pre-crystallization or silica chromatography.

The 1,2,3,4-tetrahydroquinoline-2-carboxylic acid ester was characterized using an ESI mass spectrometer.

b) Optional subsequent preparation of the free 1,2,3,4-tetrahydroquinoline-2-carboxylic acids The previously described 1,2,3,4-tetrahydroquinoline-2-carboxylic acid ester (1 equivalent) was dissolved in 4 ml/mmol ethanol and reacted with 1.2 equivalents of aqueous 6N sodium hydroxide solution at ambient temperature while stirring. The progress of ester saponification was followed by thin-layer chromatography (1:1 diethyl ether/hexane eluant system) and was terminated after 30 minutes (TLC control). The reaction mixture was concentrated to a small value on a rotary evaporator, taken up in about 10 ml of water and adjusted to pH 1 with 32% HCl. The aqueous solution was extracted 5 times with diethyl ether and concentrated to a small volume over magnesium sulphate after drying.

Automated Process

A round-bottomed glass tube (diameter 16 mm, length 125 mm) with a screw thread was provided with a stirrer and sealed with a screw cap with a septum. The tube was placed in the stirrer block maintained at a temperature of 20° C. The following reagents were then added in succession using a pipette:

1 ml of a solution of trifluoroascetic acid, 0.1 M, and aniline component 0.1 M, in acetonitrile;

1 ml of a 0.11 M solution of the aldehyde in acetonitrile; and 1 ml of a 0.3 M solution of the olefin in acetonitrole.

The reaction mixture was stirred for 10 h at 20° C. in one of the stirrer blocks. The reaction solution was then filtered off. The tube was flushed twice with 1.5 ml of a 7.5% NaHCO$_3$ solution.

The reaction mixture was reacted with 2 ml of ethyl acetate on a vortexer and shaken. It was centrifuged briefly in the centrifuge to form the phase boundary. The phase boundary was detected optically and the organic phase pipetted off. In the next stage, the aqueous phase was reacted again with 2 ml of ethyl acetate, shaken, centrifuged and the organic phase pipetted off. The combined organic phases were dried over 2.4 g of MgSO$_4$ (granulated). The solvent was removed in a vacuum centrifuge.

The free 1,2,3,4-tetrahydroquinoline-2-carboxylic acid was characterized using an ESI mass spectrometer.

Example 1

7,9-dichloro-3a,4,5,9b-tetrahydro-3H-cyclopenta[c]quinoline-4-carboxylic Acid Ethyl Ester (1)

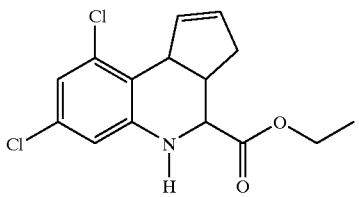

Compound 1 was prepared in a yield of 89% by the basic process from 5.0 mmol 3,5-dichloroaniline, 5.5 mmol ethylglyoxalate solution (50% toluene), 15.0 mmol cyclopentadiene and 5.0 mmol trifluoroacetic acid in 30.0 ml acetonitrile.

An ESI mass spectrometer was used for characterization: MS(EI)m/z: 311 (M*).

Example 2

7,9-dichloro-3a,4,5,9b-tetrahydro-3H-cyclopenta[c]quinoline-4-carboxylic Acid (2)

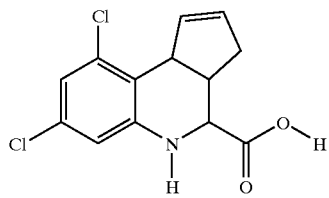

Compound 1 was saponified with 1.0 ml sodium hydroxide solution (6N, water) in 20.0 ml ethanol. The ethanolic solution was concentrated to small volume on a rotary evaporator, the residue was taken up in water, reacted with 6N HCl and the aqueous solution extracted three times over ether. The organic phase was washed neutral with water, dried over magnesium sulphate and concentrated to a reduced volume on a rotary evaporator.

An ESI mass spectrometer was used for characterization: MS(EI)m/z: 284(M*).

Example 3

8-chloro-3a,4,5,9b-tetrahydro-3H-cyclopenta[c]quinoline-4-carboxylic Acid Ethyl Ester (3)

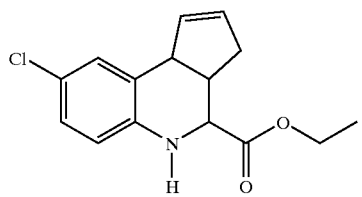

Compound 3 was prepared in a yield of 89% by the basic process from 5.0 mmol 4-chloroaniline, 5.5 mmol ethylglyoxalate solution (50% toluene), 15.0 mmol cyclopentadiene and 5.0 mmol trifluoroacetic acid in 30.0 ml acetonitrile.

An ESI mass spectrometer was used for characterization: MS(EI)m/z: 278(M*).

Example 4

8-chloro-3a-4,5,9b-tetrahydro-3H-cyclo-penta[c]quinoline-4-carboxylic Acid (4) (4)

(4)

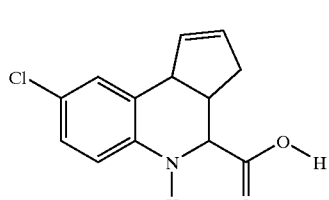

Compound 3 was saponified with 1.0 ml sodium hydroxide solution (6N, water) in 20.0 ml ethanol. The ethanolic solution was concentrated to reduced volume on a rotary evaporator, the residue was taken up in water, reacted with 6N HCl and the aqueous solution extracted three times over ether. The organic phase was washed neutral with water, dried over magnesium sulphate and concentrated to a reduced volume on the rotary evaporator.

An ESI mass spectrometer was used for characterization: MS(EI)m/z: 250(M*).

Example 5

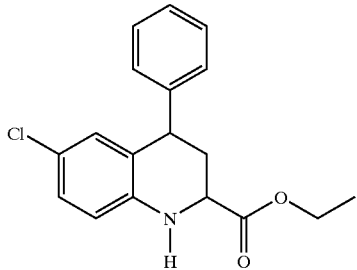

6-chloro-4-phenyl-1,2,3,4-tetrahydroquinoline-2-carboxylic Acid Ethyl Ester (5)

Compound 5 was prepared in a yield of 94% by the basic process from 5.0 mmol 4-chloroaniline, 5.5 mmol ethylglyoxalate solution (50% toluene), 15.0 mmol styrene and 5.0 mmol trifluoroacetic acid in 30.0 ml acetonitrile.

An ESI mass spectrometer was used for characterization: MS(EI)m/z: 315.5(M*).

Example 6

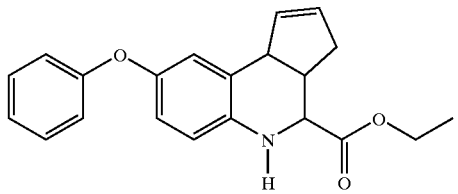

2-phenoxy-5,6a,11,11a-tetrahydro-6H-indene[1,2-c]quinoline-6-carboxylic Acid Ethyl Ester (6)

Compound 6 was prepared in a yield of 72% by the basic process from 5.0 mmol 4-phenoxyaniline, 5.5 mmol ethylglyoxalate solution (50% toluene), 15.0 mmol styrene and 5.0 mmol trifluoroacetic acid in 30.0 ml acetonitrile.

An ESI mass spectrometer was used for characterization: MS(EI)m/z: 385.0(M*).

Example 7

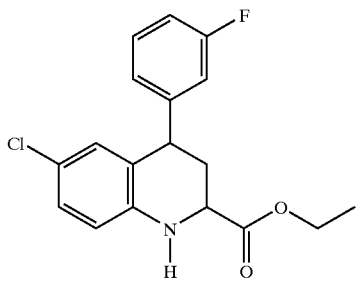

6-chloro-4-(3-fluorophenyl)-1,2,3,4-tetrahydroquinoline-2-carboxylic Acid Ethyl Ester (7)

Compound 7 was prepared in a yield of 66% by the basic process from 5.0 mmol 4-chloroaniline, 5.5 mmol ethyl-glyoxalate solution (50% toluene), 15.0 mmol 3-fluorostyrene and 5.0 mmol trifluoroacetic acid in 30.0 ml acetonitrile.

An ESI mass spectrometer was used for characterization: MS(EI)m/z: 333.0(M*).

Example 8

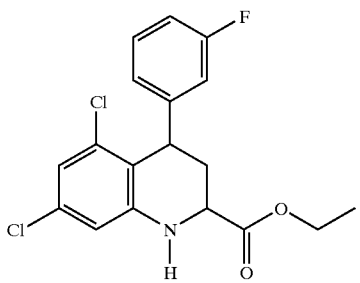

5,7-dichloro-4-(3-fluorophenyl)-1,2,3,4-tetrahydroquinoline-2-carboxylic Acid Ethyl Ester (8)

Compound 8 was prepared in a yield of 44% by the basic process from 5.0 mmol 3,5-dichloroaniline, 5.5 mmol ethylglyoxalate solution (50% toluene), 15.0 mmol 3-fluorostyrene and 5.0 mmol trifluoroacetic acid in 30.0 ml acetonitrile.

An ESI mass spectrometer was used for characterization: MS(EI)m/z: 367.0(M*).

Example 9

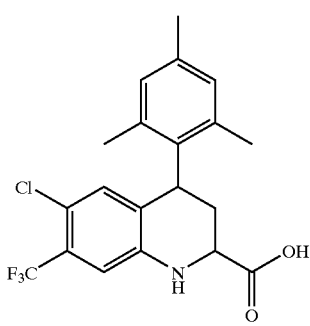

6-chloro-7-trifluoromethyl-4-(2,4,6-trimethylphenyl)-1,2,3,4-tetrahydroquinoline-2-carboxylic Acid (9)

Compound 9 was prepared by the basic process from 5.0 mmol 4-chloro-4-trifluoromethylaniline, 5.5 mmol glyoxalic acid monohydrate and 15.0 mmol 2,4,6-trimethylstyrene in 30 ml of acetonitrile.

An ESI mass spectrometer was used for characterization: MS(EI)m/z: 398.1(M*).

Example 10

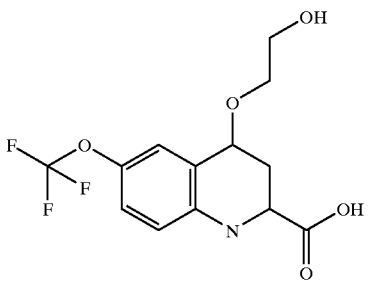

4-(2-hydroxy-ethoxy)-6-trifluoromethoxy-1,2,3,4-tetrahydroquinoline-2-Carboxylic Acid (10)

Compound 10 was prepared from 4-(trifluoromethoxy)-aniline, glyoxylic acid and ethylene glycol monovinyl ether by the automated process.

Example 11

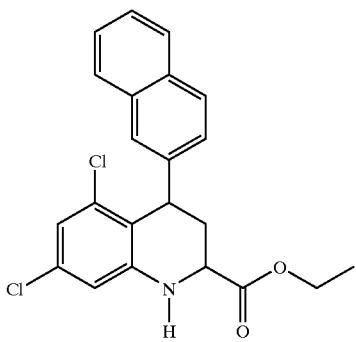

5,7-dichloro-4-naphthalene-2-yl-1,2,3,4-tetrahydroquinoline-2-carboxylic Acid Ethyl Ester (11)

Compound 11 was prepared in a yield of 84% by the basic process from 5.0 mmol 3,5-dichloroaniline, 5.5 mmol ethylglyoxalate solution (50% toluene), 15.0 mmol 2-vinylnaphthalene and 5.0 mmol trifluoroacetic acid in 30.0 ml acetonitrile.

An ESI mass spectrometer was used for characterization: MS(EI)m/z: 399.0(M*).

Example 12

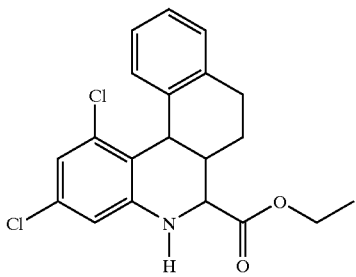

1,3-dichloro-5,6,6a,7,8,12b-hexahydrobenzo[k]phenanthridine-6-carboxylic Acid Ethyl Ester (12)

Compound 12 was prepared in a yield of 85% by the basic process from 5.0 mmol 3,5-dichloroaniline, 5.5 mmol eth-ylglyoxalate solution (50% toluene), 15.0 mmol 1,2-Dihydronaphthalene and 5.0 mmol trifluoroacetic acid in 30.0 ml acetonitrile.

An ESI mass spectrometer was used for characterization:

MS(EI)m/z: 375.0(M*).

Example 13

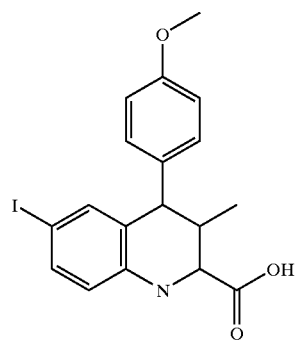

6-iodo-4-(4-methoxyphenyl)-3-methyl-1,2,3,4-tetrahydroquinoline-2-carboxylic Acid (13)

Compound 13 was prepared from 4-iodoaniline, glyoxylic acid and trans-anethole by the automated process.

Example 14

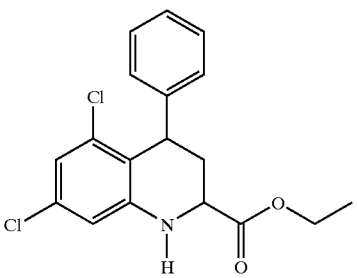

5,7-dichloro-4-phenyl-1,2,3,4-tetrahydroquinoline-2-carboxylic Acid Ethyl Ester (14)

Compound 14 was prepared by the basic process from 5.0 mmol 3,5-dichloroaniline, 5.5 mmol ethylglyoxalate solution (50% toluene), 15.0 mmol styrene and 5.0 mmol trifluoroacetic acid in 30.0 ml acetonitrile.

An ESI mass spectrometer was used for characterization:

MS(EI)m/z: (M*) 349.

Example 15

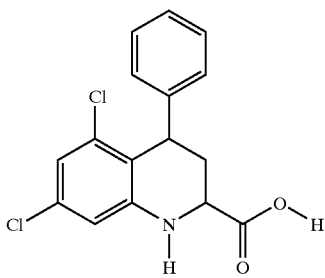

5,7-dichloro-4-phenyl-1,2,3,4-tetrahydroquinoline-2-carboxylic Acid (15)

Compound 15 was prepared by the basic process from 5.0 mmol 3,5-dichloroaniline, 5.5 mmol ethylglyoxalate solution (50% toluene), 15.0 mmol styrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization: MS(EI)m/z: (M*) 315.

Example 16

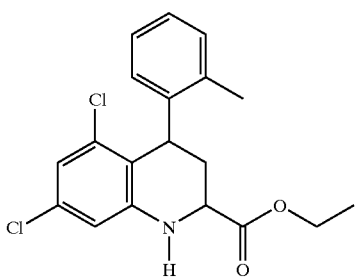

5,7-dichloro-4-o-tolyl-1,2,3,4-tetrahydroquinoline-2-carboxylic Acid Ethyl Ester (16)

Compound 16 was prepared by the basic process from 5.0 mmol 3,5-dichloroaniline, 5.5 mmol ethylglyoxalate solution (50% toluene), 15.0 mmol 2-methylstyrene and 5.0 mmol trifluoroacetic acid in 30.0 ml acetonitrile.

An ESI mass spectrometer was used for characterization: MS(EI)m/z: (M*) 363.

Example 17

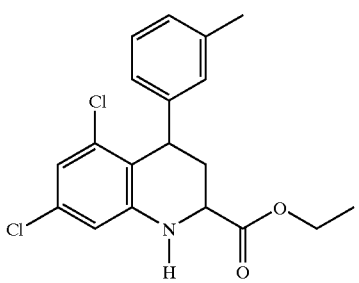

5,7-dichloro-4-m-tolyl-1,2,3,4-tetrahydroquinoline-2-carboxylic Acid Ester (17)

Compound 17 was prepared by the basic process from 5.0 mmol 3,5-dichloroaniline, 5.5 mmol ethylglyoxalate solution (50% toluene), 15.0 mmol 3-methylstyrene and 5.0 mmol trifluoroacetic acid in 30.0 ml acetonitrile.

An ESI mass spectrometer was used for characterization:

MS(EI)m/z: (M*) 363.

Example 18

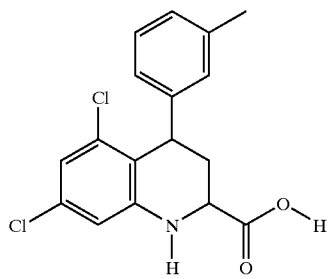

5,7-dichloro-4-m-tolyl-1,2,3,4-tetrahydroquinoline-2-carboxylic Acid (18)

Compound 18 was prepared by the basic process from 5.0 mmol 3,5-dichloroaniline, 5.5 mmol ethylglyoxalate solution (50% toluene), 15.0 mmol 3-methylstyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 335.

Example 19

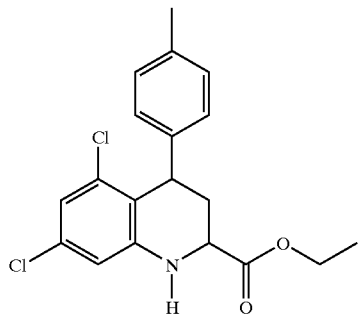

5,7-dichloro-4-p-tolyl-1,2,3,4-tetrahydroquinoline-2-carboxylic Acid Ethyl Ester (19)

Compound 19 was prepared by the basic process from 5.0 mmol 3,5-dichloroaniline, 5.5 mmol ethylglyoxalate solution (50% toluene), 15.0 mmol 4-methylstyrene and 5.0 mmol trifluoroacetic acid in 30.0 ml acetonitrile.

An ESI mass spectrometer was used for characterization:

MS(EI)m/z: (M*) 363.

Example 20

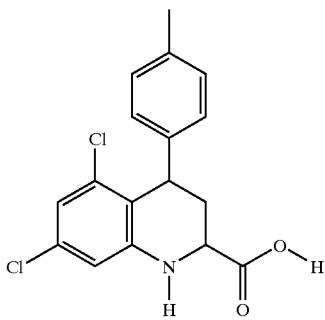

5,7-dichloro-4-p-tolyl-1,2,3,4-tetrahydroquinoline-2-Carboxylic Acid (20)

Compound 20 was prepared by the basic process from 5.0 mmol 3,5-dichloroaniline, 5.5 mmol ethylglyoxalate solution (50% toluene), 15.0 mmol 4-methylstyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 335.

Example 21

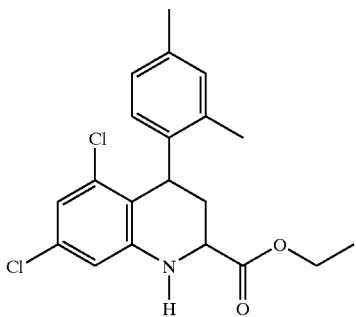

5,7-dichloro-4-(2,4-dimethylphenyl)-1,2,3,4-tetrahydroquinoline-2-carboxylic Acid Ethyl Ester (21)

Compound 21 was prepared by the basic process from 5.0 mmol 3,5-dichloroaniline, 5.5 mmol ethylglyoxalate solution (50% toluene), 15.0 mmol 2,4-dimethylstyrene and 5.0 mmol trifluoroacetic acid in 30.0 ml acetonitrile.

An ESI mass spectrometer was used for characterization:

MS(EI)m/z: (M*) 377.

Example 22

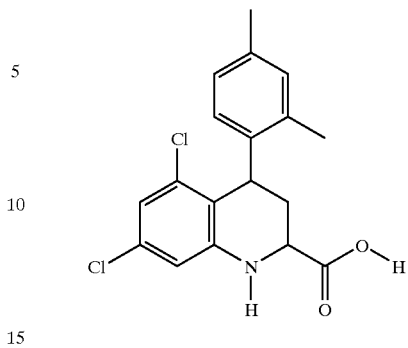

5,7-dichloro-4-(2,4-dimethylphenyl)-1,2,3,4-tetrahydroquinoline-2-carboxylic Acid (22)

Compound 22 was prepared by the basic process from 5.0 mmol 3,5-dichloroaniline, 5.5 mmol ethylglyoxalate solution (50% toluene), 15.0 mmol 2,4-dimethylstyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 349.

Example 23

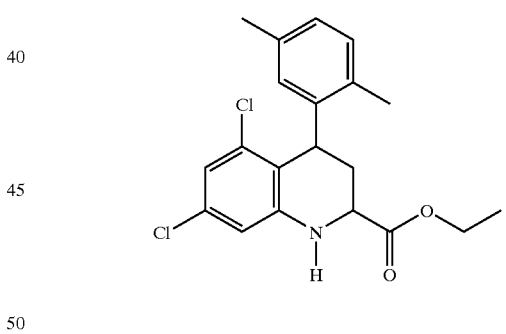

5,7-dichloro-4-(2,5-dimethylphenyl)-1,2,3,4-tetrahydroquinoline-2-carboxylic Acid Ethyl Ester (23)

Compound 23 was prepared in a yield of 89% by the basic process from 5.0 mmol 3,5-dichloroaniline, 5.5 mmol ethylglyoxalate solution (50% toluene), 15.0 mmol 2,5-dimethylstyrene and 5.0 mmol trifluoroacetic acid in 30.0 ml acetonitrile.

An ESI mass spectrometer was used for characterization:

MS(EI)m/z: (M*) 377.

Example 24

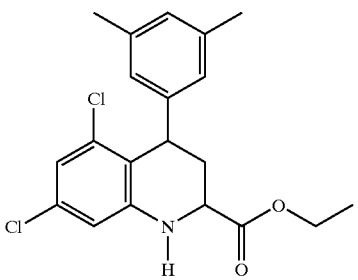

5,7-dichloro-4-(3,5-dimethylphenyl)-1,2,3,4-
tetrahydroquinoline-2-carboxylic Acid Ethyl Ester
(24)

Compound 24 was prepared by the basic process from 5.0 mmol 3,5-dichloroaniline, 5.5 mmol ethylglyoxalate solution (50% toluene), 15.0 mmol 3,5-dimethylstyrene and 5.0 mmol trifluoroacetic acid in 30.0 ml acetonitrile.

An ESI mass spectrometer was used for characterization:

MS(EI)m/z: (M*) 377.

Example 25

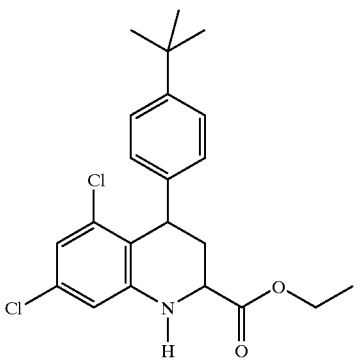

4-(4-tert-butylphenyl)-5,7-dichloro-1,2,3,4-
tetrahydroquinoline-2-carboxylic Acid Ethyl Ester
(25)

Compound 25 was prepared in a yield of 89% by the basic process from 5.0 mmol 3,5-dichloroaniline, 5.5 mmol ethylglyoxalate solution (50% toluene), 15.0 mmol 4-tert-butylstyrene and 5.0 mmol trifluoroacetic acid in 30.0 ml acetonitrile.

An ESI mass spectrometer was used for characterization:

MS(EI)m/z: (M*) 405.

Example 26

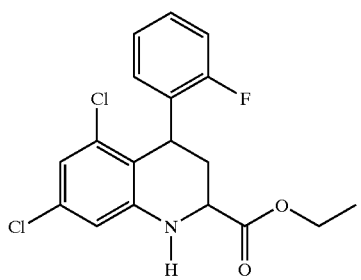

5,7-dichloro-4-(2-fluorophenyl)-1,2,3,4-
tetrahydroquinoline-2-carboxylic Acid Ethyl Ester
(26)

Compound 26 was prepared by the basic process from 5.0 mmol 3,5-dichloroaniline, 5.5 mmol ethylglyoxalate solution (50% toluene), 15.0 mmol 2-fluorostyrene and 5.0 mmol trifluoroacetic acid in 30.0 ml acetonitrile.

An ESI mass spectrometer was used for characterization:
MS(EI)m/z: (M*) 367.

Example 27

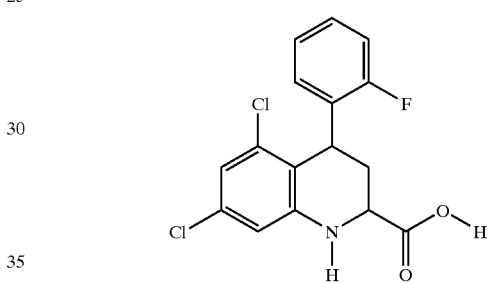

5,7-dichloro-4-(2-fluorophenyl)-1,2,3,4-
tetrahydroquinoline-2-carboxylic Acid (27)

Compound 27 was prepared by the basic process from 5.0 mmol 3,5-dichloroaniline, 5.5 mmol ethylglyoxalate solution (50% toluene), 15.0 mmol 2-fluorostyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:
MS(EI)m/z: (M*) 339.

Example 28

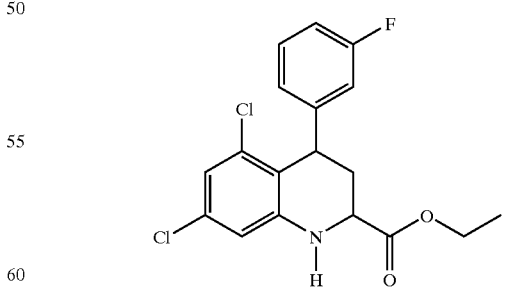

5,7-dichloro-4-(3-fluorophenyl)-1,2,3,4-
tetrahydroquinoline-2-carboxylic Acid Ethyl Ester
(28)

Compound 28 was prepared by the basic process from 5.0 mmol 3,5-dichloroaniline, 5.5 mmol ethylglyoxalate solution (50% toluene), 15.0 mmol 3-fluorostyrene and 5.0 mmol trifluoroacetic acid in 30.0 ml acetonitrile.

An ESI mass spectrometer was used for characterization:

MS(EI)m/z: (M*) 367.

Example 29

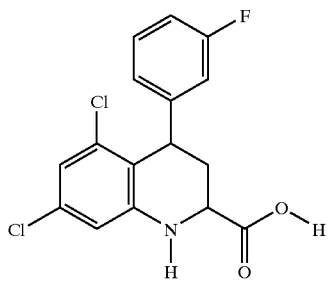

5,7-dichloro-4-(3-fluorophenyl)-1,2,3,4-tetrahydroquinoline-2-carboxylic Acid (29)

Compound 29 was prepared by the basic process from 5.0 mmol 3,5-dichloroaniline, 5.5 mmol ethylglyoxalate solution (50% toluene), 15.0 mmol 3-fluorostyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 340.

Example 30

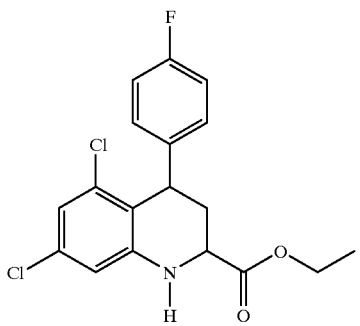

5,7-dichloro-4-(4-fluorophenyl)-1,2,3,4-tetrahydroquinoline-2-carboxylic Acid Ethyl Ester (30)

Compound 30 was prepared by the basic process from 5.0 mmol 3,5-dichloroaniline, 5.5 mmol ethylglyoxalate solution (50% toluene), 15.0 mmol 4-fluorostyrene and 5.0 mmol trifluoroacetic acid in 30.0 ml acetonitrile.

An ESI mass spectrometer was used for characterization:

MS(EI)m/z: (M*) 367.

Example 31

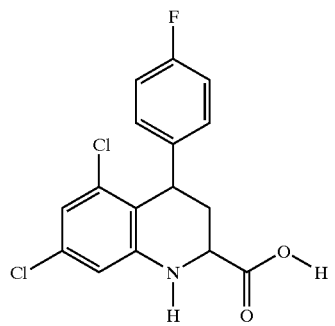

5,7-dichloro-4-(4-fluorophenyl)-1,2,3,4-tetrahydroquinoline-2-carboxylic Acid (31)

Compound 31 was prepared by the basic process from 5.0 mmol 3,5-dichloroaniline, 5.5 mmol ethylglyoxalate solution (50% toluene), 15.0 mmol 4-fluorostyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 340.

Example 32

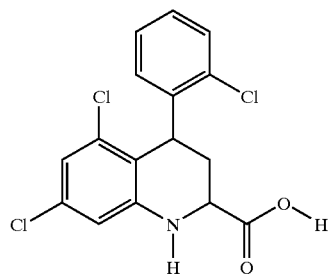

5,7-dichloro-4-(2-chlorophenyl)-1,2,3,4-tetrahydroquinoline-2-carboxylic Acid (32)

Compound 32 was prepared by the basic process from 5.0 mmol 3,5-dichloroaniline, 5.5 mmol ethylglyoxalate solution (50% toluene), 15.0 mmol 2-chlorostyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 356.

Example 33

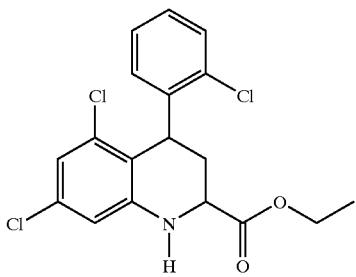

5,7-dichloro-4-(2-chlorophenyl)-1,2,3,4-
tetrahydroquinoline-2-carboxylic Acid Ethyl Ester
(33)

Compound 33 was prepared by the basic process from 5.0 mmol 3,5-dichloroaniline, 5.5 mmol ethylglyoxalate solution (50% toluene), 15.0 mmol 2-chlorostyrene and 5.0 mmol trifluoroacetic acid in 30.0 ml acetonitrile.

An ESI mass spectrometer was used for characterization:

MS(EI)m/z: (M*) 384.

Example 34

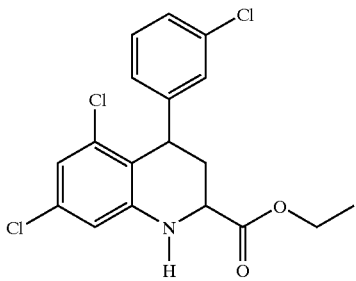

5,7-dichloro-4-(3-chlorophenyl)-1,2,3,4-
tetrahydroquinoline-2-carboxylic Acid Ethyl Ester
(34)

Compound 34 was prepared by the basic process from 5.0 mmol 3,5-dichloroaniline, 5.5 mmol ethylglyoxalate solution (50% toluene), 15.0 mmol 3-chlorostyrene and 5.0 mmol trifluoroacetic acid in 30.0 ml acetonitrile.

An ESI mass spectrometer was used for characterization:

MS(EI)m/z: (M*) 384.

Example 35

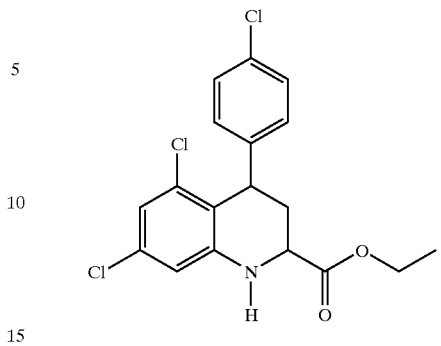

5,7-dichloro-4-(4-chlorophenyl)-1,2,3,4-
tetrahydroquinoline-2-carboxylic Acid Ethyl Ester
(35)

Compound 35 was prepared by the basic process from 5.0 mmol 3,5-dichloroaniline, 5.5 mmol ethylglyoxalate solution (50% toluene), 15.0 mmol 4-chlorostyrene and 5.0 mmol trifluoroacetic acid in 30.0 ml acetonitrile.

An ESI mass spectrometer was used for characterization:

MS(EI)m/z: (M*) 384.

Example 36

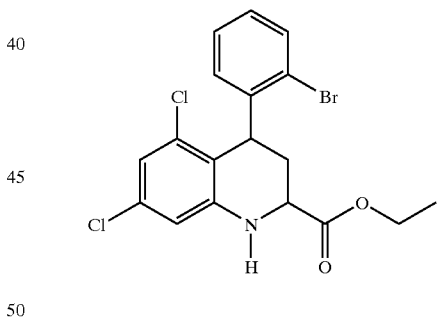

4-(2-bromophenyl)-5,7-dichloro-1,2,3,4-
tetrahydroquinoline-2-carboxylic Acid Ethyl Ester
(36)

Compound 36 was prepared by the basic process from 5.0 mmol 3,5-dichloroaniline, 5.5 mmol ethylglyoxalate solution (50% toluene), 15.0 mmol 2-bromostyrene and 5.0 mmol trifluoroacetic acid in 30.0 ml acetonitrile.

An ESI mass spectrometer was used for characterization:

MS(EI)m/z: (M*) 429.

Example 37

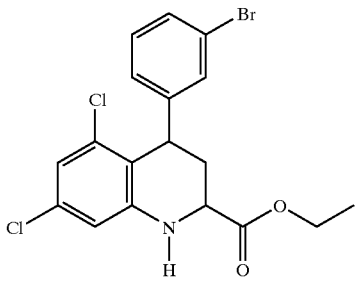

4-(3-bromophenyl)-5,7-dichloro-1,2,3,4-
tetrahydroquinoline-2-carboxylic Acid Ethyl Ester
(37)

Compound 37 was prepared by the basic process from 5.0 mmol 3,5-dichloroaniline, 5.5 mmol ethylglyoxalate solution (50% toluene), 15.0 mmol 3-bromostyrene and 5.0 mmol trifluoroacetic acid in 30.0 ml acetonitrile.

An ESI mass spectrometer was used for characterization:

MS(EI)m/z: (M*) 429.

Example 38

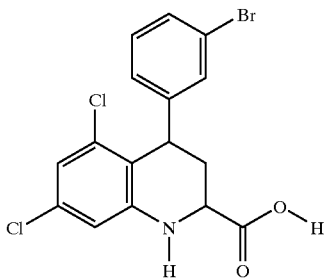

4-(3-bromophenyl)-5,7-dichloro-1,2,3,4-
tetrahydroquinoline-2-carboxylic Acid (38)

Compound 38 was prepared by the basic process from 5.0 mmol 3,5-dichloroaniline, 5.5 mmol ethylglyoxalate solution (50% toluene), 15.0 mmol 3-bromostyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(EI)m/z: (M*) 401.

Example 39

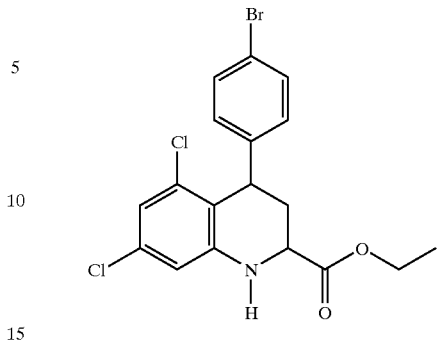

4-(4-bromophenyl)-5,7-dichloro-1,2,3,4-
tetrahydroquinoline-2-carboxylic Acid Ethyl Ester
(39)

Compound 39 was prepared by the basic process from 5.0 mmol 3,5-dichloroaniline, 5.5 mmol ethylglyoxalate solution (50% toluene), 15.0 mmol 4-bromostyrene and 5.0 mmol trifluoroacetic acid in 30.0 ml acetonitrile.

An ESI mass spectrometer was used for characterization:

MS(EI)m/z: (M*) 429.

Example 40

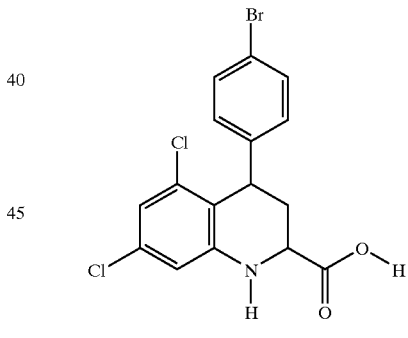

4-(4-bromophenyl)-5,7-dichloro-1,2,3,4-
tetrahydroquinoline-2-carboxylic Acid (40)

Compound 40 was prepared by the basic process from 5.0 mmol 3,5-dichloroaniline, 5.5 mmol ethylglyoxalate solution (50% toluene), 15.0 mmol 4-bromostyrene and 5.0 mmol trifluoroacetic acid in 30.0 ml acetonitrile. Subsequent saponification was carried out using 1.0 ml of sodium hydroxide solution (6N water) in 20.0 ml of ethanol.

An ESI mass spectrometer was used for characterization:

MS(El)m/z: (M*) 401.

Example 41

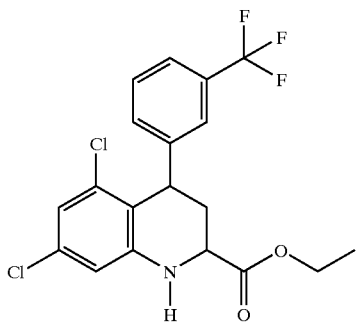

5,7-dichloro-4-(3-trifluoromethylphenyl)-1,2,3,4-tetrahydroquinoline-2-carboxylic Acid Ethyl Ester
(41)

Compound 41 was prepared by the basic process from 5.0 mmol 3,5-dichloroaniline, 5.5 mmol ethylglyoxalate solution (50% toluene), 15.0 mmol 3-trifluoromethylstyrene and 5.0 mmol trifluoroacetic acid in 30.0 ml acetonitrile.

An ESI mass spectrometer was used for characterization:

MS(EI)m/z: (M*) 417.

Example 42

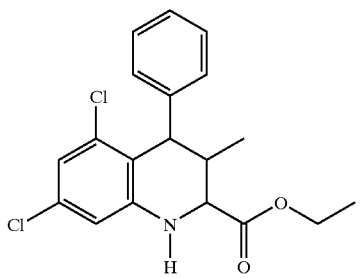

5,7-dichloro-3-methyl-4-phenyl-1,2,3,4-tetrahydroquinoline-2-carboxylic Acid Ethyl Ester
(42)

Compound 42 was prepared by the basic process from 5.0 mmol 3,5-dichloroaniline, 5.5 mmol ethylglyoxalate solution (50% toluene), 15.0 mmol β-methylstyrene and 5.0 mmol trifluoroacetic acid in 30.0 ml acetonitrile.

An ESI mass spectrometer was used for characterization:

MS(EI)m/z: (M*) 363.

Example 43

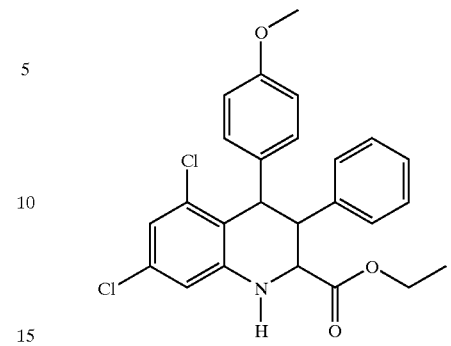

5,7-dichloro-4-(4-methoxyphenyl)-3-phenyl-1,2,3,4-tetrahydroquinoline-2-carboxylic Acid Ethyl Ester
(43)

Compound 43 was prepared by the basic process from 5.0 mmol 3,5-dichloroaniline, 5.5 mmol ethylglyoxalate solution (50% toluene), 15.0 mmol trans-4-methoxystilbene and 5.0 mmol trifluoroacetic acid in 30.0 ml acetonitrile.

An ESI mass spectrometer was used for characterization:

MS(EI)m/z: (M*) 455.

Example 44

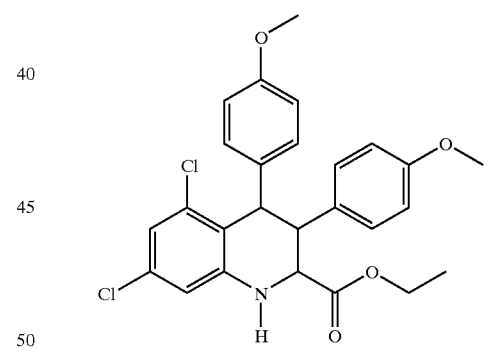

5,7-dichloro-3,4-bis(4-methoxyphenyl)-1,2,3,4-tetrahydroquinoline-2-carboxylic Acid Ethyl ester
(44)

Compound 44 was prepared by the basic process from 5.0 mmol 3,5-dichloroaniline, 5.5 mmol ethylglyoxalate solution (50% toluene), 15.0 mmol trans-4,4'-dimethoxystilbene and 5.0 mmol trifluoroacetic acid in 30.0 ml acetonitrile.

An ESI mass spectrometer was used for characterization:

MS(EI)m/z: (M*) 485.

Example 45

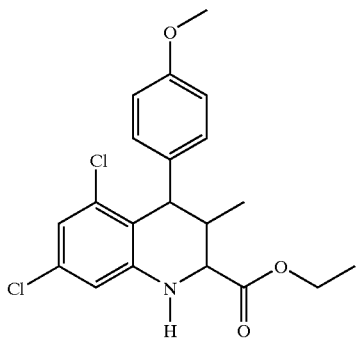

5,7-dichloro-4-(4-methoxyphenyl)-3-methyl-1,2,3,4-tetrahydroquinoline-2-carboxylic Acid Ethyl Ester (45)

Compound 45 was prepared by the basic process from 5.0 mmol 3,5-dichloroaniline, 5.5 mmol ethylglyoxalate solution (50% toluene), 15.0 mmol anethole and 5.0 mmol trifluoroacetic acid in 30.0 ml acetonitrile.

An ESI mass spectrometer was used for characterization:

MS(EI)m/z: (M*) 393.

Example 46

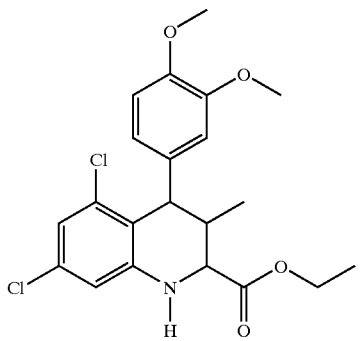

5,7-dichloro-4-(3,4-dimethoxyphenyl)-3-methyl-1,2,3,4-tetrahydroquinoline-2-carboxylic Acid Ethyl Ester (46)

Compound 46 was prepared by the basic process from 5.0 mmol 3,5-dichloroaniline, 5.5 mmol ethylglyoxalate solution (50% toluene), 15.0 mmol 1,2-dimethoxy-4-prop-1-enylbenzene and 5.0 mmol trifluoroacetic acid in 30.0 ml acetonitrile.

An ESI mass spectrometer was used for characterization:

MS(EI)m/z: (M*) 423.

Example 47

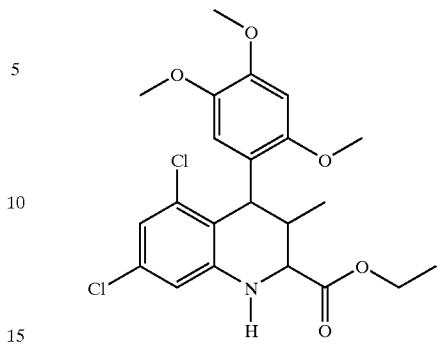

5,7-dichloro-3-methyl-4-(2,4,5-trimethoxyphenyl)-1,2,3,4-tetrahydroquinoline-2-carboxylic Acid Ethyl Ester (47)

Compound 47 was prepared by the basic process from 5.0 mmol 3,5-dichloroaniline, 5.5 mmol ethylglyoxalate solution (50% toluene), 15.0 mmol β-asaron and 5.0 mmol trifluoroacetic acid in 30.0 ml acetonitrile.

An ESI mass spectrometer was used for characterization:

MS(EI)m/z: (M*) 453.

Example 48

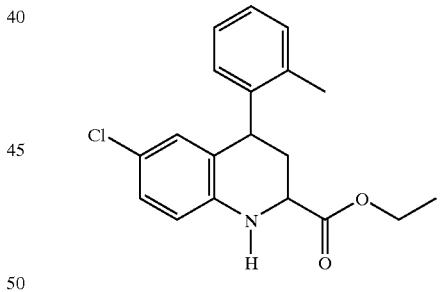

6-chloro-4-o-tolyl-1,2,3,4-tetrahydroquinoline-2-carboxylic Acid Ethyl Ester (48)

Compound 48 was prepared by the basic process from 5.0 mmol 3,5-dichloroaniline, 5.5 mmol ethylglyoxalate solution (50% toluene), 15.0 mmol 2-methylstyrene and 5.0 mmol trifluoroacetic acid in 30.0 ml acetonitrile.

An ESI mass spectrometer was used for characterization:

MS(EI)m/z: (M*) 329.

Example 49

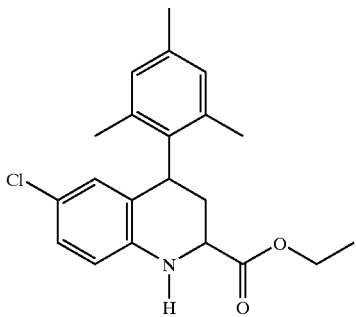

6-chloro-4-(2,4,6-trimethylphenyl)-1,2,3,4-tetrahydroquinoline-2-carboxylic Acid Ethyl Ester
(49)

Compound 49 was prepared by the basic process from 5.0 mmol 4-chloroaniline, 5.5 mmol ethylglyoxalate solution (50% toluene), 15.0 mmol 2,4,6-trimethylstyrene and 5.0 mmol trifluoroacetic acid in 30.0 ml acetonitrile.

An ESI mass spectrometer was used for characterization:

MS(EI)m/z: (M*) 357.

Example 50

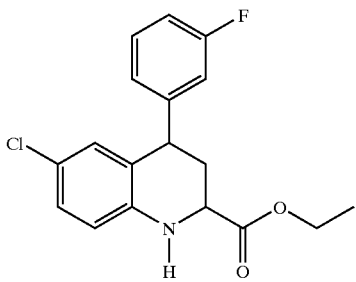

6-chloro-4-(3-fluorophenyl)-1,2,3,4-tetrahydroquinoline-2-carboxylic Acid Ethyl Ester
(50)

Compound 50 was prepared by the basic process from 5.0 mmol 4-chloroaniline, 5.5 mmol ethylglyoxalate solution (50% toluene), 15.0 mmol 3-fluorostyrene and 5.0 mmol trifluoroacetic acid in 30.0 ml acetonitrile.

An ESI mass spectrometer was used for characterization:

MS(EI)m/z: (M*) 333.

Example 51

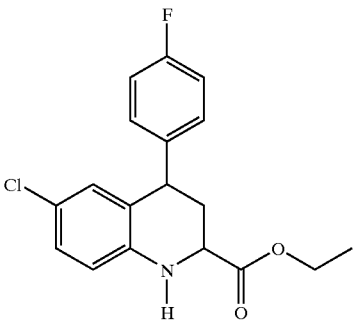

6-chloro-4-(4-fluorophenyl)-1,2,3,4-tetrahydroquinoline-2-carboxylic Acid Ethyl Ester
(51)

Compound 51 was prepared by the basic process from 5.0 mmol 4-chloroaniline, 5.5 mmol ethylglyoxalate solution (50% toluene), 15.0 mmol 4-fluorostyrene and 5.0 mmol trifluoroacetic acid in 30.0 ml acetonitrile.

An ESI mass spectrometer was used for characterization:

MS(EI)m/z: (M*) 333.

Example 52

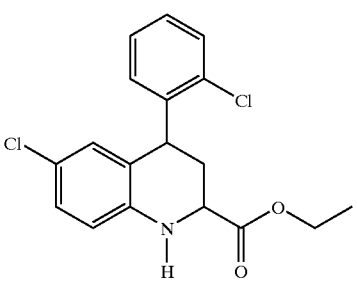

6-chloro-4-(2-chlorophenyl)-1,2,3,4-tetrahydroquinoline-2-carboxylic Acid Ethyl Ester
(52)

Compound 52 was prepared by the basic process from 5.0 mmol 4-chloroaniline, 5.5 mmol ethylglyoxalate solution (50% toluene), 15.0 mmol 2-chlorostyrene and 5.0 mmol trifluoroacetic acid in 30.0 ml acetonitrile.

An ESI mass spectrometer was used for characterization:

MS(EI)m/z: (M*) 383.

Example 53

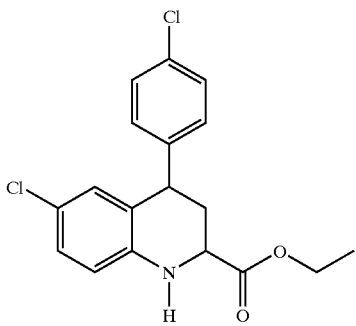

6-chloro-4-(4-chlorophenyl)-1,2,3,4-tetrahydroquinoline-2-carboxylic Acid Ethyl Ester
(53)

Compound 53 was prepared by the basic process from 5.0 mmol 4-chloroaniline, 5.5 mmol ethylglyoxalate solution (50% toluene), 15.0 mmol 4-chlorostyrene and 5.0 mmol trifluoroacetic acid in 30.0 ml acetonitrile.

An ESI mass spectrometer was used for characterization:

MS(EI)m/z: (M*) 383.

Example 54

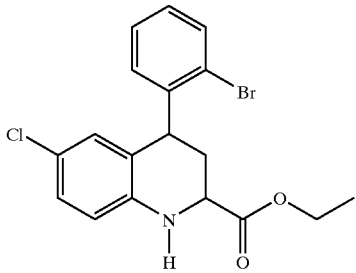

6-chloro-4-(2-bromophenyl)-1,2,3,4-tetrahydroquinoline-2-carboxylic Acid Ethyl Ester
(54)

Compound 54 was prepared by the basic process from 5.0 mmol 4-chloroaniline, 5.5 mmol ethylglyoxalate solution (50% toluene), 15.0 mmol 2-bromostyrene and 5.0 mmol trifluoroacetic acid in 30.0 ml acetonitrile.

An ESI mass spectrometer was used for characterization:

MS(EI)m/z: (M*) 395.

Example 55

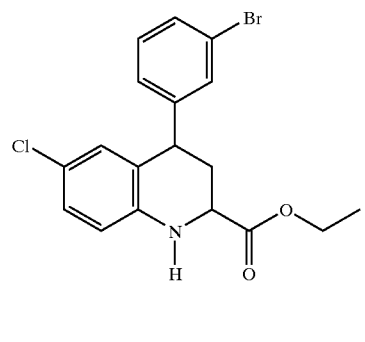

6-chloro-4-(3-bromophenyl)-1,2,3,4-tetrahydroquinoline-2-carboxylic Acid Ethyl Ester
(55)

Compound 55 was prepared by the basic process from 5.0 mmol 4-chloroaniline, 5.5 mmol elhylglyoxalate solution (50% toluene), 15.0 mmol 3-bromostyrene and 5.0 mmol trifluoroacetic acid in 30.0 ml acetonitrile.

An ESI mass spectrometer was used for characterization:

MS(EI)m/z: (M*) 395.

Example 56

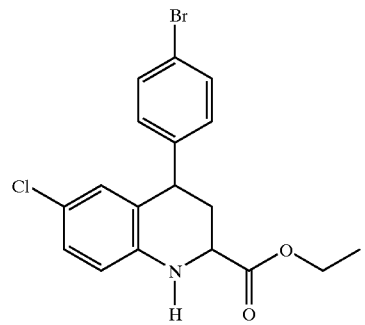

6-chloro-4-(4-bromophenyl)-1,2,3,4-tetrahydroquinoline-2-carboxylic Acid Ethyl Ester
(56)

Compound 56 was prepared by the basic process from 5.0 mmol 4-chloroaniline, 5.5 mmol ethylglyoxalate solution (50% toluene), 15.0 mmol 4-bromostyrene and 5.0 mmol trifluoroacetic acid in 30.0 ml acetonitrile.

An ESI mass spectrometer was used for characterization:

MS(EI)m/z: (M*) 395.

Example 57

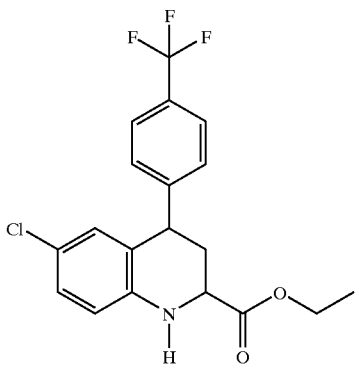

6-chloro-4-(4-trifluoromethylphenyl)-1,2,3,4-tetrahydroquinoline-2-carboxylic Acid Ethyl Ester (57)

Compound 57 was prepared by the basic process from 5.0 mmol 4-chloroaniline, 5.5 mmol ethylglyoxalate solution (50% toluene), 15.0 mmol 4-triflurormethylstyrene and 5.0 mmol trifluoroacetic acid in 30.0 ml acetonitrile.

An ESI mass spectrometer was used for characterization: MS(EI)m/z: (M*) 383.

Example 58

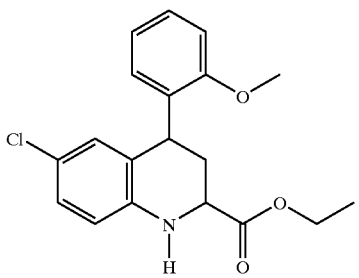

6-chloro-4-(2-methoxyphenyl)-1,2,3,4-tetrahydroquinoline-2-carboxylic Acid Ethyl Ester (58)

Compound 58 was prepared by the basic process from 5.0 mmol 4-chloroaniline, 5.5 mmol ethylglyoxalate solution (50% toluene), 15.0 mmol 2-methoxystyrene and 5.0 mmol trifluoroacetic acid in 30.0 ml acetonitrile.

An ESI mass spectrometer was used for characterization: MS(EI)m/z: (M*) 345.

Example 59

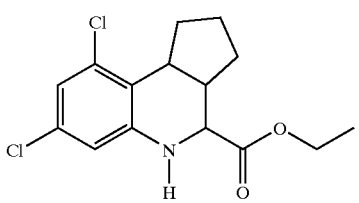

7,9-dichloro-2,3,3a,4,5,9b-hexahydro-1H-cyclopenta[c]quinoline-4-carboxylic Acid Ethyl Ester (59)

Compound 59 was prepared in a yield of 89% by the basic process from 5.0 mmol 3,5-dichloroaniline, 5.5 mmol ethylglyoxalate solution (50% toluene), 15.0 mmol cyclopentene and 5.0 mmol trifluoroacetic acid in 30.0 ml acetonitrile.

An ESI mass spectrometer was used for characterization:

MS(EI)m/z: 313(M*).

Example 60

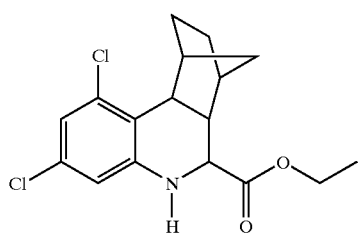

1,3-dichloro-7,10-methano-5,6,6a,7,8,9,10,10a-octahydrophenanthridine-6-carboxylic Acid Ethyl Ester (60)

Compound 60 was prepared in a yield of 89% by the basic process from 5.0 mmol 3,5-dichloroaniline, 5.5 mmol ethylglyoxalate solution (50% toluene), 15.0 mmol bicyclo[2,2,1]hept-2-ene and 5.0 mmol trifluoroacetic acid in 30.0 ml acetonitrile.

An ESI mass spectrometer was used for characterization:

MS(EI)m/z: 339(M*).

Example 61

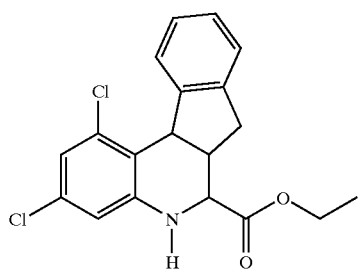

5,6a,7,11b-tetrahydro-6H-indeno-[2, 1-c]quinoline-6-carboxylic Acid Ethyl Ester (61)

Compound 61 was prepared with a yield of 89% by the basic process from 5.0 mmol 3,5-dichloroaniline, 5.5 mmol ethylglyoxalate solution (50% toluene), 15.0 mmol indene and 5.0 mmol trifluoroacetic acid in 30.0 ml acetonitrile.

An ESI mass spectrometer was used for characterization:

MS(EI)m/z: 361 (M*).

Example 62

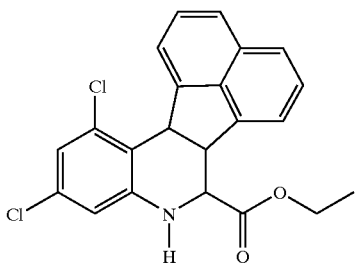

10,12-dichloro-6b,7,8,12b-tetrahydro-8-azabenzo[j]
fluoroanthrene-7-carboxylic Acid Ethyl Ester (62)

Compound 62 was prepared with a yield of 89% by the basic process from 5.0 mmol 3,5-dichloroaniline, 5.5 mmol ethylglyoxalate solution (50% toluene), 15.0 mmol acenaphthene and 5.0 mmol trifluoroacetic acid in 30.0 ml acetonitrile.

An ESI mass spectrometer was used for characterization:
MS(EI)m/z: 397(M*).

Example 63

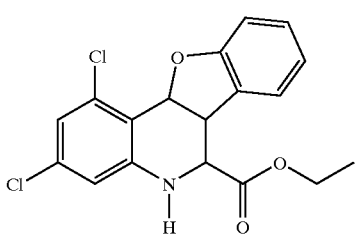

1,3-dichloro-5,6,6a,11-tetrahydro-11-oxa-5-aza-
benzo[a]fluoroene-6-carboxylic Acid Ethyl Ester
(63)

Compound 63 was prepared with a yield of 89% by the basic process from 5.0 mmol 3,5-dichloroaniline, 5.5 mmol ethylglyoxalate solution (50% toluene), 15.0 mmol benzofuran and 5.0 mmol trifluoroacetic acid in 30.0 ml acetonitrile.

An ESI mass spectrometer was used for characterization:
MS(EI)m/z: 363(M*).

Example 64

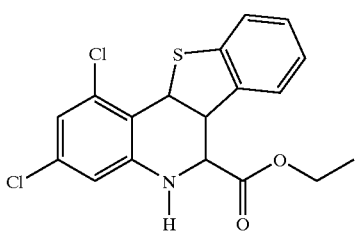

1,3-dichloro-5,6,6a,11a-tetrahydro-11-thia-5-aza-
benzo[a]fluoroene-6-carboxylic Acid Ethyl Ester
(64)

Compound 64 was prepared with a yield of 89% by the basic process from 5.0 mmol 3,5-dichloroaniline, 5.5 mmol ethylglyoxalate solution (50% toluene), 15.0 mmol thianaphthene and 5.0 mmol trifluoroacetic acid in 30.0 ml acetonitrile.

An ESI mass spectrometer was used for characterization:
MS(EI)m/z: 379(M*).

Example 65

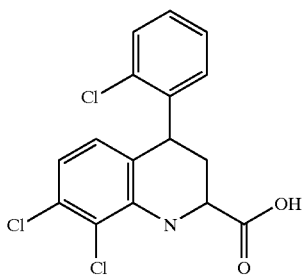

7,8-dichloro-4-(2-chlorophenyl)-1,2,3,4-
tetrahydroquinoline-2-carboxylic Acid (65)

Compound 65 was prepared from 2,3-dichloroaniline, glyoxylic acid and 2-chlorostyrene by the automated process.

Example 66

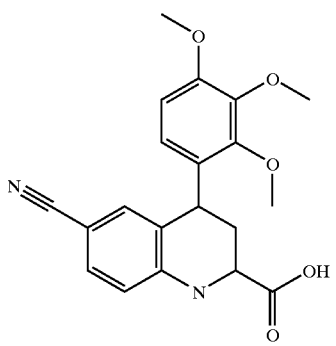

6-cyano-4-(2,3,4-trimethoxyphenyl)-1,2,3,4-
tetrahydroquinoline-2-carboxylic Acid (66)

Compound 66 was prepared from 4-aminobenzonitrile glyoxylic acid and 2,3,4-tetramethoxystyrene by the automated process.

Example 67

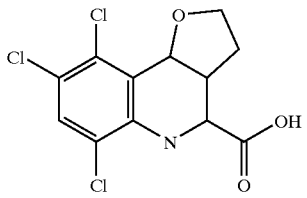

6,8,9-trichloro-2,3,3a,4,5,9b-hexahydro-furo[3,2-c]
quinoline-4-carboxylic Acid (67)

Compound 67 was prepared from 2,4,5-trichloroaniline, glyoxylic acid and 2,3-dihydrofuran by the automated process.

Example 68

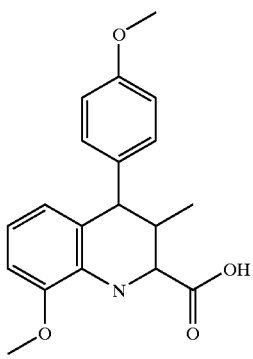

8-methoxy-4-(4-methoxyphenyl)-3-methyl-1,2,3,4-tetrahydroquinoline-2-carboxylic Acid (68)

Compound 68 was prepared from 2-methoxyaniline, glyoxylic acid and trans-anethole by the automated process.

Example 69

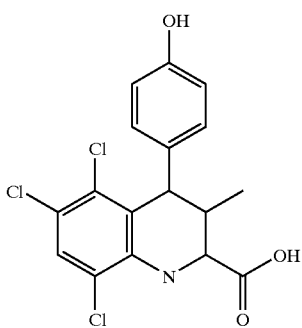

5,6,8-trichloro-4-(4-hydroxyphenyl)-3-methyl-1,2,3,4-tetrahydroquinoline-2-carboxylic Acid (69)

Compound 69 was prepared from 2,3,5-trichloroaniline, glyoxylic acid and 2-propenylphenol by the automated process.

Example 70

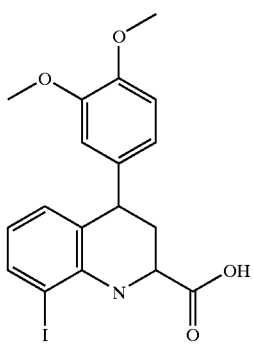

4-(3,4-dimethoxyphenyl)-8-iodo-1,2,3,4-tetrahydroquinoline-2-carboxylic Acid (70)

Compound 70 was prepared from 2-iodoaniline, glyoxylic acid and 3,4-dimethoxystyrene by the automated process.

Example 71

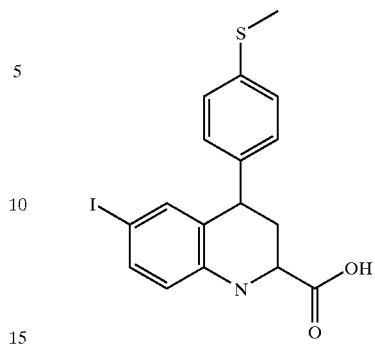

6-iodo-4-(4-methylsulphanylphenyl)-1,2,3,4-tetrahydroquinoline-2-carboxylic Acid (71)

Compound 71 was prepared from 4-iodoaniline, glyoxylic acid and 1-methylsuphanyl-4-vinylbenzene by the automated process.

Example 72

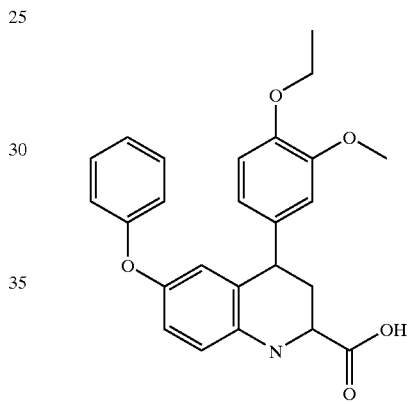

4-(4-ethoxy-3-methoxyphenyl)-6-phenoxy-1,2,3,4-tetrahydroquinoline-2-carboxylic Acid (72)

Compound 72 was prepared from 4-phenoxyaniline, glyoxylic acid and 1-ethoxy-2-methoxy-4-vinylbenzene by the automated process.

Example 73

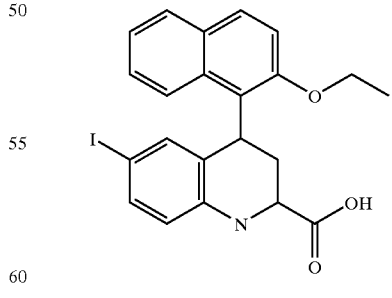

4-(2-ethoxy-naphthalene-1-yl)-6-iodo-1,2,3,4-tetrahydroquinoline-2-carboxylic Acid (73)

Compound 73 was prepared from 4-iodoaniline, glyoxylic acid and 2-ethoxy-1-vinylnaphthalene by the automated process.

Example 74

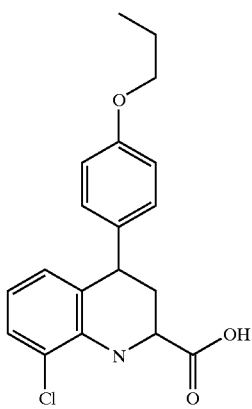

8-chloro-4-(4-propoxyphenyl)-1,2,3,4-tetrahydroquinoline-2-carboxylic Acid (74)

Compound 74 was prepared from 2-chloroaniline, glyoxylic acid and 4-propoxystyrene by the automated process.

Example 75

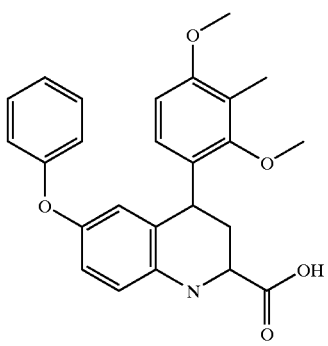

4-(2,4-dimethoxy-3-methylphenyl)-6-phenoxy-1,2,3,4-tetrahydroquinoline-2-carboxylic Acid (75)

Compound 75 was prepared from 4-phenoxyaniline, glyoxylic acid and 2,4-dimethoxy-3-methylstyrene by the automated process.

Example 76

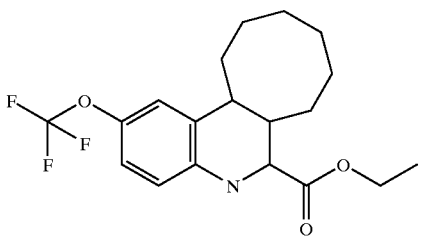

2-trifluoromethoxy-5,6,6a,7,8,9,10,11,12,12a-decahydro-5-aza-cycloocta-[a]naphthalene-6-carboxylic Acid Ethyl Ester (76)

Compound 76 was prepared from 4-(trifluoromethoxy)-aniline, glyoxylic acid ethyl ester and cyclooctene by the automated process.

Example 77

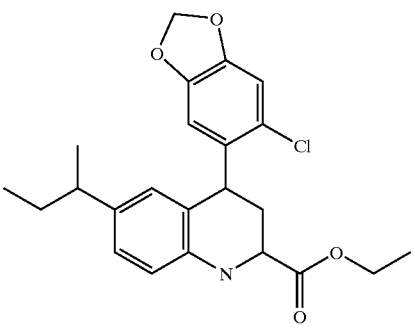

6-sec-butyl-4-(6-chlorobenzo[1,3]dioxol-5-yl)-1,2,3,4-tetrahydroquinoline-2-carboxylic Acid Ethyl Ester (77)

Compound 77 was prepared from 4-sec-butylaniline, glyoxylic acid ethyl ester and 5-chloro-6-vinyl-benzo[1,3]dioxol by the automated process.

Examples 78 to 102 were prepared in a similar manner.

| Example | Name |
|---|---|
| 78 | 4-anthracene-9-yl-6-chloro-8-methyl-1,2,3,4-tetrahydroquinoline-2-carboxylic acid |
| 79 | 6-sec-butyl-4-naphthalene-1-yl-1,2,3,4-tetrahydroquinoline-2-carboxylic acid |
| 80 | 4-(4-hydroxyphenyl)-3-methyl-8-phenoxy-1,2,3,4-tetrahydroquinoline-2-carboxylic acid |
| 81 | 8-chloro-6-fluoro-4-naphthalene-2-yl-1,2,3,4-tetrahydroquinoline-2-carboxylic acid |
| 82 | 4-(4-methoxyphenyl)-3-methyl-6-phenoxy-1,2,3,4-tetrahydroquinoline-2-carboxylic acid |
| 83 | 6-chloro-8-fluoro-4-m-tolyl-1,2,3,4-tetrahydroquinoline-2-carboxylic acid |
| 84 | 8-chloro-6-fluoro-4-m-tolyl-1,2,3,4-tetrahydroquinoline-2-carboxylic acid |
| 85 | 4-(4-bromophenyl)-6-chloro-8-fluoro-1,2,3,4-tetrahydroquinoline-2-carboxylic acid |
| 86 | 7,8-dichloro-4-(2,4-dimethylphenyl)-1,2,3,4-tetrahydroquinoline-2-carboxylic acid |
| 87 | 6-chloro-4-(4-chlorophenyl)-7-trifluoromethyl-1,2,3,4-tetrahydroquinoline-2-carboxylic acid |
| 88 | 2-cyano-5,6a,7,11b-tetrahydro-6H-indeno[2,1-c]quinoline-6-carboxylic acid ethyl ester |
| 89 | 4-(2-chlorophenyl)-6-cyano-1,2,3,4-tetrahydroquinoline-2-carboxylic acid |
| 90 | 6-bromo-8-chloro-3-methyl-4-phenyl-1,2,3,4-tetrahydroquinoline-2-carboxylic acid ethyl ester |
| 91 | 6-bromo-8-chloro-4-(2,4-dimethylphenyl)-1,2,3,4-tetrahydroquinoline-2-carboxylic acid |
| 92 | 6-bromo-4-(2-bromophenyl)-8-chloro-1,2,3,4-tetrahydroquinoline-2-carboxylic acid |
| 93 | 4-(4-hydroxy-3-methoxyphenyl)-3-methyl-6-methylsulphanyl-1,2,3,4-tetrahydroquinoline-2-carboxylic acid |
| 94 | 6-cyano-3,4-bis-(4-methoxyphenyl)-1,2,3,4-tetrahydroquinoline-2-carboxylic acid |
| 95 | 8-chloro-6-fluoro-3,4-bis-(4-methoxyphenyl)-1,2,3,4-tetrahydroquinoline-2-carboxylic acid ethyl ester |
| 96 | 4-(4-benzyloxy-3-methoxyphenyl)-6-tert-butyl-1,2,3,4-tetrahydroquinoline-2-carboxylic acid ethyl ester |
| 97 | 5,7-dichloro-4-(4-chlorophenyl)-1,2,3,4-tetrahydroquinoline-2-carboxylic acid |
| 98 | 5,7-dichloro-4-(3-chlorophenyl)-1,2,3,4-tetrahydroquinoline-2-carboxylic acid |
| 99 | 5,7-dichloro-4-(4-chlorophenyl)-1,2,3,4-tetrahydroquinoline-2-carboxylic acid |
| 100 | 1,3-dichloro-5,6,6a,7,8,12b-hexahydrobenzo[k]phenanthridine-6-carboxylic acid |

-continued

| Example | Name |
|---|---|
| 101 | 1,3-dichloro-5,6a,7,11b-tetrahydro-6H-indeno[2,1-c]quinoline-6-carboxylic acid |
| 102 | 5,7-dichloro-4-(3,5-dimethyl-phenyl)-1,2,3,4-tetrahydroquinoline-2-carboxylic acid |

Example 103
Receptor Binding (Glycine Binding Site of the NMDA Receptor Channel)

Experiments to determine the affinity of the compounds according to the invention of Formula I to the glycine binding site of the NMDA receptor channel were carried out on cerebral membrane homogenates (homogenate of Cortex- and Hippocampus-Areal from the brain of male rats, Wistar strain) (B. M. Baron, B. W. Siegel, B. L. Harrison, R. S. Gross, C. and P. Towers, Journal of Pharmacology and Experimental Therapeutics, Vol. 279, p. 62, 1996).

For this purpose, Cortex and Hippocampus from freshly removed rats' brains were dissected, homogenized in 5 mmol/l TRIS-acetate buffer, 0.32 mol/l sacharose pH 7.4 (10 ml/g fresh weight) with a Potter homogenizer (made by Braun/Melsungen, 10 piston strokes at 500 rpm) while cooling with ice and subsequently centrifuged for 10 minutes at 1,000 g and 4° C. The first supernatant material was collected and the sediment homogenized again with 5 mol/l TRIS-acetate buffer, 0.32 mol/l safcharose pH 7.4 (5 ml/g original fresh weight) using the Potter homogenizer (10 piston strokes at 500 rpm) while cooling with ice and centrifuged for 10 minutes at 1,000 g and 4° C. The resultant supernatant material was combined with the supernatant material from the first centrifugation and centrifuged at 17,000 g for 20 minutes at 4° C. The supernatant material after this centrifugation was discarded, the membrane sediment taken up with 5 mmol/l TRIS-acetate buffer pH 8.0 (20 ml/g original fresh weight) and homogenized with 10 piston strokes at 500 rpm.

The membrane homogenate was then incubated for 1 hour at 4° C. and centrifuged for 30 minutes at 50,000 g and 4° C. The supernatant material was discarded and the centrifuge tube with the membrane sediment sealed with parafilm and frozen for 24 hours at −20° C. The membrane sediment was thawed on the following day, taken up with ice-cold 5 mmol/l TRIS-acetate buffer, 0.1% saponin (w/v) pH 7.0 (10 ml/g original fresh weight), homogenized with 10 piston strokes at 500 rpm and subsequently centrifuged for 20 minutes at 50,00 g and 4° C. The resultant supernatant material was discarded, the sediment taken up in a small volume with 5 mmol/l TRIS-acetate buffer pH 7.0 (about 2 ml/g original fresh weight) and homogenized again with 10 piston strokes at 500 rpm. After determining the protein content, the membrane homogenate was adjusted to a protein concentration of 10 mg protein/ml using 5 mmol/l TRIS-acetate buffer pH 7.0 and frozen in aliquots for testing.

For the receptor binding test, aliquots were thawed, diluted 1:10 with 5 mmol/l TRIS-acetate buffer pH 7.0, homogenized with 10 piston strokes at 500 rpm using the potter homogenizer (10 piston strokes at 500 rpm) while cooling with ice and centrifuged for 60 minutes at 55,000 g at 4° C. The supernatant material was decanted, the membrane sediment adjusted to a protein concentration of 1 mg/ml with ice-cold 50 mmol/l TRIS-acetate buffer pH 7.0, homogenized again with 10 piston strokes at 500 rpm and kept in suspension in the ice bath while stirring on a magnetic stirrer. 100 μl of this membrane homogenate per 1 ml of feedstock was used in each case in the receptor binding test (0.1 mg protein/ml in the final batch).

In the binding test, 50 mmol/l TRIS-acetate buffer pH 7.0 was used as buffer and 1 nmol/l ($^3$H)-MDL 105.519 (B. M. Baron et al 1996) was used as radioactive ligand. The proportion of unspecific binding was determined in the presence of 1 mmol/l glycine.

In further batches, the compounds according to the invention were added in concentration series and the displacement of the radioactive ligand from its specific binding to the glycine binding site of the NMDA receptor channel determined. The respective triple batches were incubated for 120 minutes at 4° C. and then harvested to determine the radioactive ligands bound to the membrane homogenate by filtration through glass fiber filter mats (GF/B). The radioactivity retained on the glass fiber filters was measured in the β counter after addition of scintillator.

The affinity of the compounds according to the invention to the glycine binding site of the NMDA receptor channel was calculated as $IC_{50}$ (concentration with 50% displacement of the radioactive ligand from its specific binding) by the law of mass action by means of non-linear regression and is shown in Table 1 as Ki value (mean from three independent experiments) after conversion (by the Cheng-Prussoff equation) or as a percentage of the previously bound radioactive ligands, see above, which is displaced with a concentration of 10 μmol/l of the test substance according to the invention from its specific binding.

TABLE 1

| | Glycine binding site of the NMDA receptor channel | |
|---|---|---|
| Example | Ki (μmol/l) | Displacement (%, 10 μmol/l) |
| 2 | 0.3 | 100 |
| 14 | — | 38 |
| 15 | — | 75 |
| 16 | — | 35 |
| 17 | — | 21 |
| 18 | — | 51 |
| 19 | — | 26 |
| 20 | — | 61 |
| 21 | — | 26 |
| 22 | — | 68 |
| 26 | — | 43 |
| 27 | — | 75 |
| 28 | — | 35 |
| 29 | — | 78 |
| 30 | — | 32 |
| 31 | — | 58 |
| 32 | — | 92 |
| 33 | — | 40 |
| 34 | — | 32 |
| 35 | — | 32 |
| 36 | — | 46 |
| 38 | — | 72 |
| 40 | — | 70 |
| 41 | — | 38 |
| 42 | — | 21 |
| 51 | — | 21 |
| 52 | — | 22 |
| 54 | — | 22 |
| 59 | | 14 |
| 60 | | 23 |
| 61 | | 15 |
| 81 | | 66 |
| 82 | | 96 |
| 83 | | 93 |
| 84 | | 79 |
| 85 | | 61 |
| 86 | | 33 |
| 87 | | 37 |

TABLE 1-continued

| | Glycine binding site of the NMDA receptor channel | |
|---|---|---|
| Example | Ki ($\mu$mol/l) | Displacement (%, 10 $\mu$mol/l) |
| 88 | | 34 |
| 89 | | 30 |
| 90 | | 46 |
| 91 | | 46 |
| 92 | | 62 |
| 93 | | 44 |
| 94 | | 55 |
| 95 | | 33 |
| 96 | | 29 |
| 97 | | 39 |
| 98 | | 51 |
| 99 | | 43 |
| 100 | | 80 |
| 101 | | 98 |
| 102 | | 61 |

Example 104
NMDA/Glycine-induced Ionic Currents in RNA-injected Xenopus Oocytes The experiment to determine functional changes in the NMDA receptor channel due to the compound according to the invention of Formula I was carried out on oocytes of the South African clawed frog, Xenopus laevis. Neuronal NMDA receptor channels were formed for this purpose after injection of RNA from rats' brain into oocytes and were measured by coapplication of NMDA and glycine-activated ionic currents.

Xenopus oocytes from stages V and VI (Dumont, J. N., Journal of Morphology, Vol. 136, 1972) were micro-injected with total RNA from brain tissue of adult rats (100–130 ng/cell) and kept in the culture medium (composition in mmol/l: 88.0 NaCl, 1.0 KCl, 1.5 CaCl$_2$, 0.8 MgSO$_4$, 2.4 NaHCO$_3$, 5 HEPES, 100 IU/ml penicillin, 100 $\mu$g/ml streptomycin, pH 7.4) for up to 10 days at 20° C. Trans-membranous ionic currents were recorded as in conventional two-electrode voltage clamp technology with a holding potential of −70 mV (P. Bloms-Funke P, M. Madeja, U. Mu$\beta$hoff, E.-J. Speckman, Neuroscience Letters, Vol. 205, p. 115, 1996). The OTC interface and the Cellworks Software were used for recording data and controlling the test apparatus (npi, FRG). The compounds according to the invention were added to a nominal Mg$^{2+}$-free medium (composition in mmol/l: 89.0 NaCl, 1.0 KCl, 1.8 CaCl$_2$, 2.4 NaHCO$_3$, 5 HEPES, pH 7.4) and applied systematically using a concentration clamp (npi, FRG). To test the effects of substances brought about via the glycine B-binding site of the NMDA receptor channel, the glycine dosage/response curve was recorded with and without the respective compound according to the invention. For this purpose, NMDA was applied in a fixed concentration of 100 $\mu$mol/l cumulatively with glycine in increasing concentrations (0–100 $\mu$mol/l). The experiment was subsequently repeated in the same manner with a fixed concentration of the compound according to the invention. The effects of the compound according to the invention (10 $\mu$mol/l) were additionally investigated on ionic currents triggered by AMPA (100 $\mu$mol/l) to estimate the selectivity for NMDA versus AMPA receptor channels. The current amplitudes were standardized to those of the control response to coapplication of NMDA (100 $\mu$mol/l) with glycine (10 $\mu$mol/l). The data was analyzed using Igor-Pro software (Version 3.1, WaveMetrics USA). All results were given as mean value±standard error (SEM) from at least three experiments on different oocytes from at least two frogs. The significance for unpaired measured quantities is determined by the Mann-Whitney U-Test and for paired measured quantities by the Wilcoxon test (Sysstat. SPSS Inc., USA). EC$_{50}$ values are calculated according to the following formula:

$$Y=Y_{min}+(Y_{max}-Y_{min})/(1+(X/EC_{50})^{-p})$$

(Y$_{min}$=minimum test value, Y$_{max}$=maximum test value, Y=relative current amplitude, X=concentration of test substance, p=slope factor). The pA$_2$ value of the compound according to the invention was determined graphically by marker regression during displacement of the glycine dosage/response curve to the right. Concentration ratios were calculated using the EC$_{50}$ values which had been calculated independently for each dosage/response curve.

The displacement of the glycine dosage/response curve to the right is shown in FIG. 1 for Example 2 (relative amplitude: current amplitude, standardized to the response after administration of NMDA/glycine (100/10 $\mu$mol/l)). Results for selected compounds according to the invention and their effects on the glycine dosage/response curve and on AMPA-induced ionic currents have been summarized in Table 2.

TABLE 2

Effects of the compounds according to the invention on ionic currents triggered by NMDA/glycine and by AMPA in RNA-injected oocytes.

| Example No. | NMDA/glycine-induced ionic currents pA$_2$ value of glycine dosage/response curve | AMPA-induced ionic currents Inhibition with 10 $\mu$mol/l of compounds according to the invention |
|---|---|---|
| 2 | 6.40 | 5.4% (n = 2) |

Example 105
Formalin Test, Rat

Experiments to determine the antinociceptive activity of the compounds according to the invention of Formula I were carried out in the formalin test on male rats (Sprague-Dawley, 150–170 g).

In the formalin test, the first (early) phase (0–15 min after formalin injection) was distinguished from the second (late) phase (15–60 min after formalin injection) (D. Dubuisson, S. G. Dennis, Pain 4, 161–174 (1977)). The early phase, as a direct reaction to the formalin injection, represents a model for acute pain while the late phase is considered as a model for persistent (chronic) pain (T. J. Coderre, J. Katz, A. L. Vaccarino, R. Melzack, Pain, Vol. 52, p. 259,1993).

The compounds according to the invention were investigated in the second phase of the formalin test to obtain information about the effects of substances in chronic/inflammatory pain.

A nociceptive reaction was induced in freely moving experimental animals by a single subcutaneous formalin injection (50 $\mu$l, 5%) into the dorsal side of the back right paw, the nociceptive reaction being portrayed by the following behavioral parameters: lifting and holding the respective paw (Score 1), shaking and twitching (Score 2), licking and biting (Score 3). The different behavioral patterns triggered by the formalin injection were recorded continuously by observing the animals in the late phase of the formalin test and were weighted differently in an evaluation. Normal behavior in which the animal loads all four paws uniformly was recorded as score 0. The moment of administration prior to the formalin injection was selected according to the method of administration of the compounds according to the invention (intraperitoneal: 15 min, intravenous: 5 min). The described behavioral patterns (Score 1 to 3) in the animals are reduced and possibly even eliminated after injection of substances which have an antinociceptive effect in the formalin test. A comparisom was made with control animals which had received vehicles (solvents) prior to formalin administration. The nociceptive behavior was calculated as a so-called pain rate (PR). The various behavioral parameters received a different weighting (Factor 0, 1, 2, 3). Calculation took place at partial intervals of 3 min according to the following formula:

$$PR=[(T_0 \times 0)+(T_1 \times 1)+(T_2 \times 2)+(T_3 \times 3)]/180$$

wherein $T_0$, $T_1$, $T_2$ and $T_3$ each correspond to the time in seconds in which the animal exhibited behavioral patterns 0, 1, 2 or 3. Substance and vehicle groups include n=10 animals in each case. The effect of the substance was determined as a percentage change versus control on the basis of the PR calculations. The $ED_{50}$ calculations were made by regression analysis.

All compounds according to the invention tested exhibited medium-pronounced to pronounced inhibition of formalin-induced nociception.

The results of selected experiments in the formalin test on rats are summarized in the following table.

TABLE 3

| Compound | Method of administration | Dosage [mg/kg] | % inhibition of formalin-induced nociception |
|---|---|---|---|
| 1 | i.p. | 21.5 | 88.3 |
| 2 | i.p. | 21.5 | 64.5 |
| 4 | i.v. | 21.5 | 67.1 |
| 26 | i.p. | 21.5 | 82.6 |
| 33 | i.p. | 21.5 | 69.0 |
| 34 | i.p. | 21.5 | 53.1 |
| 35 | i.p. | 21.5 | 21.9 |

Example 106
Parenteral Form of Administration 38.5 g of compound 2 were dissolved in 1 l water for injection purposes at ambient temperature and subsequently adjusted to isotonic conditions by addition of anhydrous glucose for injection purposes.

We claim:

1. A substituted 1,2,3,4-tetrahydroquinoline-2-carboxylic acid derivative of formula I

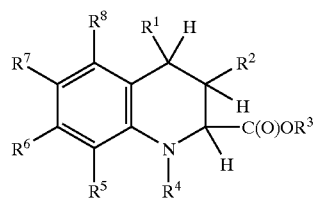

wherein
$R^1$ and $R^2$ together form:
—$(CH_2)_n$— with n=3-10,
—CH=CH—$CH_2$—,
—CH=CH—$CH_2$—$CH_2$—,
—$CH_2$—CH=CH—$CH_2$—,
—$CH_2$—CH=CH—$CH_2$—$CH_2$—,
—$CH_2$—$CH_2$—CH=CH—$CH_2$—$CH_2$—,
—O—$CH_2$—$CH_2$—,
—O—$CH_2$—$CH_2$—$CH_2$—,
—$CH_2$—O—$CH_2$—,
—$CH_2$—$CH_2$—O—$CH_2$—,

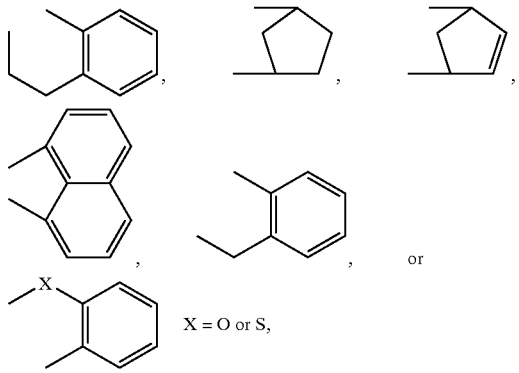

X = O or S, which is singly or multiply substituted or unsubstituted;

$R^3$ is
H; respectively branched or unbranched, singly or multiply substituted or unsubstituted $C_1$–$C_{18}$ alkyl, $C_2$–$C_{18}$ alkenyl or $C_2$–$C_{18}$ alkinyl; saturated or unsaturated, singly or multiply substituted or unsubstituted $C_3$–$C_8$ cycloalkyl, or a corresponding heterocycle, in which at least one carbon atom in the ring is replaced by N, S or O; respectively singly or multiply substituted or unsubstituted alkyl aryl or alkyl heteroaryl; or respectively singly or multiply substituted or unsubstituted aryl or heteroaryl;

$R^4$ is
$R^{4a}$ or $ZR^{4a}$ wherein Z is respectively branched or unbranched, singly or multiply substituted or unsubstituted $C_1$–$C_6$ alkyl, $C_2$–$C_6$ alkenyl or $C_2$–$C_6$ alkinyl, and wherein $R^{4a}$ is
H; respectively branched or unbranched, singly or multiply substituted or unsubstituted $C_1$–$C_{12}$ alkyl, $C_2$–$C_{12}$ alkenyl or $C_2$–$C_{12}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstituted aryl or heteroaryl;
$C(O)R^9$, $C(O)OR^9$, $C(S)R^9$, $C(S)OR^9$ or $SO_2)R^9$, wherein $R^9$ is
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstitued alkyl aryl or alkyl heteroaryl; or respectively singly or multiply substituted or unsubstituted aryl or heteroaryl;
$SR^{10}$ wherein $R^{10}$ is respectively singly or multiply substituted or unsubstituted aryl or heteroaryl; or C(O)NR$^{11}$R$^{12}$, C(O)NR$^{11}$NR$^{12}$R$^{13}$, C(NR$^{11}$)NR$^{12}$R$^{13}$, C(S)NR$^{11}$R$^{12}$ or C(S)NR$^{11}$NR$^{12}$R$^{13}$,
wherein R$^{11}$, R$^{12}$ and R$^{13}$, independently of one another, are
  H; respectively branched or unbranched, singly or multiply substituted or unsubstituted C$_1$–C$_{18}$ alkyl, C$_2$–C$_{18}$ alkenyl or C$_2$–C$_{18}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N; respectively singly or multiply substituted or unsubstituted alkyl aryl or alkyl heteroaryl; or respectively singly or multiply substituted or unsubstituted aryl or heteroaryl;

R$^5$, R$^6$, R$^7$ and R$^8$, independently of one another, are
H, F, Cl, Br, I, CN, NO$_2$;
  respectively branched or unbranched, singly or multiply substituted or unsubstituted C$_1$–C$_{10}$ alkyl, C$_2$–C$_{10}$ alkenyl or C$_2$–C$_{10}$ alkinyl;
  OR$^{14}$, OC(O)R$^{14}$, OC(S)R$^{14}$, C(O)R$^{14}$, C(O)OR$^{14}$, C(S)R$^{14}$, C(S)OR$^{14}$, SR$^{14}$, S(O)R$^{14}$ or S(O$_2$)R$^{14}$, wherein R$^{14}$ is
    H; respectively branched or unbranched, singly or multiply substituted or unsubstituted C$_1$–C$_{10}$ alkyl, C$_2$–C$_{10}$ alkenyl or C$_2$–C$_{10}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N; respectively singly or multiply substituted or unsubstitued alkyl aryl or alkyl heteroaryl; respectively singly or multiply substituted or unsubstituted aryl or heteroaryl;
  NR$^{15}$R$^{16}$, NR$^{15}$C(O)R$^{16}$, C(NR$^{15}$)NR$^{16}$R$^{17}$, NR$^{15}$C(S)R$^{16}$, C(S)NR$^{15}$R$^{16}$ or C(S)NR$^{15}$NR$^{16}$R$^{17}$ or S(O$_2$)NR$^{15}$R$^{16}$, wherein R$^{15}$, R$^{16}$ and R$^{17}$, independently of one another, are
    H, O; respectively branched or unbranched, singly or multiply substituted or unsubstituted C$_1$–C$_{18}$ alkyl, C$_2$–C$_{18}$ alkenyl or C$_2$–C$_{18}$ alkinyl; saturated or unsaturated, singly or multiply substituted or unsubstituted C$_3$–C$_8$ cycloalkyl, or a corresponding heterocycle, in which at least one carbon atom in the ring is replaced by S, O or N, respectively singly or multiply substituted or unsubstituted alkyl aryl or alkyl heteroaryl; or respectively singly or multiply substituted or unsubstituted aryl or heteroaryl; or
    R$^{15}$ and R$^{16}$ or R$^{16}$ and R$^{17}$ together form a saturated or unsaturated, singly or multiply substituted or unsubstituted C$_3$–C$_8$ cycloalkyl, or a corresponding heterocycle in which at least one carbon atom in the ring is replaced by S, O or N; or R$^5$ and R$^6$, R$^6$ and R$^7$ or R$^7$ and R$^8$ together form
=CR$^{18}$—CH=CH—CH= or =CH—CR$^{18}$=CH—CH=,
  wherein R$^{18}$ is
    H, F, Cl, Br, I, OH or respectively branched or unbranched, singly or multiply substituted or unsubstituted C$_1$–C$_{10}$ alkyl, C$_2$–C$_{10}$ alkenyl or C$_2$–C$_{10}$ alkinyl;
provided that
  if R$^1$ and R$^2$ together form —CH=CH—CH$_2$— or

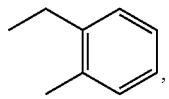

R$^3$ is (–)$_p$-menthan-3-ol, and R$^7$=Cl, then R$^5$, R$^6$ and R$^8$ are not simultaneously H,
  if R$^1$ and R$^2$ together form —CH=CH—CH$_2$—, R$^3$ is CH$_3$, and R$^7$ is H, Cl or OCH$_3$, then R$^5$, R$^6$ and R$^8$ are not simultaneously H,
  if R$^1$ and R$^2$ together form —CH=CH—CH$_2$—, R$^3$ is H, and
  if R$^7$ is OCH$_3$ or C(O)NH$_2$, then R$^5$, R$^6$ and R$^8$ are not simultaneously H,
  if R$^5$=R$^7$=CH$_3$, then R$^6$ and R$^8$ are not simultaneously H,
  if R$^5$=OCH$_3$, then R$^6$, R$^7$ and R$^8$ are not simultaneously H, and
  if R$^1$ and R$^2$ together form

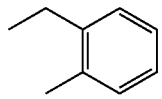

or —O—CH$_2$—CH$_2$— and R$^3$ is C$_2$H$_5$ and
  if R$^7$ is H, Cl, CH$_3$, OCH$_3$ or NO$_2$, then R$^5$, R$^6$ and R$^8$ are not simultaneously H, and
  if R$^5$=NO$_2$; then R$^6$, R$^7$ and R$^8$ are not simultaneously H.

2. A racemate of a substituted 1,2,3,4-tetrahydroquinoline-2-carboxylic acid derivative of claim 1.

3. An enantiomer of a substituted 1,2,3,4-tetrahydroquinoline-2-carboxylic acid derivative of claim 1.

4. A diastereomer of a substituted 1,2,3,4-tetrahydroquinoline-2-carboxylic acid derivative of claim 1.

5. A salt of a physiologically acceptable acid of a substituted 1,2,3,4-tetrahydroquinoline-2-carboxylic acid derivative of claim 1.

6. A mixture of at least two members selected from the group consisting of a racemate, an enantiomer, a diastereomer, and a salt of physiologically acceptable salt of a substituted 1,2,3,4-tetrahydroquinoline-2-carboxylic acid derivative of claim 1.

7. A substituted 1,2,3,4-tetrahydroquinoline-2-carboxylic acid derivative according to claim 1, wherein R$^4$ is R$^{4a}$ or ZR$^{4a}$
  wherein Z is respectively branched or unbranched, singly or multiply substituted or unsubstituted C$_1$–C$_6$ alkyl, C$_2$–C$_6$ alkenyl or C$_2$–C$_6$ alkinyl, and
  wherein R$^{4a}$ is C(O)R$^9$, C(O)OR$^9$, C(S)R$^9$, C(S)OR$^9$ or SO$_2$)R$^9$,
  wherein R$^9$ is phenethyl, 1-adamantyl, 2-adamantyl, 1-naphthyl, 2-naphthyl 2-, 3- or 4-pyridyl, or thiazolyl.

8. A substituted 1,2,3,4-tetrahydroquinoline-2-carboxylic acid derivative according to claim 1, provided that
if $R^1$ and $R^2$ together form —CH=CH—CH$_2$— or

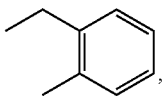

$R^3$ is a $C_3$–$C_8$ saturated or unsaturated cycloalkyl, and R7=Cl,
then R5, R6 and R8 are not simultaneously hydrogen.

9. A substituted 1,2,3,4-tetrahydroquinoline-2-carboxylic acid derivative according to claim 1, wherein $R^4$ is
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl; or
$C(O)R^9$ wherein $R^9$ is
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl; or respectively singly or multiply substituted or unsubstituted aryl or heteroaryl.

10. A substituted 1,2,3,4-tetrahydroquinoline-2-carboxylic acid derivative according to claim 9, wherein $R^9$ is selected from the group consisting of phenethyl, 1-adamantyl, 2-adamantyl, 1-naphthyl, 2-naphthyl 2-, 3- or 4-pyridyl and thiazolyl.

11. A substituted 1,2,3,4-tetrahydroquinoline-2-carboxylic acid derivative according to claim 1, wherein $R^4$ is H; unsubstituted or singly or multiply substituted $C_1$–$C_{10}$ alkyl; or unsubstituted or singly or multiply substituted phenyl.

12. A substituted 1,2,3,4-tetrahydroquinoline-2-carboxylic acid derivative according to claim 11, wherein $R^4$ is H, CH$_3$ or C$_2$H$_5$.

13. A substituted 1,2,3,4-tetrahydroquinoline-2-carboxylic acid derivative according to claim 12, wherein $R^4$ is H.

14. A substituted 1,2,3,4-tetrahydroquinoline-2-carboxylic acid derivatives according to claim 1, wherein $R^3$ is
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted $C_3$–$C_8$ cycloalkyl, or a corresponding heterocycle, in which at least one carbon atom in the ring is replaced by N or O; singly or multiply substituted or unsubstitued alkyl aryl; or respectively singly or multiply substituted or unsubstituted aryl or heteroaryl.

15. A substituted 1,2,3,4-tetrahydroquinoline-2-carboxylic acid derivative according to claim 1, wherein $R^3$ is
H; branched or unbranched, singly or multiply substituted or unsubstituted $C_1$–$C_4$ alkyl; or singly or multiply substituted or unsubstituted phenyl, benzyl or phenethyl.

16. A substituted 1,2,3,4-tetrahydroquinoline-2-carboxylic acid derivatives according to claim 15, wherein $R^3$ is H, CH$_3$ or C$_2$H$_5$.

17. A substituted 1,2,3,4-tetrahydroquinoline-2-carboxylic acid derivatives according to claim 16, wherein $R^3$ is H.

18. A substituted 1,2,3,4-tetrahydroquinoline-2-carboxylic acid derivatives according to claim 1, wherein $R^1$ and $R^2$ together form:
—O—CH$_2$—CH$_2$—, (—CH$_2$—)$_n$ wherein n=3-6, —CH=CH—CH$_2$—,

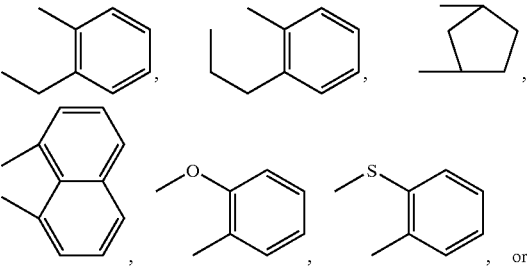

—CH=CH—CH$_2$—CH$_2$—.

19. A substituted 1,2,3,4-tetrahydroquinoline-2-carboxylic acid derivatives according to claim 18, wherein $R^1$ and $R^2$ together form (—CH$_2$—)$_3$ or (—CH$_2$—)$_6$.

20. A substituted 1,2,3,4-tetrahydroquinoline-2-carboxylic acid derivatives according to claim 18, wherein $R^1$ and $R^2$ together form —CH=CH—CH$_2$— or —CH=CH—CH$_2$—CH$_2$—.

21. A substituted 1,2,3,4-tetrahydroquinoline-2-carboxylic acid derivatives according to claim 20, wherein $R^1$ and $R^2$ together form —CH=CH—CH$_2$—.

22. A substituted 1,2,3,4-tetrahydroquinoline-2-carboxylic acid derivatives according to claim 1, wherein $R^5$, $R^6$, $R^7$ and $R^8$, independently of one another, are
H, F, Cl, Br, I, CN, NO$_2$; respectively branched or unbranched, singly or multiply substituted or unsubstituted $C_1$–$C_{10}$ alkyl, $C_2$–$C_{10}$ alkenyl or $C_2$–$C_{10}$ alkinyl; OR$^{14}$, C(O)R$^{14}$, C(O)OR$^{14}$ or SR$^{14}$, wherein $R^{14}$ is
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstiued alkyl aryl or alkyl heteroaryl; or respectively singly or multiply substituted or unsubstituted aryl or heteroaryl; or
NR$^{15}$R$^{16}$, NR$^{15}$C(O)R$^{16}$, wherein $R^{15}$ and $R^{16}$, independently of one another, are
H, O; or respectively branched or unbranched, singly or multiply substituted or unsubstituted $C_1$–$C_{10}$ alkyl, $C_2$–$C_{10}$ alkenyl or $C_2$–$C_{10}$ alkinyl.

23. A substituted 1,2,3,4-tetrahydroquinoline-2-carboxylic acid derivatives according to claim 1, wherein $R^5$, $R^6$, $R^7$ and $R^8$, independently of one another, are
H, F, Cl, Br, I, CN, NO$_2$; respectively branched or unbranched, singly or multiply substituted or unsubstituted $C_1$–$C_6$ alkyl, $C_2$–$C_6$ alkenyl or $C_2$–$C_6$ alkinyl; or OR$^{14}$, C(O)R$^{14}$, C(O)OR$^{14}$ or SR$^{14}$, wherein $R^{14}$ is
H; branched or unbranched, singly or multiply substituted or unsubstituted $C_1$–$C_4$ alkyl; or singly or multiply substituted or unsubstituted aryl.

24. A substituted 1,2,3,4-tetrahydroquinoline-2-carboxylic acid derivatives according to claim 23, wherein $R^5$, $R^6$, $R^7$ and $R^8$, independently of one another, are
H, F, Cl, Br, I, CN; branched or unbranched, singly or multiply substituted or unsubstituted $C_1$–$C_4$ alkyl; or OR$^{14}$ or SR$^{14}$, wherein R$^{14}$ is
branched or unbranched, singly or multiply substituted or unsubstituted C$_1$–C$_4$ alkyl; or singly or multiply substituted or unsubstituted aryl.

25. A substituted 1,2,3,4-tetrahydroquinoline-2-carboxylic acid derivatives according to claim 24, wherein R$^5$, R$^6$, R$^7$ and R$^8$, independently of one another, are selected from the group consisting of H, F, Cl, Br, I, CN; CH$_3$, CF$_3$, t-butyl, i-butyl, —OCH$_3$, —OCF$_3$, —SCH$_3$, and —O-phenyl.

26. A substituted 1,2,3,4-tetrahydroquinoline-2-carboxylic acid derivatives according to claim 1, wherein R$^5$, R$^6$ and R$^8$ are all H and R$^7$ is Cl, or wherein R$^5$ and R$^7$ are both H and R$^6$ and R$^8$ are both Cl.

27. A substituted 1,2,3,4-tetrahydroquinoline-2-carboxylic acid derivatives according to claim 1, wherein R3 and R4 are both H, and wherein
R$^5$, R$^6$ and R$^8$ are all H and R$^7$ is Cl, or
R$^5$ and R$^7$ are H and R$^6$ and R$^8$ are Cl.

28. A substituted 1,2,3,4-tetrahydroquinoline-2-carboxylic acid derivatives according to claim 1, selected from the group consisting of:
7,9-dichloro-3a,4,5,9b-tetrahydro-3H-cyclopenta[c]quinoline-4-carboxylic acid ethyl ester,
7,9-dichloro-3a,4,5,9b-tetrahydro-3H-cyclopenta[c]quinoline-4-carboxylic acid,
8-chloro-3a,4,5,9b-tetrahydro-3H-cyclopenta[c]quinoline-4-carboxylic acid ethyl ester,
8-chloro-3a-4,5,9b-tetrahydro-3H-cyclo-penta[c]quinoline-4-carboxylic acid,
2-phenoxy-5,6a,11,11a-tetrahydro-6H-inden[1,2-c]quinoline-4-carboxylic acid ethyl ester,
1,3-dichloro-5,6,6a,7,8,12b-hexahydrobenzo[k]phenanthridine-6-carboxylic acid ethyl ester,
7,9-dichloro-2,3,3a,4,5,9b-hexahydro-1H-cyclopenta[c]quinoline-4-carboxylic acid ethyl ester,
1,3-dichloro-7,10-methano-5,6,6a,7,8,9,10,10a-octahydrophenanthridine-6-carboxylic acid ethyl ester,
5,6a,7,11b-tetrahydro-6H-indeno-[2,1-c]quinoline-6-carboxylic acid ethyl ester,
10,12-dichloro-6b,7,8,12b-tetrahydro-8-azabenzo[j]fluoroanthrene-7-carboxylic acid ethyl ester,
1,3-dichloro-5,6,6a,11a-tetrahydro-11-oxa-5-aza-benzo[a]fluoroene-6-carboxylic acid ethyl ester,
1,3-dichloro-5,6,6a,11a-tetrahydro-11-thia-5-aza-benzo[a]fluoroene-6-carboxylic acid ethyl ester,
6,8,9-trichloro-2,3,3a,4,5,9b-hexahydro-furo[3,2-c]quinoline-4-carboxylic acid, and
2-trifluoromethoxy-5,6,6a,7,8,9,10,11,12,12a-decahydro-5-aza-cycloocta-[a]naphthalene-6-carboxylic acid ethyl ester.

29. A substituted 1,2,3,4-tetrahydroquinoline-2-carboxylic acid derivatives according to claim 28, selected from the group consisting of:
7,9-dichloro-3a,4,5,9b-tetrahydro-3H-cyclopenta[c]quinoline-4-carboxylic acid ethyl ester,
7,9-dichloro-3a,4,5,9b-tetrahydro-3H-cyclopenta[c]quinoline-4-carboxylic acid,
8-chloro-3a,4,5,9b-tetrahydro-3H-cyclopenta[c]quinoline-4-carboxylic acid ethyl ester,
8-chloro-3a-4,5,9b-tetrahydro-3H-cyclo-penta[c]quinoline-4-carboxylic acid,
1,3-dichloro-5,6,6a,7,8,12b-hexahydrobenzo[k]phenanthridine-6-carboxylic acid ethyl ester,
7,9-dichloro-2,3,3a,4,5,9b-hexahydro-1H-cyclopenta[c]quinoline-4-carboxylic acid ethyl ester,
1,3-dichloro-7,10-methano-5,6,6a,7,8,9,10,10a-octahydrophenanthridine-6-carboxylic acid ethyl ester,
5,6a,7,11b-tetrahydro-6H-indeno-[2,1-c]quinoline-6-carboxylic acid ethyl ester,
10,12-dichloro-6b,7,8,12b-tetrahydro-8-azabenzo[j]fluoroanthrene-7-carboxylic acid ethyl ester,
1,3-dichloro-5,6,6a,11a-tetrahydro-11-oxa-5-aza-benzo[a]fluoroene-6-carboxylic acid ethyl ester, and
1,3-dichloro-5,6,6a,11a-tetrahydro-11-thia-5-aza-benzo[a]fluoroene-6-carboxylic acid ethyl ester.

30. A substituted 1,2,3,4-tetrahydroquinoline-2-carboxylic acid derivatives according to claim 28, selected from the group consisting of:
7,9-dichloro-3a,4,5,9b-tetrahydro-3H-cyclopenta[c]quinoline-4-carboxylic acid, and
8-chloro-3a-4,5,9b-tetrahydro-3H-cyclo-penta[c]quinoline-4-carboxylic acid.

31. A salt of a physiologically acceptable acid of a substituted 1,2,3,4-tetrahydroquinoline-2-carboxylic acid derivative of claim 5, wherein the salt is a hydrochloride salt.

32. A method for preparing a substituted 1,2,3,4-tetrahydroquinoline-2-carboxylic acid derivative of formula I

I wherein
R$^1$ and R$^2$ together form:
—(CH$_2$)$_n$— with n=3-10,
—CH=CH—CH$_2$—,
—CH=CH—CH$_2$—CH$_2$—,
—CH$_2$—CH=CH—CH$_2$—,
—CH$_2$—CH=CH—CH$_2$—CH$_2$—,
—CH$_2$—CH$_2$—CH=CH—CH$_2$—CH$_2$—,
—O—CH$_2$—CH$_2$—,
—O—CH$_2$—CH$_2$—CH$_2$—,
—CH$_2$—O—CH$_2$—,
—CH$_2$—CH$_2$—O—CH$_2$—, X = O or S which is singly or multiply substituted or unsubstituted;
R$^3$ is
H; respectively branched or unbranched, singly or multiply substituted or unsubstituted C$_1$–C$_{18}$ alkyl, C$_2$–C$_{18}$ alkenyl or C$_2$–C$_{18}$ alkinyl; saturated or unsaturated, singly or multiply substituted or unsubstituted $C_3$–$C_8$ cycloalkyl, or a corresponding heterocycle, in which at least one carbon atom in the ring is replaced by N, S or O; respectively singly or multiply substituted or unsubstituted alkyl aryl or alkyl heteroaryl; or respectively singly or multiply substituted or unsubstituted aryl or heteroaryl;

$R^4$ is H;

$R^5$, $R^6$, $R^7$ and $R^8$, independently of one another, are
H, F, Cl, Br, I, CN, $NO_2$;
respectively branched or unbranched, singly or multiply substituted or unsubstituted $C_1$–$C_{10}$ alkyl, $C_2$–$C_{10}$ alkenyl or $C_2$–$C_{10}$ alkinyl;
$OR^{14}$, $OC(O)R^{14}$, $OC(S)R^{14}$, $C(O)R^{14}$, $C(O)OR^{14}$, $C(S)R^{14}$, $C(S)OR^{14}$, $SR^{14}$, $S(O)R^{14}$ or $S(O_2)R^{14}$, wherein $R^{14}$ is
H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstitued alkyl aryl or alkyl heteroaryl; respectively singly or multiply substituted or unsubstituted aryl or heteroaryl;
$NR^{15}R^{16}$, $NR^{15}C(O)R^{16}$, $C(NR^{15})NR^{16}R^{17}$, $NR^{15}C(S)R^{16}$, $C(S)NR^{15}R^{16}$ or $C(S)NR^{15}NR^{16}R^{17}$ or $S(O_2)NR^{15}R^{16}$, wherein $R^{15}$, $R^{16}$ and $R^{17}$, independently of one another, are
H, O; respectively branched or unbranched, singly or multiply substituted or unsubstituted $C_1$–$C_{18}$ alkyl, $C_2$–$C_{18}$ alkenyl or $C_2$–$C_{18}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N, respectively singly or multiply substituted or unsubstituted alkyl aryl or alkyl heteroaryl; or respectively singly or multiply substituted or unsubstituted aryl or heteroaryl; or
$R^{15}$ and $R^{16}$ or $R^{16}$ and $R^{17}$ together form a saturated or unsaturated, singly or multiply substituted or unsubstituted $C_3$–$C_8$ cycloalkyl, or a corresponding heterocycle in which at least one carbon atom in the ring is replaced by S, O or N; or $R^5$ and $R^6$, $R^6$ and $R^7$ or $R^7$ and $R^8$ together form
=$CR^{18}$—CH=CH—CH= or =CH—$CR^{18}$=CH—CH=,
wherein $R^{18}$ is
H, F, Cl, Br, I, OH or respectively branched or unbranched, singly or multiply substituted or unsubstituted $C_1$–$C_{10}$ alkyl, $C_2$–$C_{10}$ alkenyl or $C_2$–$C_{10}$ alkinyl;
provided that
if $R^1$ and $R^2$ together form —CH=CH—$CH_2$— or

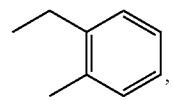, $R^3$ is $(-)_p$-menthan-3-ol, and $R^7$=Cl, then $R^5$, $R^6$ and $R^8$ are not simultaneously H,
if $R^1$ and $R^2$ together form —CH=CH—$CH_2$—, $R^3$ is $CH_3$, and $R^7$ is H, Cl or $OCH_3$, then $R^5$, $R^6$ and $R^8$ are not simultaneously H, if $R^1$ and $R^2$ together form —CH=CH—$CH_2$—, $R^3$ is H, and
if $R^7$ is $OCH_3$ or $C(O)NH_2$, then $R^5$, $R^6$ and $R^8$ are not simultaneously H,
if $R^5$=$R^7$=$CH_3$, then $R^6$ and $R^8$ are not simultaneously H,
if $R^5$=$OCH_3$, then $R^6$, $R^7$ and $R^8$ are not simultaneously H, and
if $R^1$ and $R^2$ together form

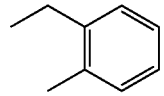

or —O—$CH_2$—$CH_2$— and $R^3$ is $C_2H_5$ and
if $R^7$ is H, Cl, $CH_3$, $OCH_3$ or $NO_2$, then $R^5$, $R^6$ and $R^8$ are not simultaneously H, and
if $R^5$=$NO_2$; then $R^6$, $R^7$ and $R^8$ are not simultaneously H, the method comprising
reacting in a reaction an aniline of formula II:

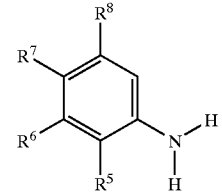

with a glyoxalic acid ester of formula III:

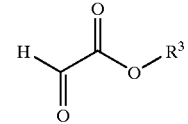

and an olefin of formula IV,

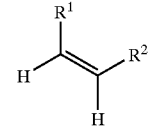

in trifluoroacetic acid at between about 0° and about 100° C.

33. A method according to claim 32, wherein the reaction lasts 0.25 to 12 hours.

34. A method according to claim 33, wherein the reaction lasts not more than 2 hours.

35. A method according to claim 32, wherein the reaction takes place at a temperature between about 20° and about 40° C.

36. A method according to claim 35, wherein the reaction takes place at room temperature.

37. A method according to claim 36, wherein the reaction is a one-pot reaction.

38. A method according to claim 32, wherein the reaction is a one-pot reaction.

39. A method according to claim 32, wherein at least one OH group of the compounds of formulae II, III and IV is replaced by a OSi(Ph)₂tert-butyl group.

40. A method according to claim 32, wherein at least one SH group of the compounds of formulae II, III and IV is replaced by a S-p-methoxybenzyl group.

41. A method according to claim 32, wherein at least one NH₂ group of the compounds of formulae II, III and IV is replaced by a NO₂ group.

42. A method according to claim 39, wherein the substituted 1,2,3,4-tetrahydroquinoline-2-carboxylic acid derivative of formula I is purified and prior to purification, at least one OSi(Ph)₂tert-butyl group is eliminated with tetrabutyl ammonium fluoride in tetrahydrofuran.

43. A method according to claim 40, wherein the substituted 1,2,3,4-tetrahydroquinoline-2-carboxylic acid derivative of formula I is purified and prior to purification, at least one p-methoxybenzyl group is eliminated with a metal amide.

44. A method according to claim 43, wherein the at least one p-methoxybenzyl group is eliminated with sodium amide.

45. A method according to claim 41, wherein the substituted 1,2,3,4-tetrahydroquinoline-2-carboxylic acid derivative of formula I is purified and prior to purification, at least one NO₂ group(s) is reduced to NH₂.

46. A method according to claim 32, wherein the substituted 1,2,3,4-tetrahydroquinoline-2-carboxylic acid derivative of formula I is purified and prior to purification, an intermediate having at least one C(O)OCH₃ or C(S)OCH₃ group is saponified with KOH solution or NaOH solution in methanol at 40 to 60° C.

47. A method for preparing a substituted 1,2,3,4-tetrahydroquinoline-2-carboxylic acid derivative of formula I:

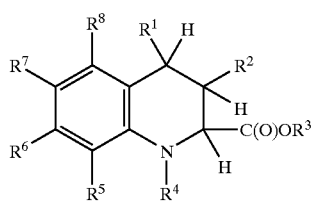

wherein
R¹ and R² together form:
—(CH₂)ₙ— with n=3–10,
—CH=CH—CH₂—,
—CH=CH—CH₂—CH₂—,
—CH₂—CH=CH—CH₂—,
—CH₂—CH=CH—CH₂—CH₂—,
—CH₂—CH₂—CH=CH—CH₂—CH₂—,
—O—CH₂—CH₂—,
—O—CH₂—CH₂—CH₂—,
—CH₂—O—CH₂—,
—CH₂—CH₂—O—CH₂—,

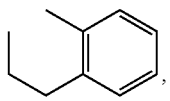 , 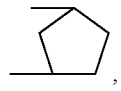 , 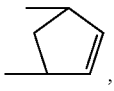 ,

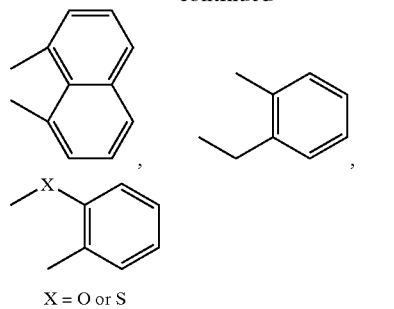

X = O or S which is singly or multiply substituted or unsubstituted;

R³ is
H; respectively branched or unbranched, singly or multiply substituted or unsubstituted C₁–C₁₈ alkyl, C₂–C₁₈ alkenyl or C₂–C₁₈ alkinyl; saturated or unsaturated, singly or multiply substituted or unsubstituted C₃–C₈ cycloalkyl, or a corresponding heterocycle, in which at least one carbon atom in the ring is replaced by N, S or O; respectively singly or multiply substituted or unsubstituted alkyl aryl or alkyl heteroaryl; or respectively singly or multiply substituted or unsubstituted aryl or heteroaryl;

R⁴ is
R⁴ᵃ or ZR⁴ᵃ wherein Z is respectively branched or unbranched, singly or multiply substituted or unsubstituted C₁–C₆ alkyl, C₂–C₆ alkenyl or C₂–C₆ alkinyl, and wherein R⁴ᵃ is
respectively branched or unbranched, singly or multiply substituted or unsubstituted C₁–C₁₂ alkyl, C₂–C₁₂ alkenyl or C₂–C₁₂ alkinyl; saturated or unsaturated, singly or multiply substituted or unsubstituted C₃–C₈ cycloalkyl, or a corresponding heterocycle, in which at least one carbon atom in the ring is replaced by S, O or N; respectively singly or multiply substituted or unsubstituted aryl or heteroaryl;
C(O)R⁹, C(O)OR⁹, C(S)R⁹, C(S)OR⁹ or SO₂)R⁹, wherein R⁹ is
H; respectively branched or unbranched, singly or multiply substituted or unsubstituted C₁–C₁₀ alkyl, C₂–C₁₀ alkenyl or C₂–C₁₀ alkinyl; saturated or unsaturated, singly or multiply substituted or unsubstituted C₃–C₈ cycloalkyl, or a corresponding heterocycle, in which at least one carbon atom in the ring is replaced by S, O or N; respectively singly or multiply substitued alkyl aryl or alkyl heteroaryl; or respectively singly or multiply substituted or unsubstituted aryl or heteroaryl;
SR¹⁰ wherein R¹⁰ is respectively singly or multiply substituted or unsubstituted aryl or heteroaryl; or
C(O)NR¹¹R¹², C(O)NR¹¹NR¹²R¹³, C(NR¹¹)NR¹²R¹³, C(S)NR¹¹R¹² or C(S)NR¹¹NR¹²R¹³, wherein R¹¹, R¹² and R¹³, independently of one another, are
H; respectively branched or unbranched, singly or multiply substituted or unsubstituted C₁–C₁₈ alkyl, C₂–C₁₈ alkenyl or C₂–C₁₈ alkinyl; saturated or unsaturated, singly or multiply substituted or unsubstituted C₃–C₈ cycloalkyl, or a corresponding heterocycle, in which at least one carbon atom in the ring is replaced by S, O or N; respectively singly or multiply substituted or unsubstituted alkyl aryl or alkyl heteroaryl; or respectively singly or multiply substituted or unsubstituted aryl or heteroaryl;

$R^5$, $R^6$, $R^7$ and $R^8$, independently of one another, are H, F, Cl, Br, I, CN, $NO_2$;

respectively branched or unbranched, singly or multiply substituted or unsubstituted $C_1$–$C_{10}$ alkyl, $C_2$–$C_{10}$ alkenyl or $C_2$–$C_{10}$ alkinyl;

$OR^{14}$, $OC(O)R^{14}$, $OC(S)R^{14}$, $C(O)R^{14}$, $C(O)OR^{14}$, $C(S)R^{14}$, $C(S)OR^{14}$, $SR^{14}$, $S(O)R^{14}$ or $S(O_2)R^{14}$, wherein $R^{14}$ is H; respectively branched or unbranched, singly or multiply substituted or unsubstituted $C_1$–$C_{10}$ alkyl, $C_2$–$C_{10}$ alkenyl or $C_2$–$C_{10}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N; respectively singly or multiply substituted or unsubstitued alkyl aryl or alkyl heteroaryl; respectively singly or multiply substituted or unsubstituted aryl or heteroaryl;

$NR^{15}R^{16}$, $NR^{15}C(O)R^{16}$, $C(NR^{15})NR^{16}R^{17}$, $NR^{15}C(S)R^{16}$, $C(S)NR^{15}R^{16}$ or $C(S)NR^{15}NR^{16}R^{17}$ or $S(O_2)NR^{15}R^{16}$, wherein $R^{15}$, $R^{16}$ and $R^{17}$, independently of one another, are H, O; respectively branched or unbranched, singly or multiply substituted or unsubstituted $C_1$–$C_{18}$ alkyl, $C_2$–$C_{18}$ alkenyl or $C_2$–$C_{18}$ alkinyl; saturated or unsaturated, singly or multiply substituted or unsubstituted $C_3$–$C_8$ cycloalkyl, or a corresponding heterocycle, in which at least one carbon atom in the ring is replaced by S, O or N, respectively singly or multiply substituted or unsubstituted alkyl aryl or alkyl heteroaryl; or respectively singly or multiply substituted or unsubstituted aryl or heteroaryl; or $R^{15}$ and $R^{16}$ or $R^{16}$ and $R^{17}$ together form a saturated or unsaturated, singly or multiply substituted or unsubstituted $C_3$–$C_8$ cycloalkyl, or a corresponding heterocycle in which at least one carbon atom in the ring is replaced by S, O or N; or $R^5$ and $R^6$, $R^6$ and $R^7$ or $R^7$ and $R^8$ together form =$CR^{18}$—CH=CH—CH= or =CH—$CR^{18}$=CH—CH=, wherein $R^{18}$ is H, F, Cl, Br, I, OH or respectively branched or unbranched, singly or multiply substituted or unsubstituted $C_1$–$C_{10}$ alkyl, $C_2$–$C_{10}$ alkenyl or $C_2$–$C_{10}$ alkinyl;

provided that if $R^1$ and $R^2$ together form —CH=CH—$CH_2$— or

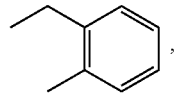

$R^3$ is (–)$_p$-menthan-3-ol, and $R^7$=Cl, then $R^5$, $R^6$ and $R^8$ are not simultaneously H, if $R^1$ and $R^2$ together form —CH=CH—$CH_2$—, $R^3$ is $CH_3$, and $R^7$ is H, Cl or $OCH_3$, then $R^5$, $R^6$ and $R^8$ are not simultaneously H, if $R^1$ and $R^2$ together form —CH=CH—$CH_2$—, $R^3$ is H, and if $R^7$ is $OCH_3$ or $C(O)NH_2$, then $R^5$, $R^6$ and $R^8$ are not simultaneously H, if $R^5$=$R^7$=$CH_3$, then $R^6$ and $R^8$ are not simultaneously H, if $R^5$=$OCH_3$, then $R^6$, $R^7$ and $R^8$ are not simultaneously H, and if $R^1$ and $R^2$ together form

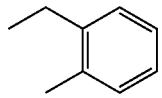

or —O—$CH_2$—$CH_2$— and $R^3$ is $C_2H_5$ and if $R^7$ is H, Cl, $CH_3$, $OCH_3$ or $NO_2$, then $R^5$, $R^6$ and $R^8$ are not simultaneously H, and if $R^5$=$NO_2$; then $R^6$, $R^7$ and $R^8$ are not simultaneously H, the method comprising reacting a substituted 1,2,3,4-tetrahydroquinoline-2-carboxylic acid derivative of formula I wherein $R^4$=H, so that the hydrogen is suitably substituted for $R^4$.

48. A method according to claim 47, wherein at least one OH group of a reactant or an intermediate of the reaction is replaced by a OSi(Ph)$_2$tert-butyl group, and wherein the substituted 1,2,3,4-tetrahydroquinoline-2-carboxylic acid derivative of formula I is purified and prior to purification, the at least one OSi(Ph)$_2$tert-butyl group is eliminated with tetrabutyl ammonium fluoride in tetrahydrofuran.

49. A method according to claim 47, wherein at least one SH group of a reactant or an intermediate of the reaction is replaced by S-p-methoxybenzyl group, and wherein the substituted 1,2,3,4-tetrahydroquinoline-2-carboxylic acid derivative of formula I is purified and prior to purification, the at least one S-p-methoxybenzyl group is eliminated with with a metal amide.

50. A method according to claim 49, wherein the at least one p-methoxybenzyl group is eliminated with sodium amide.

51. A method according to claim 47, wherein at least one $NH_2$ group of a reactant or an intermediate of the reaction is replaced by a $NO_2$ group, and wherein the substituted 1,2,3,4-tetrahydroquinoline-2-carboxylic acid derivative of formula I is purified and prior to purification, the at least one $NO_2$ group(s) is reduced to $NH_2$.

52. A method according to claim 47, wherein the substituted 1,2,3,4-tetrahydroquinoline-2-carboxylic acid derivative of formula I is purified and prior to purification, an intermediate having at least one $C(O)OCH_3$ or $C(S)OCH_3$ group is saponified with KOH solution or NaOH solution in methanol at 40 to 60° C.

53. A pharmaceutical composition comprising a substituted 1,2,3,4-tetrahydroquinoline-2-carboxylic acid derivative of claim 1, and a pharmaceutically acceptable excipient.

54. A pharmaceutical composition according to claim 53, comprising a salt of a physiologically acceptable acid of a substituted 1,2,3,4-tetrahydroquinoline-2-carboxylic acid derivative.

55. A pharmaceutical composition of claim 54, wherein the salt is a hydrochloride salt.

56. A pharmaceutical composition according to claim 54, wherein in formula I, $R^5$, $R^6$ and $R^8$ are all H and $R^7$ is Cl; or $R^5$ and $R^7$ are both H, and $R^6$ and $R^8$ are Cl.

57. A method for the treatment of pain, comprising administering to a patient in need thereof an effective pain-treating amount of a pharmaceutical composition of claim 53.

58. A method according to claim 57, wherein the pain is neuropathic pain, or chronic pain, or both.

59. A method for the treatment of migraine, comprising administering to a patient in need thereof an effective migraine-treating amount of a pharmaceutical composition of claim 53.

60. A method for the treatment of at least one disease selected from the group consisting of urinary incontinence, itching, tinnitus aurium and diarrhea, comprising administering to a patient in need thereof an effective amount of a pharmaceutical composition of claim 53.

61. A method for the treatment of at least one disease selected from the group consisting of epilepsy, Parkinson's disease, Huntington's chorea, glaucoma, osteoporosis, ototoxicity, withdrawal symptoms following alcohol or drug abuse, stroke, cerebral ischaemia, cerebral infarcts, cerebral oedema, hypoxia, anoxia, anxiolysis and anaesthesia, comprising administering to a patient in need thereof an effective amount of a pharmaceutical composition of claim 53.

62. A method for the treatment of at least one disease selected from the group consisting of schizophrenia, Alzheimer's disease, psychoses caused by a raised amino acid level, AIDS, dementia, encephalomyelitis, Gilles de La Tourette's syndrome, perinatal asphyxia, inflammatory reactions, allergic reactions, depression, drug abuse, alcohol abuse, gastritis, diabetes, cardiovascular disease, respiratory tract disease, coughs and mental illnesses, comprising administering to a patient in need thereof an effective amount of a pharmaceutical composition of claim 53.

\* \* \* \* \*